(12) United States Patent
Sessler et al.

(10) Patent No.: US 11,389,459 B2
(45) Date of Patent: *Jul. 19, 2022

(54) TEXAPHYRIN-PT(IV) CONJUGATES AND COMPOSITIONS FOR USE IN OVERCOMING PLATINUM RESISTANCE

(71) Applicant: BOARD OF REGENTS, THE UNIVERSITY OF TEXAS SYSTEM, Austin, TX (US)

(72) Inventors: Jonathan L. Sessler, Austin, TX (US); Jonathan Arambula, Austin, TX (US); Zahid H. Siddik, Houston, TX (US); Gregory Thiabaud, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/563,714

(22) Filed: Sep. 6, 2019

(65) Prior Publication Data

US 2020/0069698 A1 Mar. 5, 2020

Related U.S. Application Data

(63) Continuation of application No. 15/317,560, filed as application No. PCT/US2015/035229 on Jun. 11, 2015, now Pat. No. 10,406,167.

(60) Provisional application No. 62/135,502, filed on Mar. 19, 2015, provisional application No. 62/010,841, filed on Jun. 11, 2014.

(51) Int. Cl.
| | |
|---|---|
| *A61K 31/555* | (2006.01) |
| *A61K 31/407* | (2006.01) |
| *A61K 31/4188* | (2006.01) |
| *C07D 487/22* | (2006.01) |
| *C07D 405/14* | (2006.01) |
| *A61K 47/54* | (2017.01) |
| *A61K 47/60* | (2017.01) |
| *A61K 49/08* | (2006.01) |
| *A61K 49/10* | (2006.01) |
| *C07F 15/00* | (2006.01) |

(52) U.S. Cl.
CPC .......... *A61K 31/555* (2013.01); *A61K 47/546* (2017.08); *A61K 47/547* (2017.08); *A61K 47/60* (2017.08); *A61K 49/085* (2013.01); *A61K 49/10* (2013.01); *A61K 49/106* (2013.01); *C07D 487/22* (2013.01); *C07F 15/0093* (2013.01)

(58) Field of Classification Search
CPC ............... A61K 31/555; A61K 31/407; A61K 31/4188; C07D 487/22; C07D 405/14; C07F 15/0093; C07F 15/0086
USPC .................. 514/185; 548/402, 108
See application file for complete search history.

(56) References Cited

U.S. PATENT DOCUMENTS

| | | | |
|---|---|---|---|
| 4,265,823 | A | 5/1981 | Nobile |
| 4,845,124 | A | 7/1989 | Kidani et al. |
| 4,935,498 | A | 6/1990 | Sessler et al. |
| 4,980,473 | A | 12/1990 | Barton |
| 5,072,011 | A | 12/1991 | Abrams et al. |
| 5,272,142 | A | 12/1993 | Sessler et al. |
| 5,292,414 | A | 3/1994 | Sessler et al. |
| 5,369,101 | A | 11/1994 | Sessler et al. |
| 5,409,915 | A | 4/1995 | Farrell |
| 5,432,171 | A | 7/1995 | Sessler et al. |
| 5,439,570 | A | 8/1995 | Sessler et al. |
| 5,504,205 | A | 4/1996 | Sessler et al. |
| 5,569,759 | A | 10/1996 | Sessler et al. |
| 5,583,220 | A | 12/1996 | Sessler et al. |
| 5,587,463 | A | 12/1996 | Sessler et al. |
| 5,591,422 | A | 1/1997 | Hemmi et al. |
| 5,599,923 | A | 2/1997 | Sessler et al. |
| 5,599,928 | A | 2/1997 | Hemmi et al. |
| 5,624,919 | A | 4/1997 | Farrell |
| 5,633,354 | A | 5/1997 | Magda et al. |
| 5,776,925 | A | 7/1998 | Young et al. |
| 5,955,586 | A | 9/1999 | Sessler et al. |
| 5,994,535 | A | 11/1999 | Sessler et al. |
| 6,207,660 | B1 | 3/2001 | Sessler et al. |
| 7,112,671 | B2 | 9/2006 | Mody et al. |
| 7,655,697 | B2 | 2/2010 | Franc et al. |
| 7,655,810 | B2 | 2/2010 | Kodama et al. |
| 8,193,175 | B2 | 6/2012 | Pfeffer et al. |

(Continued)

FOREIGN PATENT DOCUMENTS

| | | |
|---|---|---|
| CN | 102058576 | 5/2011 |
| WO | WO 98/24424 | 6/1998 |

(Continued)

OTHER PUBLICATIONS

Hannah, S., V. Lynch, D. Guldi, N. Gerasimchuk, C. MacDonald, D. Magda, and J. Sessler, "Late first-row transition-metal complexes of Texaphyrin", J. Am. Chem. Soc. 2002, 124, pp. 8416-8427. (Year: 2002).*

(Continued)

*Primary Examiner* — Joseph R Kosack
*Assistant Examiner* — Sagar Patel
(74) *Attorney, Agent, or Firm* — Parker Highlander PLLC

(57) ABSTRACT

The present disclosure relates platinum(IV) and texaphyrin linked conjugates and compositions comprising a texaphyrin and a platinum(IV) agent. The present disclosure also provides pharmaceutical compositions of the conjugates and compositions. Also, provided herein are methods of using the instant compounds in the treatment of cancer such as a platinum resistant cancer.

18 Claims, 36 Drawing Sheets

(56) References Cited

U.S. PATENT DOCUMENTS

| | | | |
|---|---|---|---|
| 8,357,678 | B2 | 1/2013 | Mei |
| 8,410,263 | B2 | 4/2013 | Madden et al. |
| 8,481,496 | B2 | 7/2013 | Fregona et al. |
| 8,563,712 | B2 | 10/2013 | Che et al. |
| 8,653,132 | B2 | 2/2014 | Bose |
| 8,729,286 | B2 | 5/2014 | Lippard et al. |
| 8,748,484 | B2 | 6/2014 | Reddy |
| 8,828,984 | B2 | 9/2014 | Che et al. |
| 8,877,215 | B2 | 11/2014 | MacDonnell et al. |
| 10,406,167 | B2 | 9/2019 | Sessler et al. |
| 2006/0160784 | A1 | 7/2006 | Magda et al. |
| 2012/0164230 | A1 | 6/2012 | Feazell et al. |
| 2013/0303606 | A1 | 11/2013 | Lippard et al. |
| 2014/0221475 | A1 | 8/2014 | Arai et al. |
| 2014/0274988 | A1 | 9/2014 | Lippard et al. |

FOREIGN PATENT DOCUMENTS

| | | |
|---|---|---|
| WO | WO 99/62551 | 12/1999 |
| WO | WO 2001/032211 | 3/2010 |
| WO | WO 2010/027428 | 3/2010 |
| WO | WO 2012/177935 | 12/2012 |
| WO | WO 2013/086804 | 6/2013 |
| WO | WO 2014/165782 | 10/2014 |

OTHER PUBLICATIONS

Arambula et al. "Gadolinium texaphyrin (Gd-Tex)-malonatoplatinum conjugates: Synthesis and comparison with carboplatin in normal and Pt-resistant cell lines." *Dalton Transactions* 48 (2009): 10834-10840.

Arambula et al. "Texaphyrins: tumor localizing redox active expanded porphyrins." *Anti-Cancer Agents in Medicinal Chemistry (Formerly Current Medicinal Chemistry-Anti-Cancer Agents)* 11.2 (2011): 222-232.

Arambula et al., "A texaphyrin-oxaliplatin conjugate that overcomes both pharmacologic and molecular mechanisms of cisplatin resistance in cancer cells." *MedChemComm* 3.10 (2012): 1275-1281.

Arambula et al., "Overcoming biochemical pharmacologic mechanisms of platinum resistance with a texaphyrin-platinum conjugate." *Bioorganic & medicinal chemistry letters* 21.6 (2011): 1701-1705.

Barnes et al., "Synthesis, characterization, and cytotoxicity of a series of estrogen-tethered platinum (IV) complexes." *Chemistry & biology* 11.4 (2004): 557-564.

Chen et al. "Influence of equatorial and axial carboxylato ligands on the kinetic inertness of platinum (IV) complexes in the presence of ascorbate and cysteine and within DLD-1 cancer cells." *Journal of medicinal chemistry* 56.21 (2013): 8757-8764.

Davies et al. "[1H, 15N] Heteronuclear Single Quantum Coherence NMR Study of the Mechanism of Aquation of Platinum (IV) Ammine Complexes." *Inorganic chemistry* 47.17 (2008): 7673-7680.

Drougge and Elding. "Mechanisms for acceleration of halide anation reactions of platinum (IV) complexes. REOA versus ligand assistance and platinum (II) catalysis without central ion exchange." *Inorganica chimica acta* 121.2 (1986): 175-183.

Elding and Gustafson. "A reaction mechanism for oxidative addition of halogen to platinum (II), reductive elimination of halide from platinum (IV) and halide assisted anations of platinum (IV) complexes." *Inorganica Chimica Acta* 19 (1976): 165-171.

Extended European Search Report, issued in corresponding European Application No. 15806650.6, dated Nov. 22, 2017.

Gabano et al., "Pros and cons of bifunctional platinum (IV) antitumor prodrugs: two are (not always) better than one." *Dalton Transactions* 43.26 (2014): 9813-9820.

Gibson, "Platinum (IV) anticancer prodrugs—hypotheses and facts." *Dalton Transactions* 45.33 (2016): 12983-12991.

Hall et al., "Quantitative measurement of the reduction of platinum (iv) complexes using X-ray absorption near-edge spectroscopy (XANES)." *Metallomics* 4.6 (2012): 568-575.

Hall et al. "The cellular distribution and oxidation state of platinum (II) and platinum (IV) antitumour complexes in cancer cells." *JBIG Journal of Biological Inorganic Chemistry* 8.7 (2003): 726-732.

Hall et al., "Platinum(IV) antitumour compounds: their bioinorganic chemistry", *Coord. Chem. Ref.*, 232:49, 2002.

Hannah et al. "Synthesis of a metal-free texaphyrin." *Organic letters* 3.24 (2001): 3911-3914.

He et al., "Steroid hormones induce HMG1 overexpression and sensitize breast cancer cells to cisplatin and carboplatin." *Proceedings of the National Academy of Sciences* 97.11 (2000): 5768-5772.

Huang et al. "HMG-domain proteins specifically inhibit the repair of the major DNA adduct of the anticancer drug cisplatin by human excision nuclease," *Proceedings of the National Academy of Sciences* 91.22 (1994): 10394-10398.

International Preliminary Report on Patentability issued in International Application No. PCT/US15/35229, dated Dec. 22, 2016.

International Search Report and Written Opinion issued in International Application No. PCT/US15/35229, dated Sep. 14, 2015.

Kenny et al., "Platinum (IV) Prodrugs—A Step Closer to Ehrlich's Vision?." *European Journal of Inorganic Chemistry* 2017.12 (2017): 1596-1612.

Lemma et al., "Kinetics and mechanism for reduction of the anticancer prodrug trans, trans, trans-[PtCl2 (OH) 2 (c-C6H11NH2)(NH3)](JM335) by thiols." *Inorganic chemistry* 39.8 (2000): 1728-1734.

Mever et al., "Platinum (IV) complexes with chelating N-heterocyclic carbene ligands", *Organometal.*, 29:3392-3396, 2010.

Nemirovski et al. "New reduction pathways for ctc-[PtCl 2 (CH 3 CO 2) 2 (NH 3)(Am)] anticancer prodrugs." *Chemical Communications* 46.11 (2010): 1842-1844.

Novohradsky et al. "Antitumor platinum (IV) derivatives of oxaliplatin with axial valproate ligands." *Journal of inorganic biochemistry* 140 (2014): 72-79.

Office Action issued in corresponding Japanese Pat Appl. No. 2016-572508, dated Feb. 20, 2019.

Preihs et al., "Recent developments in texaphyrin chemistry and drug discovery", *Inorg. Chem.*, 52(21):12184-12192, 2013.

Romero-Canelón and Sadler. "Next-generation metal anticancer complexes: multitargeting via redox modulation." *Inorganic chemistry* 52.21 (2013): 12276-12291.

Rosenberg et al., "Inhibition of cell division in *Escherichia coli* by electrolysis products from a platinum electrode." *Nature* 205.4972 (1965): 698-699.

Search Report and Written Opinion issued in Singapore Application No. 11201610306R, dated Oct. 6, 2017.

Shi et al., "Pt (IV) complexes as prodrugs for cisplatin." *Journal of inorganic biochemistry* 107.1 (2012): 6-14.

Shimanovich et al. "Mn (II)—Texaphyrin as a Catalyst for the Decomposition of Peroxynitrite." *Journal of the American Chemical Society* 123.15 (2001): 3613-3614.

Thiabaud et al. "Activation of Platinum (IV) Prodrags By Motexafin Gadolinium as a Redox Mediator." *Angewandte Chemie* 128.41 (2016): 12816-12821.

Thiabaud et al. "Photoinduced Reduction of PtIV within an AntiProliferative PtIV-Texaphyrin Conjugate." *Chemistry—A European Journal* 20.29 (2014): 8942-8947.

Thiabaud et al., "Synthesis of new platinum(IV)-texaphvrin conjugates and studies of their anticancer activities", Poster Presentation at International Conference on BioInorganic Chemistry (ICBIC 16), Jul. 25, 2013.

Wei et al., Gadolinium texaphyrin-methotrexate conjugates. Towards improved cancer chemotherapeutic agents. *Org. Biomol. Chem.*, Aug. 4, 2005, vol. 3, pp. 3290-3296.

Wexselblatt and Gibson. "What do we know about the reduction of Pt (IV) pro-drugs?." *Journal of inorganic biochemistry* 117 (2012): 220-229.

Wexselblatt et al. "On the Stability of PtIV Pro-Drugs with Haloacetato Ligands in the Axial Positions." *Chemistry—A European Journal* 21.7 (2015): 3108-3114.

Wexselblatt et al., "Cellular interactions of platinum drugs." *Inorganica Chimica Acta* 393 (2012): 75-83.

(56) References Cited

OTHER PUBLICATIONS

Yap et al., "Finely Tuned Asymmetric Platinum (IV) Anticancer Complexes: Structure-Activity Relationship and Application as Orally Available Prodrugs." *ChemMedChem* 12.4 (2017): 300-311.
Zhang et al. "Facile Preparation of Mono-, Di-and Mixed-Carboxylato Platinum (IV) Complexes for Versatile Anticancer Prodrug Design." *Chemistry—a European Journal* 19.5 (2013): 1672-1676.
Zhang et al. "Pt (IV) analogs of oxaliplatin that do not follow the expected correlation between electrochemical reduction potential and rate of reduction by ascorbate." *Chemical Communications* 48.6 (2012): 847-849.
Zheng et al. "Encapsulation of Pt (IV) prodrags within a Pt (II) cage for drug delivery." *Chemical science* 6.2 (2015): 1189-1193.
Zhu et al., *Chem. Int. Ed.*, 53:13225, 2014.
Office Action issued in corresponding Japanese Pat. Appl. No. 2021-032438, dated Feb. 14, 2022. English Translation.

\* cited by examiner

FIG. 6A-C

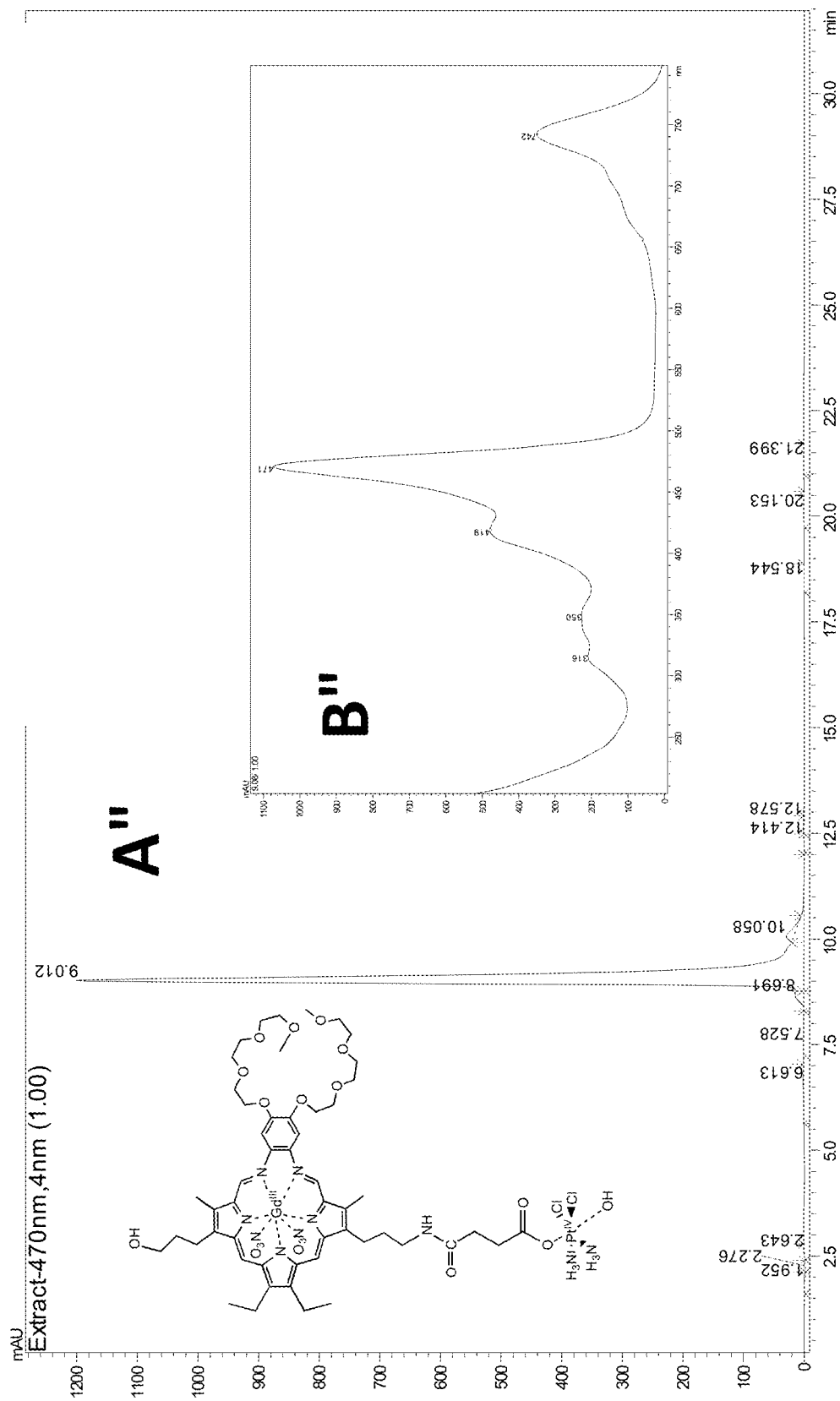
FIGS. 8A & B

A
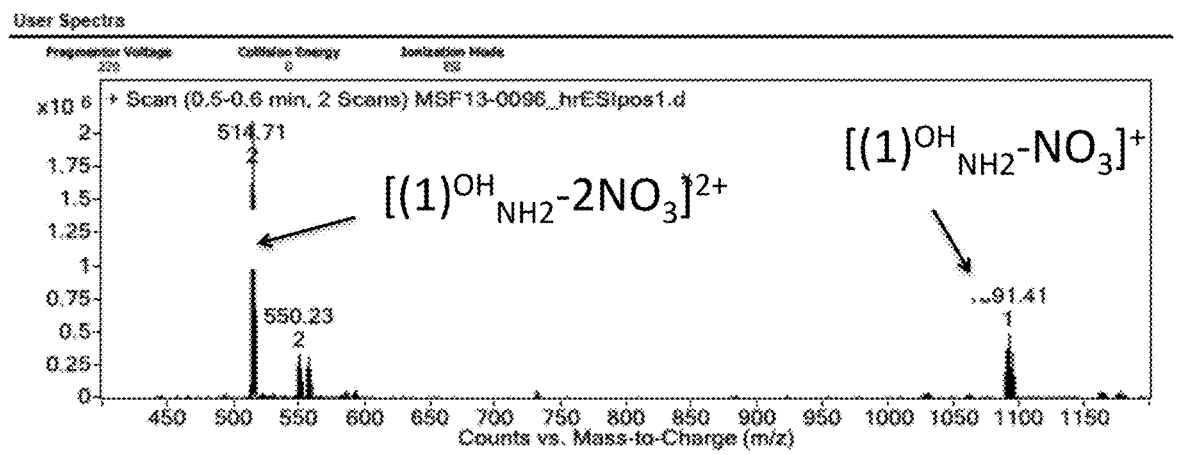
B
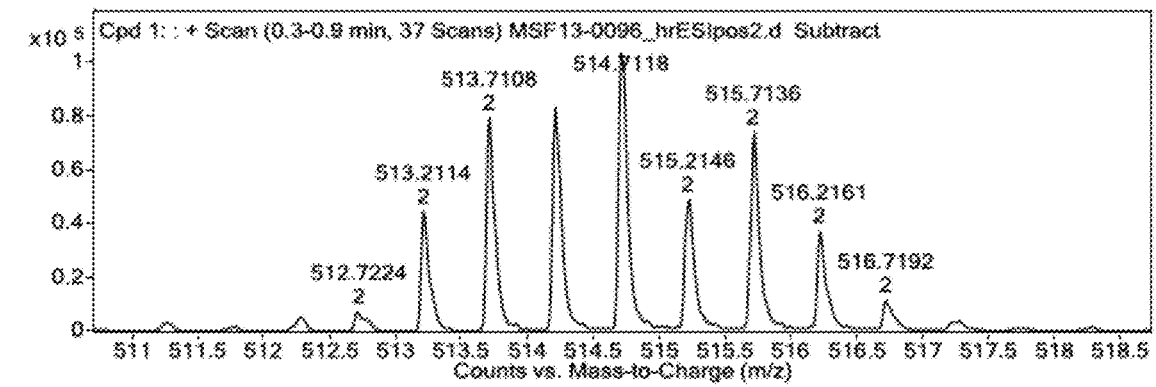
FIGS. 9A & B

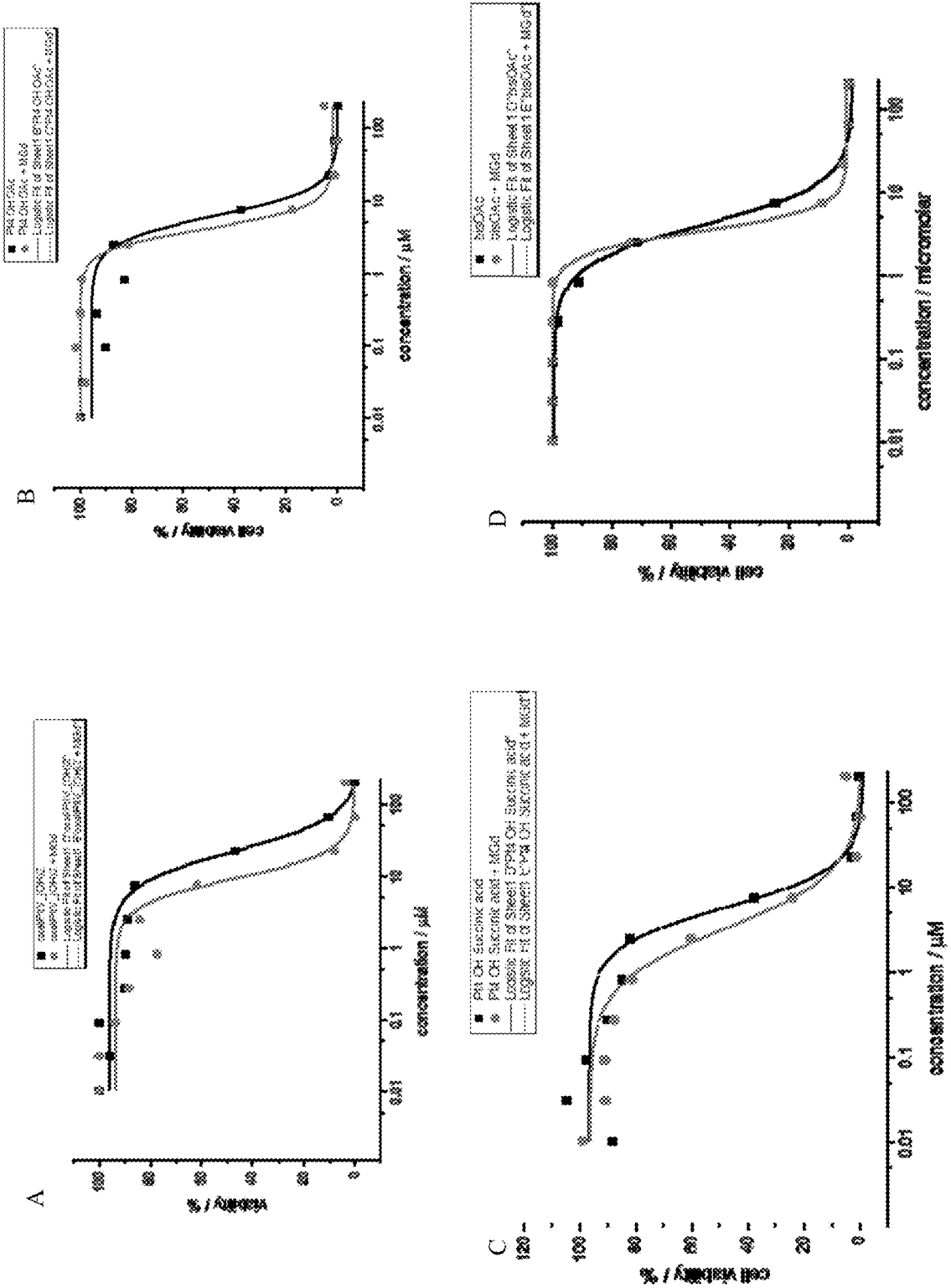
FIG. 35A-D

TEXAPHYRIN-PT(IV) CONJUGATES AND COMPOSITIONS FOR USE IN OVERCOMING PLATINUM RESISTANCE

This application is a continuation of U.S. application Ser. No. 15/317,560, filed Dec. 9, 2016, as a national phase application under 35 U.S.C. § 371 of International Application No. PCT/US2015/035229, filed Jun. 11, 2015, which claims the benefit of priority to U.S. Provisional Application Ser. No. 62/010,841, filed on Jun. 11, 2014, and Ser. No. 62/135,502, filed on Mar. 19, 2015, the entire contents of each of which are incorporated herein by reference.

This invention was made with government support under Grant Numbers CA160687 and CA068682 awarded by the National Institutes of Health. The government has certain rights in the invention.

BACKGROUND OF THE INVENTION

1. Field of the Invention

The present disclosure relates generally to the fields of medicine, pharmaceutical agents, and chemotherapeutics. The present disclosure relates to texaphyrin conjugates and compositions, which can be used to treat cancer.

2. Description of Related Art

The use of platinum(IV) chemotherapeutic pro-drugs has several advantages over the use of platinum(II) chemotherapeutic agents including improved stability, diminished side effects, or increased kinetic inertness (Rosenberg, B. et al., Nature 205:698, 1965; Shi, Y. et al., Biochem. 107:6, 2012). While, these pro-drug formulations are potentially useful, in order to increase pharmaceutical activity, the compound must be activated by reduction to the cytotoxic platinum(II) complex to obtain high cytotoxicity. Activation is typically carried out by intracellular processes, photoreduction, or through the use of ligands activated under specific conditions (Elding, L. I. and Gustafson, L., Inorg. Chim. Acta 19:165, 1976; Davies, M.S. et al., Inorg. Chem. 47:7673, 2008; Drougge, L. and Elding, L. I., Inorg. Chim. Acta 121:175, 1986; Lemma, K. et al., Inorg. Chem. 39:1728, 2000; Huang, J. C. et al., Proc. Natl. Acad. Sci. USA 1:10394-10398, 1994; Chau, K. Y. et al., Exp. Cell Res. 241:269-272, 1998; He, Q. et al., Proc. Natl. Acad. Sci. USA, 97:5768-5772, 2000; Barnes, K. R. et al., J. Chem. Biol. 11:557, 2004). Unfortunately, these processes rely on other cellular processes or application of external stimuli, such as light, and typically must be optimized to obtain effective results. Furthermore, many of these activation methods lack specificity for cancer cells.

The limitations found in FDA approved platinum(II) agents, which are often unable to overcome pharmacologic and molecular mechanisms in resistant cancers, have provided an incentive to use texaphyrins to help localize platinum(II) drugs to cancer sites via formation of so-called texaphyrin conjugates as detailed in U.S. Pat. No. 6,207,660, incorporated herein by reference. However, the prior art agents described in U.S. Pat. No. 6,207,660 and subsequent reports (Arambula, et al. 2009; Arambula, J. F.; Siddik, Z.; et al. 2011; Arambula, J. F.; Preihs, C. et al. 2011; Arambula, et al. 2012), proved unsatisfactory, either because the compounds lacked appropriate stability features, did not display appropriate solubility profiles, or failed to overcome completely platinum resistance in platinum resistant cell lines. Moreover, these prior texaphyrin-based systems relied on the use of a conjugated Pt(II) center rather than a Pt(IV) species. Thus, these conjugates did not benefit from the advantages associated with the use of a Pt(IV) center, including improved stability, diminished side effects, or increased kinetic inertness, as enunciated above. Developing new texaphyrin-platinum(IV) therapeutic agents or compositions that overcome these recognized limitations, while still providing an appropriate activation mechanism, would be of pharmaceutical importance; it would provide inter alfa improved treatments for cancers and be especially advantageous in treating those cancers that exhibit resistance to current Pt(II) and Pt(IV) chemotherapeutic agents.

As can be clearly seen, the development of new therapeutic agents and compositions containing a texaphyrin and a platinum(IV) complex are needed.

SUMMARY OF THE INVENTION

In some aspects, the present disclosure provides compounds of the formula:

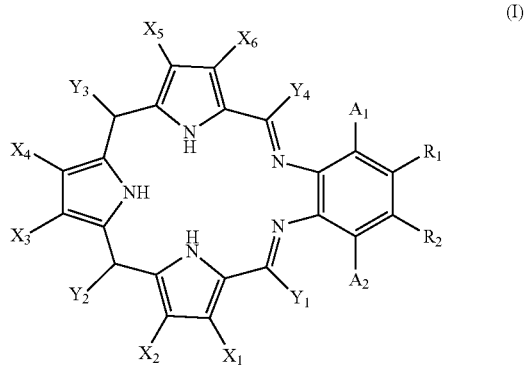

(I)

wherein:
R$_1$ and R$_2$ are each independently selected from hydrogen, halo, hydroxy, amino, mercapto, alkoxy$_{(C≤12)}$, substituted alkoxy$_{(C≤12)}$, or

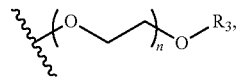

wherein n is 1-20 and R$_3$ is hydrogen, alkyl$_{(C≤6)}$, or substituted alkyl$_{(C≤6)}$, or a platinum(IV) chelating group;
A$_1$ and A$_2$ are each independently selected from hydrogen, halo, hvdroxy, alkvyl$_{(C≤12)}$, substituted alkyl$_{(C≤12)}$, alkoxy$_{(C≤12)}$, substituted alkoxy$_{(C≤12)}$, or

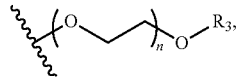

wherein n is 1-20 and R$_3$ is hydrogen, alkyl$_{(C≤6)}$, or substituted alkyl$_{(C≤6)}$, or a platinum(IV) chelating group;
Y$_1$, Y$_2$, Y$_3$, and Y$_4$ are each independently selected from hydrogen, halo, alkyl$_{(C≤12)}$, aryl$_{(C≤12)}$, substituted alkyl$_{(C≤12)}$, or substituted aryl$_{(C≤12)}$;
X$_1$, X$_2$, X$_3$, X$_4$, X$_5$, and X$_6$ are each independently selected from hydrogen, hydroxy, halo, amino, carboxy, nitro, or cyano, alkyl$_{(C\leq12)}$, alkenyl$_{(C\leq12)}$, alkynyl$_{(C\leq12)}$, aryl$_{(C\leq12)}$, aralkyl$_{(C\leq12)}$, acyl$_{(C\leq12)}$, amido$_{(C\leq12)}$, or a substituted version of any of these groups, or a platinum(IV) chelating group;

provided that at least one of $X_1$, $X_2$, $X_3$, $X_4$, $X_5$, and $X_6$ is a platinum(IV) chelating group; or an oxidized metal complex, a pharmaceutically acceptable salt, organometallic isomer, or tautomer thereof. In some embodiments, the compound is further defined as an oxidized metal complex with the formula:

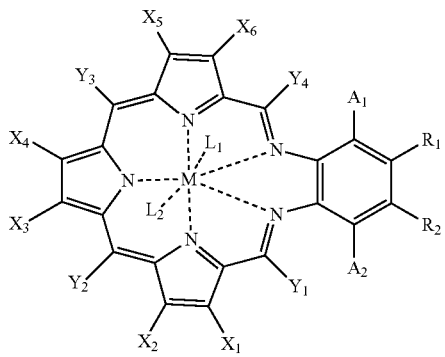

(II)

wherein: $R_1$, $R_2$, $A_1$, $A_2$, $Y_1$, $Y_2$, $Y_3$, $Y_4$, $X_1$, $X_2$, $X_3$, $X_4$, $X_5$, and $X_6$ are as defined above;

M is a monovalent metal ion, a divalent metal ion, or a trivalent metal ion; and $L_1$ and $L_2$ are each absent or anionic ligands independently selected from fluoride, chloride, bromide, carbonate, hydroxide, perchlorate, nitrate, sulfate, trifluoromethylsulfonate, acetylacetonate, acetate, or trifluoroacetate;

provided that when M is a monovalent metal ion then $L_1$ and $L_2$ are absent, and when M is a divalent metal ion, then $L_1$ or $L_2$ is absent;

or a pharmaceutically acceptable salt, organometallic isomer, or tautomer thereof. In some embodiments, the platinum(IV) chelating group is -$A_3$-$X_7$-$A_4$-$R_4$, wherein $A_3$ and $A_4$ are each independently alkanediyl$_{(C\leq12)}$, alkenediyl$_{(C\leq12)}$, arenediyl$_{(C\leq12)}$, alkoxydiyl$_{(C\leq12)}$, alkylaminodiyl$_{(C\leq12)}$, or a substituted version of any of these groups, $X_7$ is —O—, —S—, —NR$_5$—, —C(O)NR$_5$—, or NR$_5$C(O)—, wherein $R_5$ is hydrogen, alkyl$_{(C\leq6)}$, or substituted alkyl$_{(C\leq6)}$, and $R_4$ is amino, hydroxy, mercapto, carboxy, dicarboxy, or

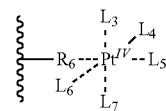

wherein:

$R_6$ is amino, hydroxy, mercapto, carboxy, or dicarboxy;

$L_3$, $L_4$, $L_5$, and $L_6$ are each ligands independently selected from aqua, ammonia, nitrate, sulfate, halide, hydroxide, phosphate, or glucose-6-phosphate, alkylamine$_{(C\leq12)}$, cycloalkylamine$_{(C\leq12)}$, dialkylamine$_{(C\leq18)}$, dicycloalkylamine$_{(C\leq18)}$, arylamine$_{(C\leq12)}$, diarylamine$_{(C\leq18)}$, diaminoalkane$_{(C\leq12)}$, diaminocycloalkane$_{(C\leq12)}$, diaminoarene$_{(C\leq12)}$, heteroarene$_{(C\leq12)}$, alkylcarboxylate$_{(C\leq12)}$, alkyldicarboxylate$_{(C\leq18)}$, arylcarboxylate$_{(C\leq12)}$, aryldicarboxylate$_{(C\leq18)}$, or a substituted version of any of these groups provided that $R_6$, $L_3$, $L_4$, $L_5$, and $L_6$ are appropriately charged to obtain a neutral complex. In some embodiments, the formula is further defined as:

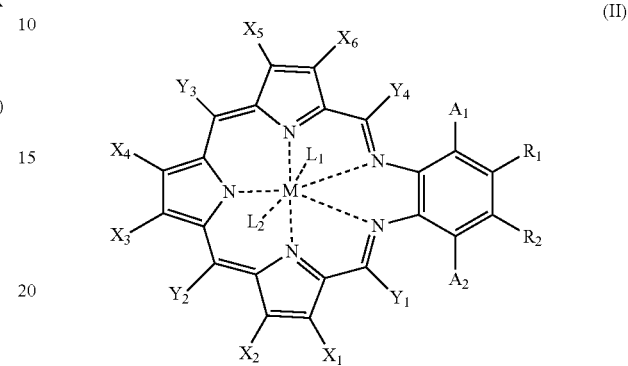

(II)

wherein:

$R_1$ and $R_2$ are each independently selected from hydrogen, halo, hydroxy, amino, mercapto, alkoxy$_{(C\leq12)}$, substituted alkoxy$_{(C\leq12)}$, or

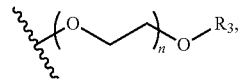

wherein n is 1-20 and $R_3$ is hydrogen, alkyl$_{(C\leq6)}$, or substituted alkyl$_{(C\leq6)}$, or a platinum(IV) chelating group;

$A_1$ and $A_2$ are each independently selected from hydrogen, halo, hydroxy, alkyl$_{(C\leq12)}$, substituted alkyl$_{(C\leq12)}$, alkoxy$_{(C\leq12)}$, substituted alkoxy$_{(C\leq12)}$, or

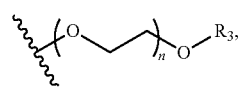

wherein n is 1-20 and $R_3$ is hydrogen, alkyl$_{(C\leq6)}$, or substituted alkyl$_{(C\leq6)}$, or a platinum(IV) chelating group;

$Y_1$, $Y_2$, $Y_3$, and $Y_4$ are each independently selected from hydrogen, halo, alkyl$_{(C\leq12)}$, or substituted alkyl$_{(C\leq12)}$;

$X_1$, $X_2$, $X_3$, $X_4$, $X_5$, and $X_6$ are each independently selected from hydrogen, hydroxy, halo, amino, carboxy, nitro, or cyano, alkyl$_{(C\leq12)}$, alkenyl$_{(C\leq12)}$, aryl$_{(C\leq12)}$, or a substituted version of any of these groups, or a platinum chelating group of the formula: -$A_3$-$X_7$-$A_4$-$R_4$, wherein $A_3$ and $A_4$ are each independently alkanediyl$_{(C\leq12)}$, alkoxydiyl$_{(C\leq12)}$, alkylaminodiyl$_{(C\leq12)}$, or a substituted version of any of these groups, $X_7$ is —NR$_5$—, —C(O)NR$_5$—, or —NR$_5$C(O)—, wherein $R_5$ is hydrogen, alkyl$_{(C\leq12)}$, or substituted alkyl$_{(C\leq12)}$, and $R_4$ is hydroxy, carboxy, dicarboxy, or

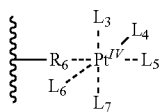

wherein:
R$_6$ is amino, hydroxy, mercapto, carboxy, or dicarboxy;
L$_3$, L$_4$, L$_5$, and L$_6$ are each ligands independently selected from aqua, ammonia, halide, or hydroxide,
diaminoalkane$_{(C \leq 12)}$, diaminocycloalkane$_{(C \leq 12)}$, diaminoarene$_{(C \leq 12)}$, alkyldicarboxylate$_{(C \leq 18)}$, aryldicarboxylate$_{(C \leq 18)}$, or a substituted version of any of these groups.

provided that at least one of X$_1$, X$_2$, X$_3$, X$_4$, X$_5$, and X$_6$ is a platinum(IV) chelating group;

M is a trivalent lanthanide metal ion; and

L$_1$ and L$_2$ are each anionic ligands independently selected from fluoride, chloride, bromide, perchlorate, nitrate, sulfate, trifluoromethylsulfonate, acetate, or trifluoroacetate;

or a pharmaceutically acceptable salt, organometallic isomer, or tautomer thereof. In some embodiments, the formula is further defined as:

(III)

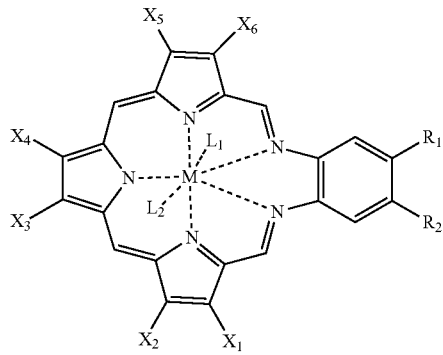

wherein:
R$_1$ and R$_2$ are each independently selected from hydroxy, alkoxy$_{(C \leq 12)}$, substituted alkoxy$_{(C \leq 12)}$, or

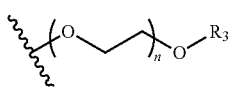

wherein n is 1-20 and R$_3$ is hydrogen, alkyl$_{(C \leq 6)}$, or substituted alkyl$_{(C \leq 6)}$;

or a pharmaceutically acceptable salt, organometallic isomer, or tautomer thereof. In some embodiments, the formula is further defined as:

(IV)

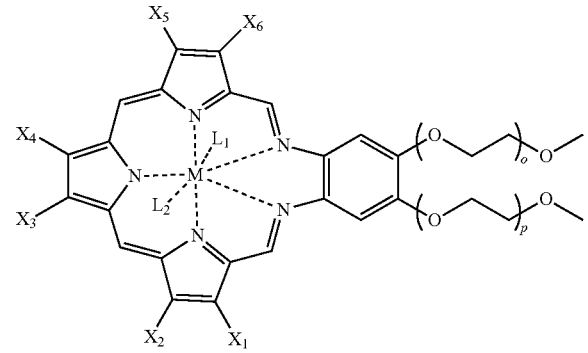

wherein:
o and p are each independently 1, 2, 3, 4, 5, or 6 or any range derivable therein;
X$_1$, X$_2$, X$_3$, X$_4$, X$_5$, and X$_6$ are each independently selected from hydrogen, hydroxy, or halo, alkyl$_{(C \leq 12)}$ or substituted alkyl$_{(C \leq 12)}$, or
a platinum chelating group of the formula: -A$_3$-X$_7$-A$_4$-R$_4$, wherein A$_3$ and A$_4$ are each independently alkanediyl$_{(C \leq 12)}$, alkoxydiyl$_{(C \leq 12)}$, or a substituted version of any of these groups, X$_7$ is —C(O)NR$_5$—, or —NR$_5$C(O)—, wherein R$_5$ is hydrogen, alkyl$_{(C \leq 12)}$, or substituted alkyl$_{(C \leq 12)}$, and R$_4$ is carboxy or

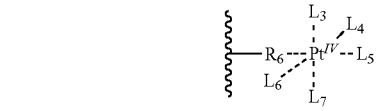

wherein:
R$_6$ is carboxy or dicarboxy;
L$_3$, L$_4$, L$_5$, and L$_6$ are each ligands independently selected from aqua, ammonia, halide, or hydroxide,
diaminoalkane$_{(C \leq 12)}$, diaminocycloalkane$_{(C \leq 12)}$, alkyldicarboxylate$_{(C \leq 18)}$, or a substituted version of any of these groups.

provided that at least one of X$_1$, X$_2$, X$_3$, X$_4$, X$_5$, and X$_6$ is a platinum(IV) chelating group;

M is a trivalent lanthanide metal ion; and

L$_1$ and L$_2$ are each anionic ligands independently selected from nitrate, acetate, or trifluoroacetate;

or a pharmaceutically acceptable salt, organometallic isomer, or tautomer thereof.

In some embodiments, o is 2, 3, or 4. In some embodiments, o is 3. In some embodiments, p is 2, 3, or 4. In some embodiments, p is 3.

In some embodiments, R$_1$ or R$_2$ is a platinum(IV) chelating group. In some embodiments, R$_2$ is a platinum(IV) chelating group of the formula:

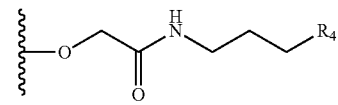

wherein: R$_4$ is as defined above. In some embodiments, X$_1$ is alkyl$_{(C \leq 12)}$ or substituted alkyl$_{(C \leq 12)}$. In some embodiments, $X_1$ is methyl. In some embodiments, $X_2$ is a platinum (IV) chelating group of the formula: -$A_3$-$X_7$-$A_4$-$R_4$, wherein $A_3$ and $A_4$ are each independently alkanediyl$_{(C \leq 12)}$, alkoxydiyl$_{(C \leq 12)}$, or a substituted version of any of these groups, $X_7$ is —C(O)NR$_5$— or NR$_5$C(O)—, wherein $R_5$ is hydrogen, alkyl$_{(C \leq 12)}$, or substituted alkyl$_{(C \leq 12)}$, and $R_4$ is carboxy, dicarboxy, or

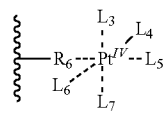

wherein: $R_6$ is carboxy or dicarboxy; $L_3$, $L_4$, $L_5$, and $L_6$ are each ligands independently selected from aqua, ammonia, halide, or hydroxide, diaminoalkane$_{(C \leq 12)}$, diaminocycloalkane$_{(C \leq 12)}$, alkyldicarboxylate$_{(C \leq 18)}$, or a substituted version of any of these groups.

In some embodiments, $A_3$ is alkanediyl$_{(C \leq 12)}$ or substituted alkanediyl$_{(C \leq 12)}$. In some embodiments, $A_3$ is alkanediyl$_{(C \leq 8)}$. In some embodiments, $A_3$ is —CH$_2$CH$_2$CH$_2$—. In some embodiments, $X_7$ is —C(O)NH— or —NHC(O)—. In some embodiments, $X_7$ is —NHC(O)—. In some embodiments, $A_4$ is alkanediyl$_{(C \leq 12)}$ or substituted alkanediyl$_{(C \leq 12)}$. In some embodiments, $A_4$ is alkanediyl$_{(C \leq 8)}$. In some embodiments, $A_4$ is —CH$_2$CH$_2$—. In some embodiments, $R_4$ is

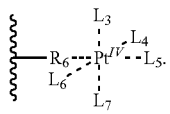

In some embodiments, $R_6$ is carboxy. In some embodiments, $L_3$ is halide, such as chloride. In some embodiments, $L_4$ is hydroxide. In some embodiments, $L_5$ is amino. In some embodiments, $L_6$ is halide, such as chloride. In some embodiments, $L_3$ and $L_6$ are taken together and are alkyldicarboxylate$_{(C \leq 18)}$. In some embodiments, $L_3$ and $L_6$ are —O$_2$CCO$_2$—. In some embodiments, $L_7$ is amino. In some embodiments, $L_5$ and $L_7$ are taken together and are diaminocycloalkane$_{(C \leq 12)}$. In some embodiments, $L_5$ and $L_7$ are each the amino group of 1,2-diaminocyclohexane.

In some embodiments, $X_3$ is alkyl$_{(C \leq 12)}$ or substituted alkyl$_{(C \leq 12)}$. In some embodiments, $X_3$ is alkyl$_{(C \leq 8)}$. In some embodiments, $X_3$ is ethyl. In some embodiments, $X_4$ is alkyl$_{(C \leq 12)}$ or substituted alkyl$_{(C \leq 12)}$. In some embodiments, $X_4$ is alkyl$_{(C \leq 8)}$. In some embodiments, $X_4$ is ethyl. In some embodiments, $X_5$ is alkyl$_{(C \leq 12)}$ or substituted alkyl$_{(C \leq 12)}$. In some embodiments, $X_5$ is substituted alkyl$_{(C \leq 8)}$. In some embodiments, $X_5$ is —CH$_2$CH$_2$CH$_2$OH. In some embodiments, $X_5$ is a platinum(IV) chelating group. In some embodiments, $X_6$ is alkyl$_{(C \leq 12)}$ or substituted alkyl$_{(C \leq 12)}$. In some embodiments, $X_6$ is alkyl$_{(C \leq 8)}$. In some embodiments, $X_6$ is methyl.

In some embodiments, M is gadolinium such as Gd(III). In some embodiments, $L_1$ is acetate or nitrate. In some embodiments, $L_2$ is acetate or nitrate.

In some embodiments, the compound is further defined as:

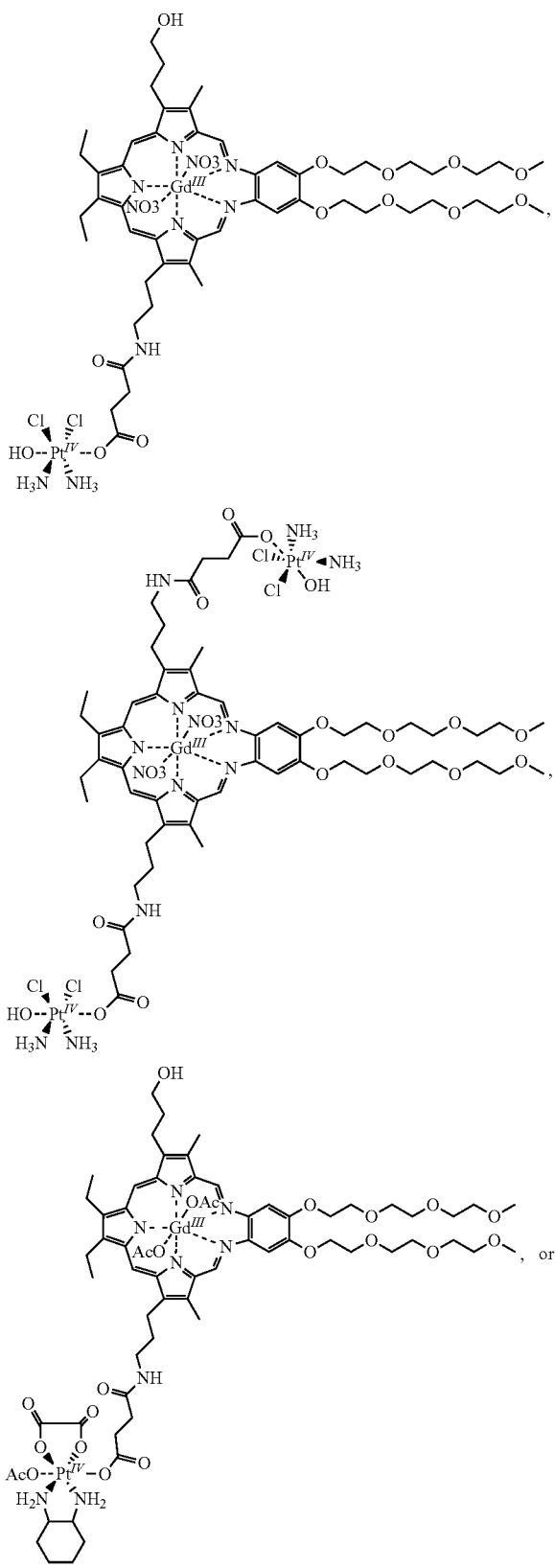

-continued

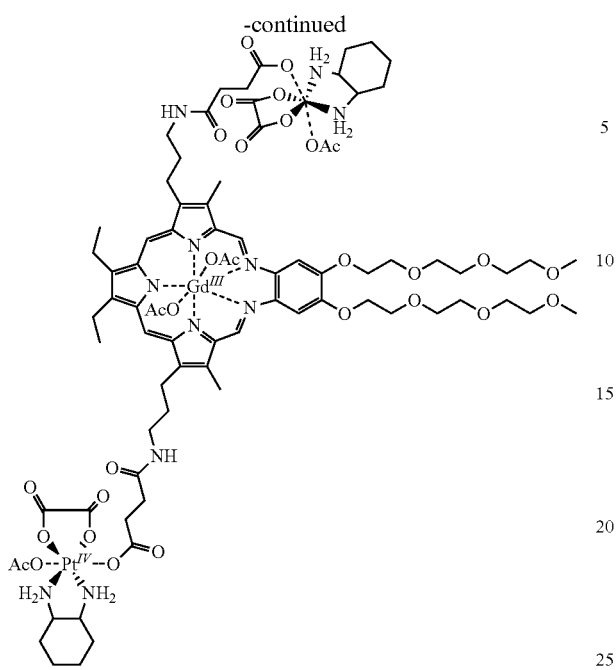

or a pharmaceutically acceptable salt, organometallic isomer, or tautomer thereof.

In yet another aspect, the present disclosure provides pharmaceutical compositions comprising:
 (A) a pharmaceutically acceptable carrier; and
 (B) a compound of the present disclosure.

In still yet another aspect, the present disclosure provides pharmaceutical compositions comprising:
 (A) a texaphyrin compound; and
 (B) a high oxidation state metal-containing chemotherapeutic complex.

In some embodiments, the metal in the high oxidation state metal-containing chemotherapeutic complex is selected from: gold, platinum, osmium, ruthenium, titanium, iron, cobalt, copper, iridium, gallium, arsenic, molybdenum, tin, rhodium, and lanthanum. The metal may be gold, osmium, platinum, ruthenium, or titanium. In some embodiments, the metal is osmium, platinum, or ruthenium. In some embodiments, the metal is platinum. In some embodiments, the high oxidation state metal-containing chemotherapeutic complex is a platinum(IV) complex. The platinum(IV) complex may have a formula:

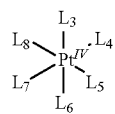
(VII)

wherein:
 $L_3$-$L_6$ are each independently selected from: hydroxide, water, nitrate, carbonyl, phosphate, sulfate, amine, halide, phosphine$_{(C \leq 24)}$, alkylcarboxylate$_{(C \leq 12)}$, cycloalkylcarboxylate$_{(C \leq 12)}$, alkyl carbamate$_{(C \leq 12)}$, cyclalkyl carbamate$_{(C \leq 12)}$, alkoxide$_{(C \leq 12)}$, aryloxide$_{(C \leq 12)}$, alkylamine$_{(C \leq 12)}$, cycloalkylamine$_{(C \leq 12)}$, dialkylamine$_{(C \leq 12)}$, dicycloalkylamine$_{(C \leq 12)}$, heterocycloalkane$_{(C \leq 12)}$, heteroarene$_{(C \leq 12)}$, or a substituted version of any of these groups; or a divalent ligand wherein two or more of $L_3$-$L_6$ are taken together and wherein each $L_3$-$L_6$ variable is a chelating group selected from: hydroxide, amine, alkylcarboxylate$_{(C \leq 12)}$, cycloalkylcarboxylate$_{(C \leq 12)}$, alkylcarbamate$_{(C \leq 12)}$, cycloalkylcarbamate$_{(C \leq 12)}$, alkoxide$_{(C \leq 12)}$, aryloxide$_{(C \leq 12)}$, alkylamine$_{(C \leq 12)}$, cycloalkylamine$_{(C \leq 12)}$, dialkylamine$_{(C \leq 12)}$, dicycloalkylamine$_{(C \leq 12)}$, heterocycloalkane$_{(C \leq 12)}$, or heteroarene$_{(C \leq 12)}$, or a substituted version of any of these groups; and joined together to the one or more other $L_3$-$L_6$ variables by a linking group selected from: a covalent bond, an alkanediyl$_{(C \leq 12)}$, an alkenediyl$_{(C \leq 12)}$, an arenediyl$_{(C \leq 12)}$, a heteroarenediyl$_{(C \leq 12)}$, or a heterocycloalkanediyl$_{(C \leq 12)}$ wherein the linking group replaces one or more hydrogens from the chelating group provided that $L_3$-$L_6$ have a total charge of −4. In some embodiments, $L_3$ or $L_6$ is hydroxide, alkylcarboxylate$_{(C \leq 8)}$ or substituted alkylcarboxylate$_{(C \leq 8)}$. In other embodiments, $L_3$ or $L_6$ is hydroxide. In other embodiments, $L_3$ and $L_6$ are hydroxide. In some embodiments, the platinum(IV) complex is satraplatin or LA-12. In other embodiments, the platinum(IV) complex is a platinum(IV) analogue of cisplatin, carboplatin, oxaliplatin, lobaplatin, nedaplatin, heptaplatin, picoplatin, or BBR$_{3464}$. In some embodiments, the platinum(IV) complex is a platinum(IV) analogue of cisplatin, carboplatin, or oxaliplatin. In some embodiments, the platinum(IV) complex is of the formula:

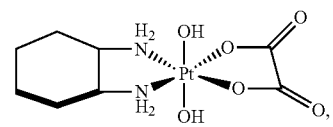

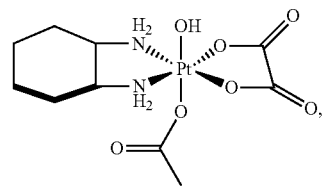

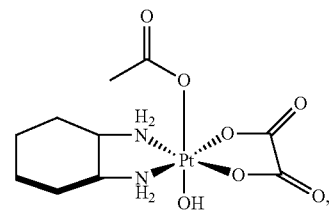

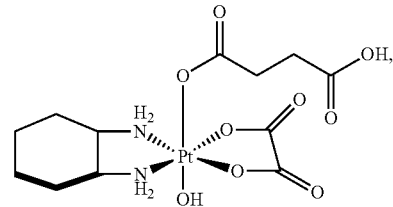

-continued

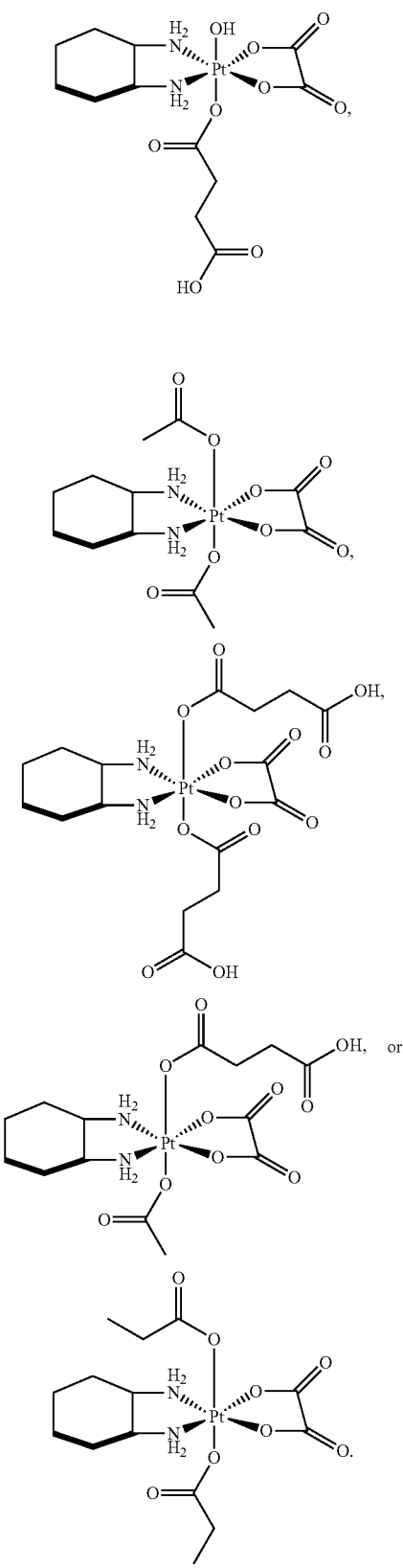

In some embodiments, the texaphyrin compound is of the formula:

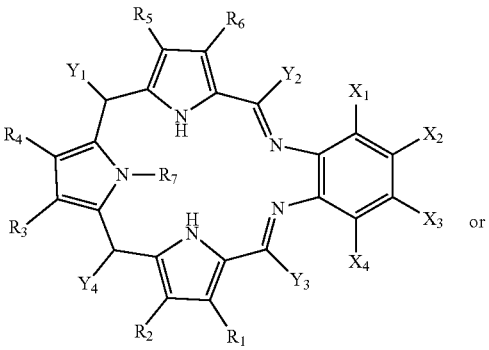

(V)

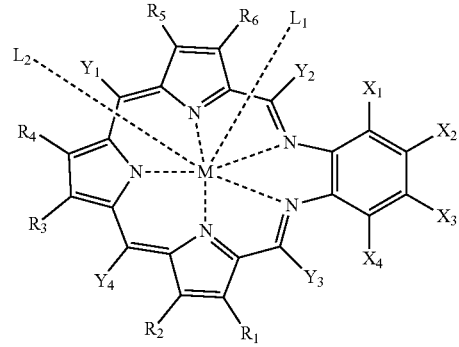

(VI)

wherein:
$Y_1$-$Y_4$ are each independently selected from: hydrogen, amino, cyano, halo, hydroxy, or hydroxyamino, alkyl$_{(C\leq12)}$, cycloalkyl$_{(C\leq12)}$, alkenyl$_{(C\leq12)}$, cycloalkenyl$_{(C\leq12)}$, alkynyl$_{(C\leq12)}$, aryl$_{(C\leq12)}$, aralkyl$_{(C\leq12)}$, heteroaryl$_{(C\leq12)}$, heterocycloalkyl$_{(C\leq12)}$, acyl$_{(C\leq12)}$, alkoxy$_{(C\leq12)}$, acyloxy$_{(C\leq12)}$, aryloxy$_{(C\leq12)}$, heteroaryloxy$_{(C\leq12)}$, heterocycloalkoxy$_{(C\leq12)}$, amido$_{(C\leq12)}$, alkylamino$_{(C\leq12)}$, dialkylamino$_{(C\leq12)}$, alkylthio$_{(C\leq12)}$, arylthio$_{(C\leq12)}$, alkylsulfinyl$_{(C\leq12)}$, arylsulfinyl$_{(C\leq12)}$, alkylsulfonyl$_{(C\leq12)}$, arylsulfonyl$_{(C\leq12)}$, or a substituted version of any of these groups; or
$R_1$-$R_6$ are each independently selected from: hydrogen, amino, cyano, halo, hydroxy, hydroxyamino, or nitro, alkyl$_{(C\leq12)}$, cycloalkyl$_{(C\leq12)}$, alkenyl$_{(C\leq12)}$, cycloalkenyl$_{(C\leq12)}$, alkynyl$_{(C\leq12)}$, aryl$_{(C\leq12)}$, aralkyl$_{(C\leq12)}$, heteroaryl$_{(C\leq12)}$, heterocycloalkyl$_{(C\leq12)}$, acyl$_{(C\leq12)}$, alkoxy$_{(C\leq12)}$, acyloxy$_{(C\leq12)}$, aryloxy$_{(C\leq12)}$, heteroaryloxy$_{(C\leq12)}$, heterocycloalkoxy$_{(C\leq12)}$, amido$_{(C\leq12)}$, alkylamino$_{(C\leq12)}$, dialkylamino$_{(C\leq12)}$, or a substituted version of any of these groups; or
a PEG moiety wherein the PEG moiety is of the formula: —(OCH$_2$CH$_2$)$_n$OR$_8$; wherein:
n is 1-20; and
$R_8$ is hydrogen, alkyl$_{(C\leq8)}$, or substituted alkyl$_{(C\leq8)}$;
$R_7$ is hydrogen, alkyl$_{(C\leq8)}$, cycloalkyl$_{(C\leq8)}$, alkenyl$_{(C\leq8)}$, cycloalkenyl$_{(C\leq8)}$, alkynyl$_{(c<s)}$, alkoxy$_{(C\leq8)}$, or a substituted version of any of these groups, or
an amino protecting group;
$X_1$-$X_4$ are each independently selected from: hydrogen, amino, cyano, halo, hydroxy, hydroxyamino, or nitro, alkyl$_{(C≤12)}$, cycloalkyl$_{(C≤12)}$, alkenyl$_{(C≤12)}$, cycloalkenyl$_{(C≤12)}$, alkynyl$_{(C≤12)}$, aryl$_{(C≤12)}$, aralkyl$_{(C≤12)}$, heteroaryl$_{(C≤12)}$, heterocycloalkyl$_{(C≤12)}$, acyl$_{(C≤12)}$, alkoxy$_{(C≤12)}$, acyloxy$_{(C≤12)}$, aryloxy$_{(C≤12)}$, heteroaryloxy$_{(C≤12)}$, heterocycloalkoxy$_{(C≤12)}$, amido$_{(C≤12)}$, alkylamino$_{(C≤12)}$, dialkylamino$_{(C≤12)}$, or a substituted version of any of these groups; or a PEG moiety wherein the PEG moiety is of the formula: (OCH$_2$CH$_2$)$_n$OR$_8$; wherein:

n is 1-20; and

R$_8$ is hydrogen, alkyl$_{(C≤8)}$, or substituted alkyl$_{(C≤8)}$;

L$_1$ and L$_2$ are each independently absent, a neutral ligand, or an anionic ligand; and M is a metal ion;

provided that L$_1$ and L$_2$ are present or absent as appropriate to balance the charge on the metal ion;

or a pharmaceutically acceptable salt or tautomer thereof. In other embodiments, the texaphyrin is a compound of formula VB. In some embodiments, M is a transition metal in the +2 oxidation state or +3 oxidation state such as gadolinium(III). In some embodiments, the texaphyrin compound wherein at least two of X$_1$-X$_4$ are a PEG moiety wherein the PEG moiety is of the formula: —(OCH$_2$CH$_2$)$_n$OR$_8$; wherein: n is 1-20; and R$_8$ is hydrogen, alkyl$_{(C≤8)}$, or substituted alkyl$_{(C≤8)}$. In some embodiments, the texaphyrin compound has the following formula:

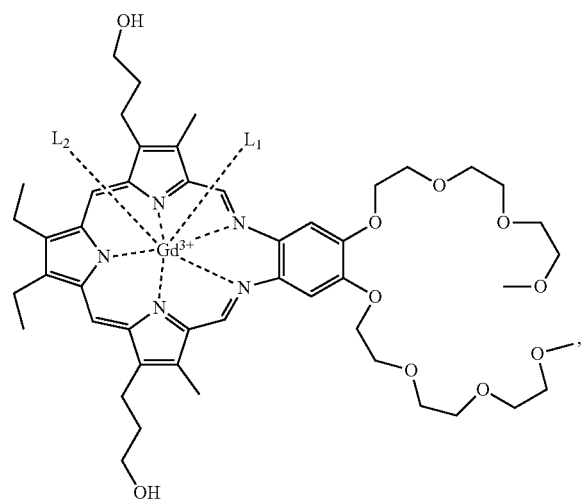

wherein:

L$_1$ and L$_2$ are each independently an anionic ligand; and or a pharmaceutically acceptable salt or tautomer thereof. In some embodiments, the texaphyrin compound is motexafin gadolinium. In some embodiments, the texaphyrin compound is a compound of formula I or formula II. In some embodiments, the texaphyrin and the high oxidation state metal-containing chemotherapeutic complex are administered in a ratio from about 10:1 to about 1:10. In some embodiments, the ratio is from about 3:1 to about 1:3. In some embodiments, the ratio is about 1:2.

In some embodiments, the pharmaceutical composition further comprises a reducing agent. The reducing agent may be sodium ascorbate, thioredoxin reductase, a biological thiol, a platinum(II) complex, or light. In some embodiments, the biological thiol is cysteine, homocysteine, or glutathione. In some embodiments, the pharmaceutical composition further comprises a pharmaceutically acceptable carrier. In some embodiments, the pharmaceutical composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctivally, subcutaneously, sublingually, topically, transbuccally, transdermally, vaginally, in crmes, in lipid compositions, via a catheter, via a lavage, via continuous infusion, via infusion, via inhalation, via injection, via local delivery, or via localized perfusion. In some embodiments, the pharmaceutical composition is formulated for oral or intravenous administration. In some embodiments, the composition is formulated as a unit dose.

In still yet another aspect, the present disclosure provides methods of treating a disease in a patient comprising administering to the patient in need thereof a therapeutically effective amount of:

(A) a compound or pharmaceutical composition of the present disclosure;

(B) a pharmaceutical composition of the present disclosure; or (C) a first agent selected from a texaphyrin compound and a second agent selected from a high oxidation state metal-containing chemotherapeutic complex.

In some embodiments, the disease is cancer, such as a carcinoma, sarcoma, lymphoma, leukemia, melanoma, mesothelioma, multiple myeloma, or seminoma or the cancer is of the bladder, blood, bone, brain, breast, central nervous system, cervix, colon, endometrium, esophagus, gall bladder, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In some embodiments, the cancer is ovarian cancer, testicular cancer, or bladder cancer. The ovarian cancer may be ovarian carcinoma. The cancer may be colon cancer or colorectal cancer. In some embodiments, the cancer is resistant to a metal chemotherapeutic. The cancer may be resistant to a platinum chemotherapeutic. In some embodiments, the cancer is resistant to cisplatin, carboplatin, or oxaliplatin.

In some embodiments, the methods comprise administering a compound or composition of the present disclosure. In some embodiments, the platinum complex is reduced in vivo to form an active complex. The compound may be localized to a tumor before the reduction of the platinum complex.

In some embodiments, the methods comprise administering a composition comprising a texaphyrin compound and high oxidation state metal-containing chemotherapeutic complex. The methods comprise administering a first agent selected from a texaphyrin compound and a second agent selected from a high oxidation state metal-containing chemotherapeutic complex. In some embodiments, the high oxidation state metal-containing chemotherapeutic complex is a metal-containing chemotherapeutic complex that is capable of undergoing reduction. The high oxidation state metal-containing chemotherapeutic complex may be in a pro-drug form. In some embodiments, the high oxidation state metal-containing chemotherapeutic complex is in an oxidized form and is reduced in vivo to form a chemotherapeutically more active species. In some embodiments, the high oxidation state metal-containing chemotherapeutic complex is activated in the presence of the texaphyrin compound. In some embodiments, the high oxidation state metal-containing chemotherapeutic complex is activated by a reduced form of the texaphyrin compound. In some embodiments, the reduced form of the texaphyrin compound is produced in vivo by one or more reducing species. The high oxidation state metal-containing chemotherapeutic complex may be preferentially activated in a cancer cell. The high oxidation state metal-containing chemotherapeutic complex may be preferentially activated in the presence of a cancer cell. In some embodiments, the texaphyrin compound localizes to a cancer cell and the high oxidation state metal-containing chemotherapeutic complex is preferentially activated by the texaphyrin compound in the cancer cell. In some embodiments, the texaphyrin compound localizes to the extracellular matrix around a cancer cell and the high oxidation state metal-containing chemotherapeutic complex is preferentially activated by the texaphyrin compound in the presence of the cancer cell. The high oxidation state metal-containing chemotherapeutic complex may be selectively activated in the cancer cell. The high oxidation state metal-containing chemotherapeutic complex may be selectively activated in the presence of the cancer cell.

In some embodiments, the metal in the high oxidation state metal-containing chemotherapeutic complex is selected from: gold, platinum, osmium, ruthenium, titanium, iron, cobalt, copper, iridium, gallium, arsenic, molybdenum, tin, rhodium, and lanthanum. In some embodiments, the metal is platinum. In some embodiments, the high oxidation state metal-containing chemotherapeutic complex is a platinum(IV) complex. The platinum(IV) complex may comprise one or more hydroxide ligands. The platinum(IV) complex may comprise two axial hydroxide ligands. In some embodiments, the platinum(IV) complex is of the formula:

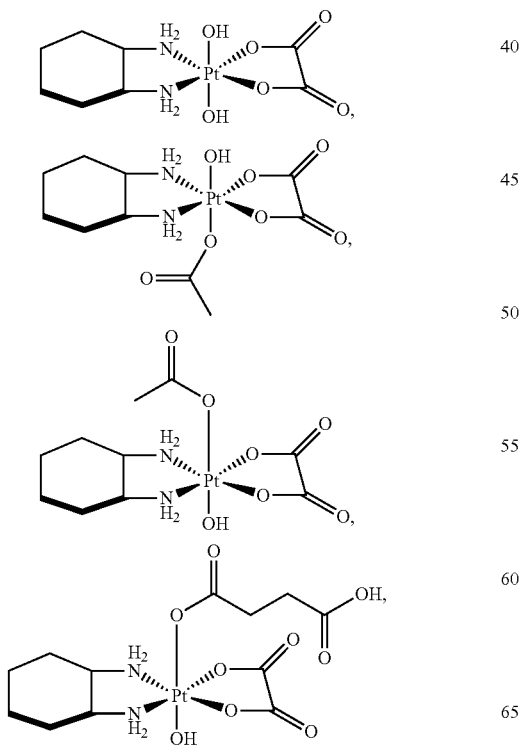

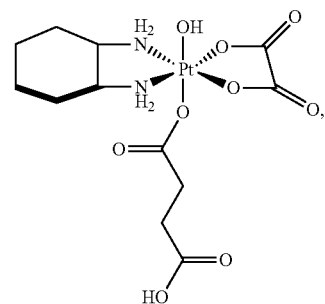

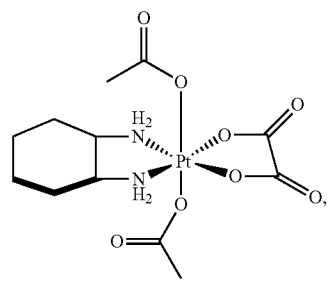

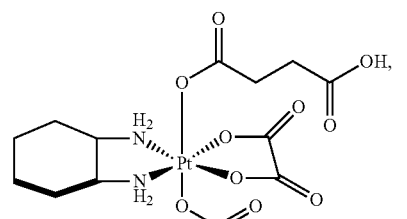

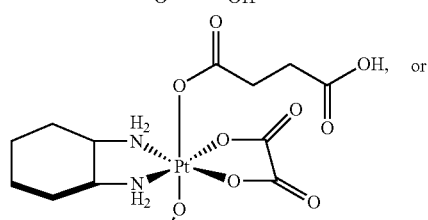

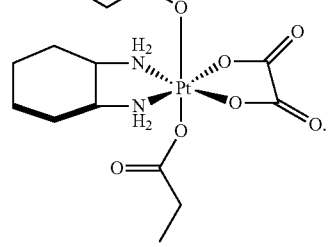

In some embodiments, the texaphyrin compound is of the formula:

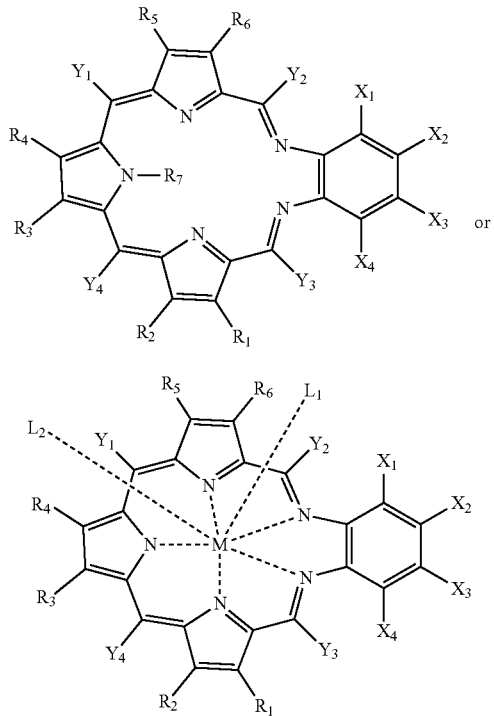

wherein:
$Y_1$-$Y_4$ are each independently selected from: hydrogen, amino, cyano, halo, hydroxy, or hydroxyamino,
alkyl$_{(C\leq 12)}$, cycloalkyl$_{(C\leq 12)}$, alkenyl$_{(C\leq 12)}$, cycloalkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heterocycloalkyl$_{(C\leq 12)}$, acyl$_{(C\leq 12)}$, alkoxy$_{(C\leq 12)}$, acyloxy$_{(C\leq 12)}$, aryloxy$_{(C\leq 12)}$, heteroaryloxy$_{(C\leq 12)}$, heterocycloalkoxy$_{(C\leq 12)}$, amido$_{(C\leq 12)}$, alkylamino$_{(C\leq 12)}$, dialkylamino$_{(C\leq 12)}$, alkylthio$_{(C\leq 12)}$, arylthio$_{(C\leq 12)}$, alkylsulfinyl$_{(C\leq 12)}$, arylsulfinyl$_{(C\leq 12)}$, alkylsulfonyl$_{(C\leq 12)}$, arylsulfonyl$_{(C\leq 12)}$, or a substituted version of any of these groups; or
$R_1$-$R_6$ are each independently selected from: hydrogen, amino, cyano, halo, hydroxy, hydroxyamino, or nitro, alkyl$_{(C\leq 12)}$, cycloalkyl$_{(C\leq 12)}$, alkenyl$_{(C\leq 12)}$, cycloalkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heterocycloalkyl$_{(C\leq 12)}$, acyl$_{(C\leq 12)}$, alkoxy$_{(C\leq 12)}$, acyloxy$_{(C\leq 12)}$, aryloxy$_{(C\leq 12)}$, heteroaryloxy$_{(C\leq 12)}$, heterocycloalkoxy$_{(C\leq 12)}$, amido$_{(C\leq 12)}$, alkylamino$_{(C\leq 12)}$, dialkylamino$_{(C\leq 12)}$, or a substituted version of any of these groups; or
a PEG moiety wherein the PEG moiety is of the formula: —(OCH$_2$CH$_2$)$_n$OR$_8$; wherein:
n is 1-20; and
$R_8$ is hydrogen, alkyl$_{(C\leq 8)}$, or substituted alkyl$_{(C\leq 8)}$;
$R_7$ is hydrogen,
alkyl$_{(C\leq 8)}$, cycloalkyl$_{(C\leq 8)}$, alkenyl$_{(C\leq 8)}$, cycloalkenyl$_{(C\leq 8)}$, alkynyl$_{(C\leq 8)}$, alkoxy$_{(C\leq 8)}$, or a substituted version of any of these groups, or
an amino protecting group;
$X_1$-$X_4$ are each independently selected from: hydrogen, amino, cyano, halo, hydroxy, hydroxyamino, or nitro, alkyl$_{(C\leq 12)}$, cycloalkyl$_{(C\leq 12)}$, alkenyl$_{(C\leq 12)}$, cycloalkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heterocycloalkyl$_{(C\leq 12)}$, acyl$_{(C\leq 12)}$, alkoxy$_{(C\leq 12)}$, acyloxy$_{(C\leq 12)}$, aryloxy$_{(C\leq 12)}$, heteroaryloxy$_{(C\leq 12)}$, heterocycloalkoxy$_{(C\leq 12)}$, amido$_{(C\leq 12)}$, alkylamino$_{(C\leq 12)}$, dialkylamino$_{(C\leq 12)}$, or a substituted version of any of these groups; or
a PEG moiety wherein the PEG moiety is of the formula: —(OCH$_2$CH$_2$)$_n$OR$_8$; wherein:
n is 1-20; and
$R_8$ is hydrogen, alkyl$_{(C\leq 8)}$, or substituted alkyl$_{(C\leq 8)}$;
$L_1$ and $L_2$ are each independently absent, a neutral ligand, or an anionic ligand; and
M is a metal ion, provided that $L_1$ and $L_2$ are absent or a neutral ligand as needed to balance the charge on the metal ion;
or a pharmaceutically acceptable salt or tautomer thereof. In some embodiments, the texaphyrin compound is of the formula:

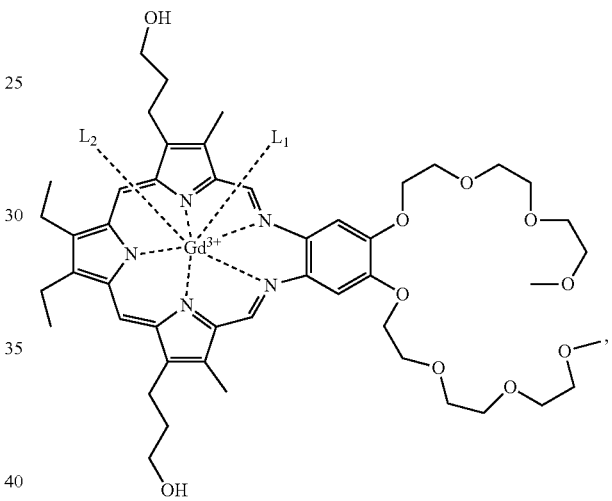

wherein:
$L_1$ and $L_2$ are each independently an anionic ligand; and
or a pharmaceutically acceptable salt or tautomer thereof. In some embodiments, the texaphyrin compound is motexafin gadolinium.

In some embodiments, the texaphyrin and the high oxidation state metal-containing chemotherapeutic complex are administered in a ratio from about 10:1 to about 1:10. In some embodiments, the texaphyrin and the high oxidation state metal-containing chemotherapeutic complex are administered together. In some embodiments, the texaphyrin or the high oxidation state metal-containing chemotherapeutic complex is administered and then the other is administered within a time period of 1 week, or the time period is 24 hours., or the time period is 12 hours.

In other embodiments, the texaphyrin is administered first and then the high oxidation state metal-containing chemotherapeutic complex is administered. In other embodiments, the high oxidation state metal-containing chemotherapeutic complex is administered first and then the texaphyrin is administered. In some embodiments, the texaphyrin is administered once. In other embodiments, the texaphyrin is administered two or more times. In some embodiments, the high oxidation state metal-containing chemotherapeutic complex is administered once. In other embodiments, the high oxidation state metal-containing chemotherapeutic complex is administered two or more times.

In some embodiments, the method further comprises administering a reducing agent. In some embodiments, the method is administered in conjunction with a second therapy, wherein the second therapy is a third chemotherapeutic drug, surgery, radiotherapy, photodynamic therapy, sonodynamic therapy, cryotherapy, or immunotherapy. In some embodiments, the third chemotherapeutic drug is bleomycin, doxorubicin, taxol, taxotere, etoposide, 4-OH cyclophosphamide, or 5-fluorouracil or the third chemotherapeutic drug is cisplatin, carboplatin, oxaliplatin, or a Pt(IV) complex.

In yet another aspect, the present disclosure provides methods of preparing a platinum-texaphyrin complex of the formula:

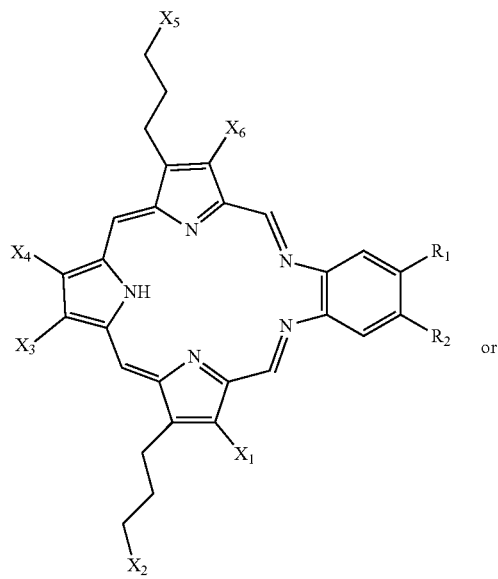

(VII)

or

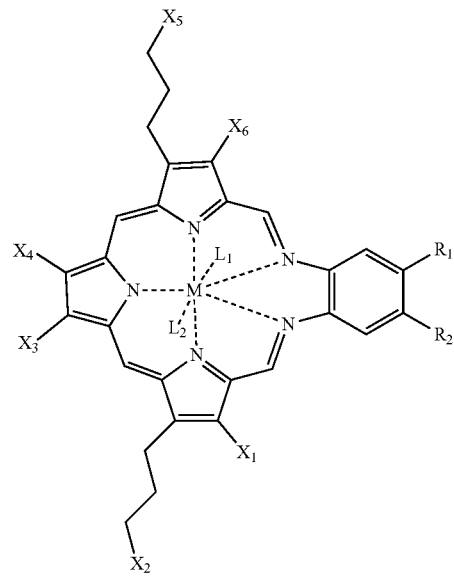

(VIII)

wherein:

$R_1$ and $R_2$ are each independently selected from hydrogen, halo, hydroxy, amino, mercapto, alkoxy$_{(C\leq12)}$, substituted alkoxy$_{(C\leq12)}$, or

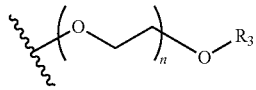

wherein n is 1-8 and $R_3$ is hydrogen, alkyl$_{(C\leq6)}$, or substituted alkyl$_{(C\leq6)}$;

$X_1$, $X_3$, $X_4$, and $X_6$ are each independently selected from hydrogen, hydroxy, halo, amino, carboxy, nitro, or cyano, alkyl$_{(C\leq12)}$, alkenyl$_{(C\leq12)}$, alkynyl$_{(C\leq12)}$, aryl$_{(C\leq12)}$, aralkyl$_{(C\leq12)}$, acyl$_{(C\leq12)}$, amido$_{(C\leq12)}$, or a substituted version of any of these groups, $X_2$ is

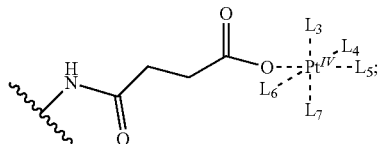

wherein:

$L_3$, $L_4$, $L_5$, and $L_6$ are each ligands independently selected from aqua, ammonia, nitrate, sulfate, halide, hydroxide, phosphate, or glucose-6-phosphate, alkylamine$_{(C\leq12)}$, cycloalkylamine$_{(C\leq12)}$, dialkylamine$_{(C\leq18)}$, dicycloalkylamine$_{(C\leq18)}$, arylamine$_{(C\leq12)}$, diarylamine$_{(C\leq18)}$, diaminoalkane$_{(C\leq12)}$, diaminocycloalkane$_{(C\leq12)}$, diaminoarene$_{(C\leq12)}$, heteroarene$_{(C\leq12)}$, alkylcarboxylate$_{(C\leq12)}$, alkyldicarboxylate$_{(C\leq18)}$, arylcarboxylate$_{(C\leq12)}$, aryldicarboxylate$_{(C\leq18)}$, or a substituted version of any of these groups;

$X_5$ are each independently selected from amino, hydroxy, alkoxy$_{(C\leq12)}$, substituted alkoxy$_{(C\leq12)}$, aralkoxy$_{(C\leq24)}$, or substituted aralkoxy$_{(C\leq24)}$, or

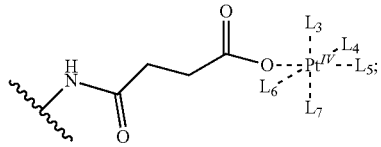

M is a metal ion; and $L_1$ and $L_2$ are each anionic ligands independently selected from fluoride, chloride, bromide, carbonate, hydroxide, perchlorate, nitrate, sulfate, trifluoromethylsulfonate, acetylacetonate, acetate, or trifluoroacetate;

provided that $L_1$ and $L_2$ are present or absent as necessary to balance the charge on M; comprising reacting a compound of the formula

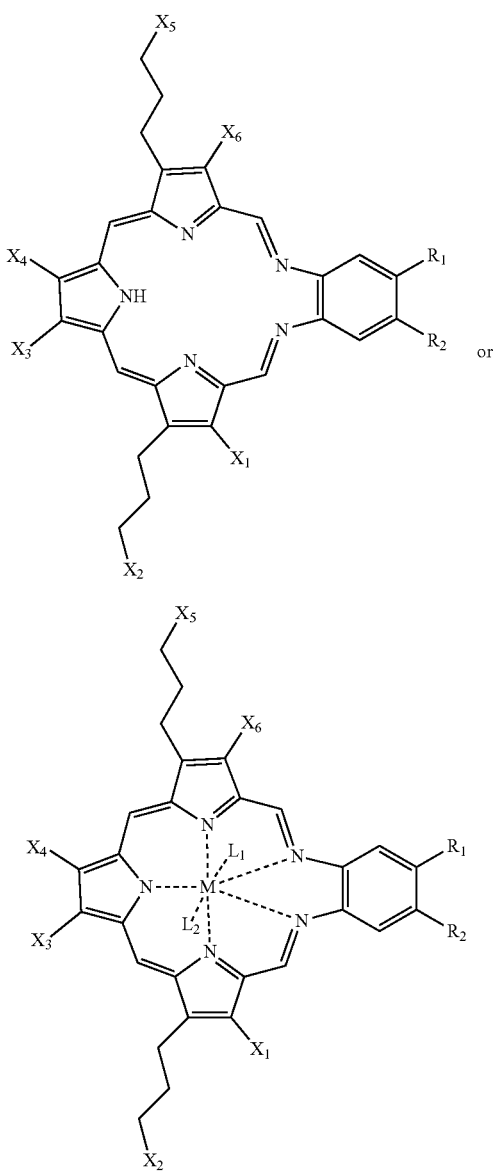

(VII)

(VIII)

wherein:
X$_2$ is amino;
X$_5$ is amino, hydroxy, alkoxy$_{(C≤12)}$, substituted alkoxy$_{(C≤12)}$, aralkoxy$_{(C≤24)}$, or substituted aralkoxy$_{(C≤24)}$; and
R$_1$, R$_2$, X$_1$, X$_3$, X$_4$, and X$_6$ are as defined above;
with a compound of the formula:

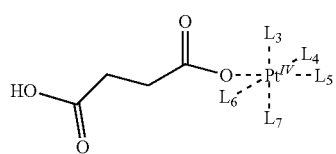

(VIII)

in a solvent and in the presence of an activating agent. In some embodiments, the solvent is an aqueous organic mixture, such as a water and acetonitrile mixture. In some embodiments, the activating agent is N-hydroxysuccinimide, 1-ethyl-3-(3-dimethylaminopropyl)carbodiimide (EDC), dicyclohexylcarbodiimide (DCC), diisopropylcarbodiimide (DIC), PyBOP, BOP, HOBT, or N,N'-carbonyldiimidazole (CDI). In some embodiments, the activating agent is a N-hydroxysuccinimide and 1-ethyl-3-(3-dimethylaminopropyl)carbodiimide.

It is contemplated that any method or composition described herein can be implemented with respect to any other method or composition described herein.

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a method, composition, kit, or system that "comprises," "has," "contains," or "includes" one or more recited steps or elements possesses those recited steps or elements, but is not limited to possessing only those steps or elements; it may possess (i.e., cover) elements or steps that are not recited. Likewise, an element of a method, composition, kit, or system that "comprises," "has," "contains," or "includes" one or more recited features possesses those features, but is not limited to possessing only those features; it may possess features that are not recited.

Any embodiment of any of the present methods, composition, kit, and systems may consist of or consist essentially of rather than comprise/include/contain/havethe described steps and/or features. Thus, in any of the claims, the term "consisting of" or "consisting essentially of" may be substituted for any of the open-ended linking verbs recited above, in order to change the scope of a given claim from what it would otherwise be using the open-ended linking verb.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 6B) stability (RP-HPLC analysis) of 4 in PBS solution in the dark (black circles) or exposed to laboratory light (black squares), The designation 1 indicates the hydrolysis phase (absence of light), while the 2 indicates the phase corresponding to light exposure; (FIG. 6C) quantification by FAAS (Pt) and by nanodrop (DNA) of the number of Pt-DNA adducts formed after reaction of 4 with DNA in the dark (black circles) or exposed to natural light (black squares).

FIGS. 8A & B show the RP-HPLC chromatogram monitoring at 470 nm (FIG. 8A) and UV-vis spectrum (FIG. 8B) of conjugate 4 studied in water.

FIGS. 9A & B show the high-resolution ESI-MS spectra of deprotected species 1(OH)(NH$_2$) after isolation using a C18 column. FIG. 9A: Entire spectrum; FIG. 9B: magnified view of the major peak with theoretical isotopic relative abundance also shown.

FIG. 11C shows the high resolution mass spectrum.

FIGS. 35A-35E show cell viability as a function of concentration with the texaphyrin compound and a platinum(IV) analogue of oxaliplatin (circles) compared with the platinum(IV) analogue alone (squares). A summary of the $IC_{50}$ values for these combinations is provided in Table 1. FIG. 35A shows the data for a platinum(IV) analogue wherein the axial ligands are both hydroxide. FIG. 35B shows the data for a platinum(IV) analogue wherein one of the axial ligands is hydroxide and the other is acetate. FIG. 35C shows the data for a platinum(IV) analog wherein one of the axial ligands is hydroxide and the other is succinate. FIG. 35D shows the data for a platinum(IV) analogue wherein the axial ligands are both acetate. FIG. 35E shows the data for a platinum(IV) analogue wherein the axial ligands are both ethanoate.

DESCRIPTION OF ILLUSTRATIVE EMBODIMENTS

Figure 1:
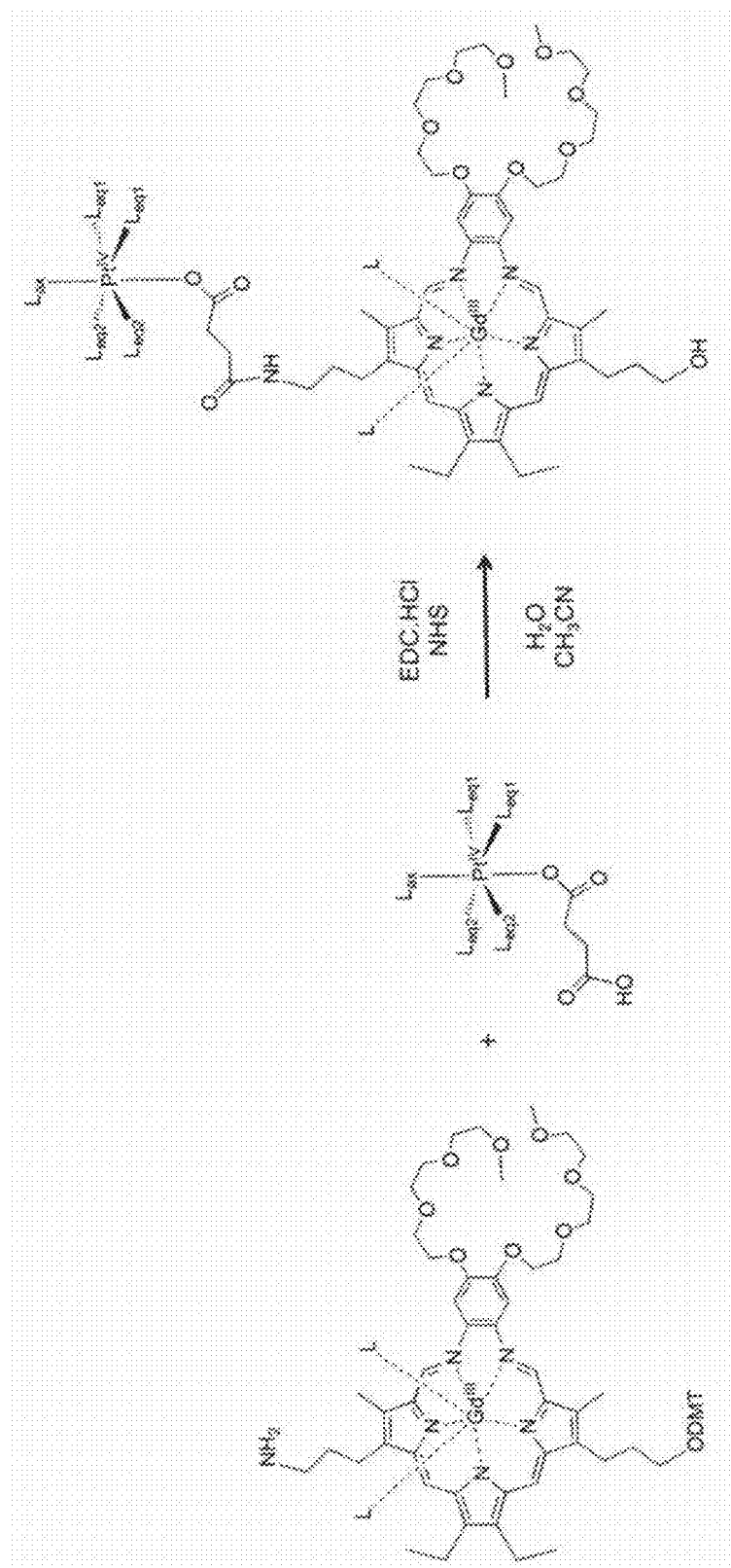
FIG. 1 shows a generalized synthesis scheme for preparation of new Pt(IV) texaphyrin analogues.

The present disclosure describes new compounds (FIG. 1) which can be used to treat cancer and in particular platinum resistance cancer lines as well as new composition comprising a texaphyrin compound and a platinum(IV) drug.

Figure 2:
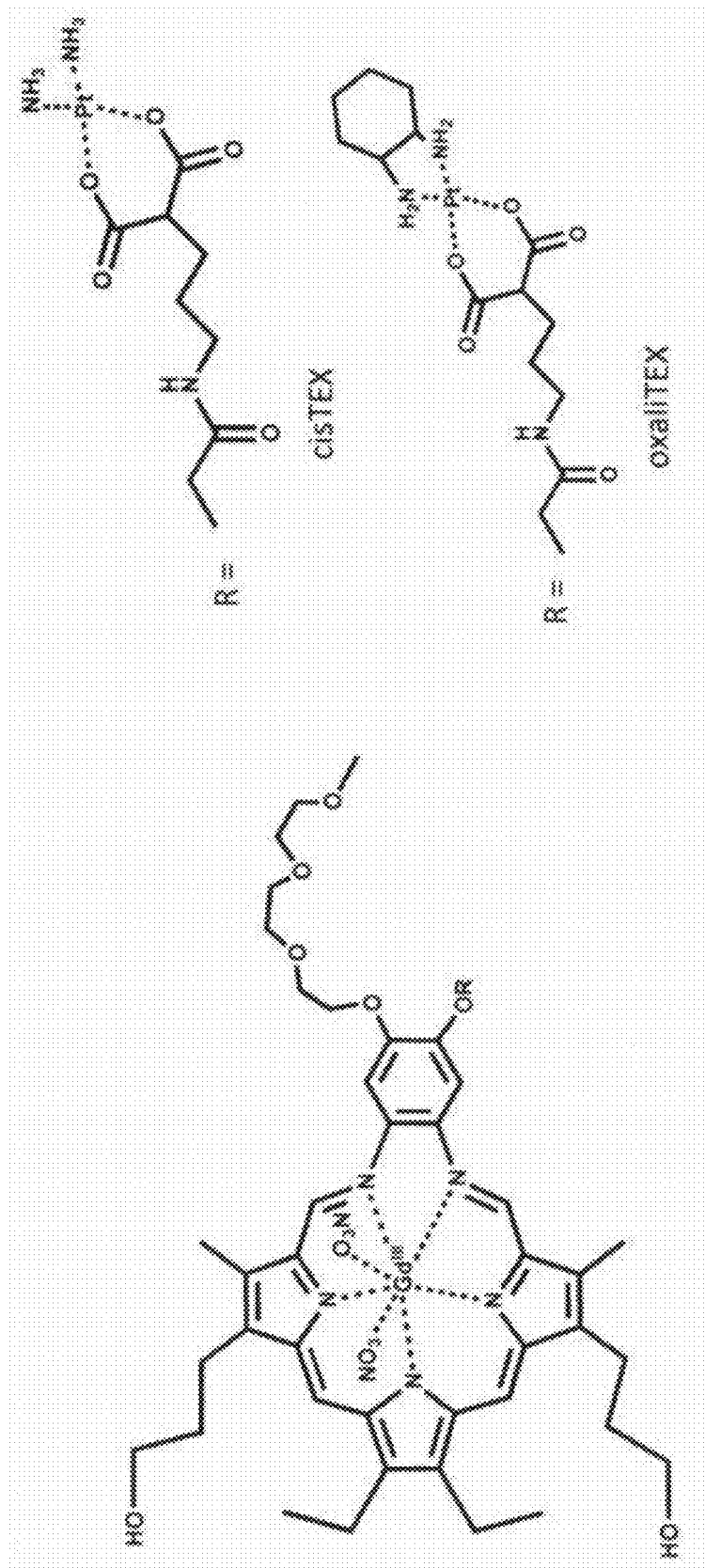
FIG. 2 shows the previous generation of platinum(II)-texaphyrin conjugates.
Figure 3:
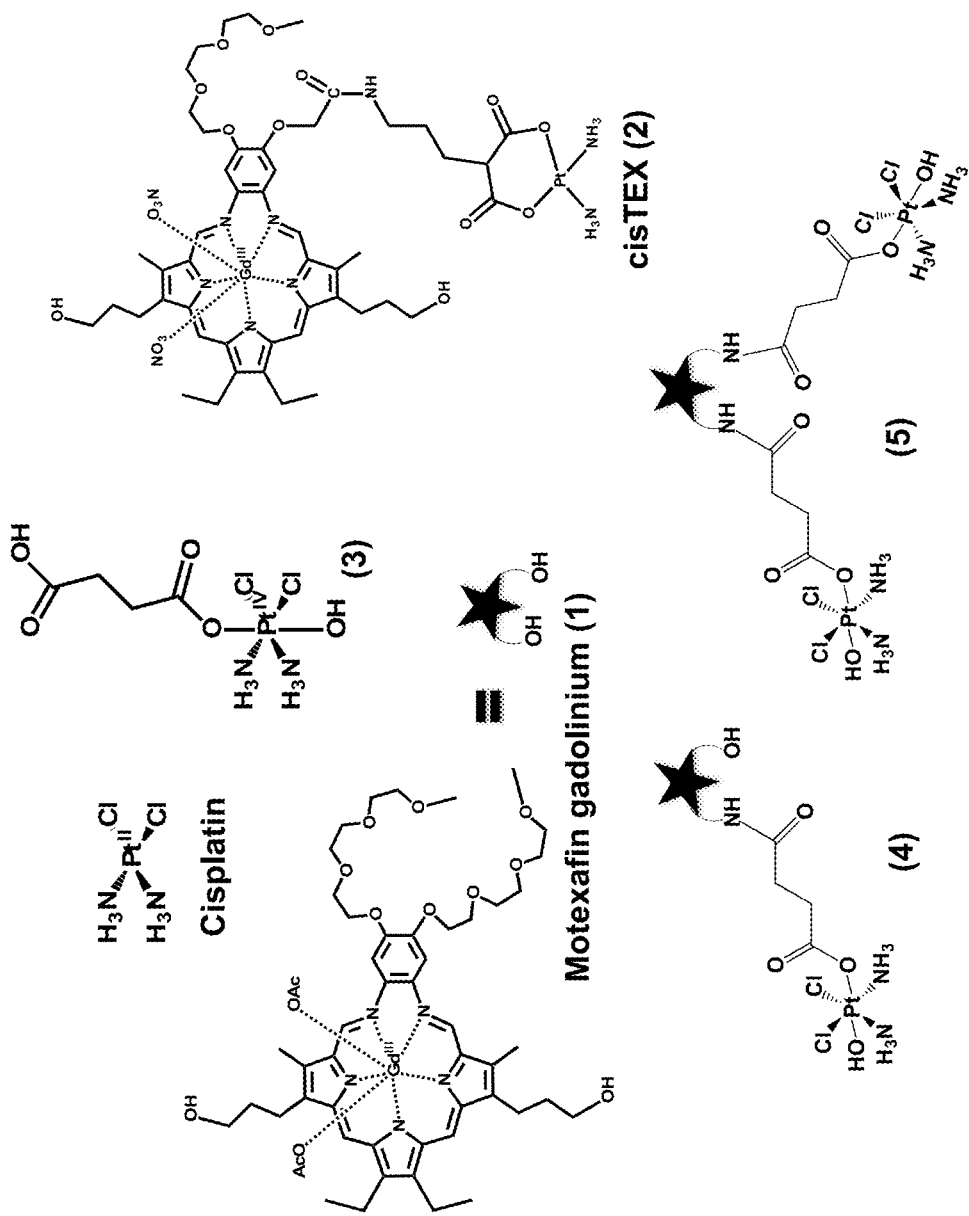
FIG. 3 shows some of the structures of compounds described in this disclosure.

The texaphyrin-platinum(IV) conjugates of the present disclosure display an increased stability toward hydrolysis and toward nucleophile such as 5'-guanosine monophosphate (5'-GMP), compared to the compounds approved by the FDA and earlier generations of platinum(II)-texaphyrin conjugates (FIG. 2). In some aspects, the new compounds are chemotherapeutic pro-drugs since the compounds are activated upon reduction by chemical reducing agents (such as sodium ascorbate, glutathione) and also via irradiation to natural light. In some aspects, the new compounds can be used as chemotherapeutic agents in platinum resistant cancer cell lines as the conjugates of the present disclosure display increased activity in platinum resistant cancer cell lines compared to traditional platinum agents. In some embodiments, the metallated texaphyrin may also be used to allow detection of the tumor or the location of the agents through imaging techniques such as MRI.

The present disclosure also describes methods of treating a cancer in a patient comprising administering a texaphyrin compound with a metal chemotherapeutic complex to the patient in a therapeutically effective amount. Without wishing to be bound by any theory, the texaphyrin compound localizes into a tumor cell and mediates the reduction of the metal chemotherapeutic complex to form a cytotoxic species. In some aspects, the present disclosure relates to administering a texaphyrin compound with a platinum(IV) complex wherein the texaphyrin compound mediates the reduction of the platinum(IV) complex into a cytotoxic platinum(II) complex. In some aspects, these compositions can be administered wherein the texaphyrin compound is tethered to the platinum(IV) complex or wherein the texaphyrin compound is not covalently linked to the platinum (IV) complex and is administered together or subsequently. In other embodiments, the texaphyrin compound and the platinum(IV) complex are administered with one or more additional therapeutic agents or modalities.

A. CHEMICAL DEFINTIONS

When used in the context of a chemical group: "hydrogen" means H; "hydroxy" means —OH; "oxo" means =O; "carbonyl" means —C(=O)—; "carboxy" means —C(=O) OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$^2$—; and "sulfinyl" means —S(O)—.

In the context of chemical formulas, the symbol "" means a single bond, "=" means a double bond, and "≡" means triple bond. The symbol " ---- " represents an optional bond, which if present is either single or double. The symbol " ==== " represents a single bond or a double bond. Thus, for example, the formula

includes

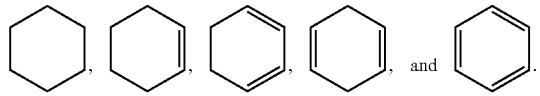

And it is understood that no one such ring atom forms part of more than one double bond. Furthermore, it is noted that the covalent bond symbol "-", when connecting one or two stereogenic atoms, does not indicate any preferred stereochemistry. Instead, it covers all stereoisomers as well as mixtures thereof. The symbol "〜", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◂▬" means a single bond where the group attached to the thick end of the wedge is "out of the page." The symbol "⫼⫼⫼⫼" means a single bond where the group attached to the thick end of the wedge is "into of the page". The symbol "◂▬" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

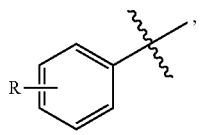

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

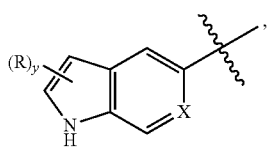

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms. (Cn-n') defines both the minimum (n) and maximum number (n') of carbon atoms in the group. Similarly, "alkyl(c2-lo)" designates those alkyl groups having from 2 to 10 carbon atoms.

The term "saturated" as used herein means the compound or group so modified has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl).

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Prorpropyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tent-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups, —CH$_2$—(methylene), —CH$_2$CH$_2$—, —CH$_2$C(CH$_3$)$_2$CH$_2$—, and —CH$_2$CH$_2$CH$_2$—, are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting example of a haloalkyl. The term "fluoroalkyl" is a subset of substituted alkyl, in which one or more hydrogen has been substituted with a fluoro group and no other atoms aside from carbon, hydrogen and fluorine are present. The groups, —CH₂F, —CF₃, and —CH₂CF₃ are non-limiting examples of fluoroalkyl groups.

The term "cycloalkyl" when used without the "substituted" modifier refers to a monovalent saturated aliphatic group with a carbon atom as the point of attachment, a linear or branched cyclo or cyclic structure, no carbon-carbon double or triple bonds, and no atoms other than carbon and hydrogen. As used herein, the cycloalkyl group may contain one or more branching alkyl groups (carbon number limit permitting) attached to the ring system so long as the point of attachment is the ring system. Non-limiting examples of cycloalkyl groups include: —CH(CH₂)₂ (cyclopropyl), cyclobutyl, cyclopentyl, or cyclohexyl. The term "cycloalkanediyl" when used without the "substituted" modifier refers to a divalent saturated aliphatic group with one or two carbon atom as the point(s) of attachment, a linear or branched cyclo or cyclic structure, no carbon-carbon double or triple bonds, and no atoms other than carbon and hydrogen.

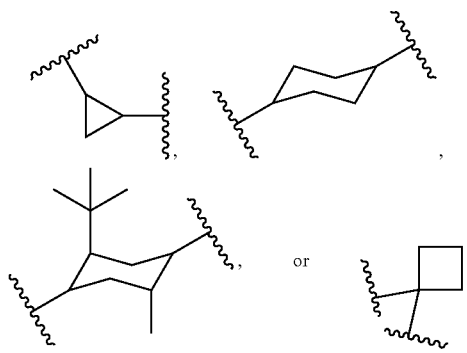

are non-limiting examples of cycloalkanediyl groups. The term "cycloalkylidene" when used without the "substituted" modifier refers to the divalent group =CRR' in which R and R' are taken together to form a cycloalkanediyl group with at least two carbons. Non-limiting examples of alkylidene groups include: =C(CH₂)₂ and =C(CH₂)₅. A "cycloalkane" refers to the compound H—R, wherein R is cycloalkyl as this term is defined above. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂. The following groups are non-limiting examples of substituted cycloalkyl groups: —C(OH)(CH₂)₂,

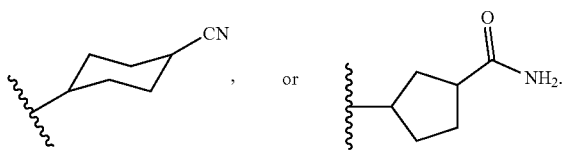 [SMILES: *C1CCC(C#N)CC1 ; *C1CCC(C(N)=O)C1]

The term "alkenyl" when used without the "substituted" modifier refers to a monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen.

Non-limiting examples of alkenyl groups include: —CH=CH₂ (vinyl), —CH=CHCH₃, —CH=CHCH₂CH₃, —CH₂CH=CH₂ (allyl), —CH₂CH=CHCH₃, and —CH=CHCH=CH₂. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH₃)CH₂, and CH=CHCH₂—, are non-limiting examples of alkenediyl groups. It is noted that while the alkenediyl group is aliphatic, once connected at both ends, this group is not precluded from forming part of an aromatic structure. The terms "alkene" and refer to a compound having the formula HR, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂. The groups, —CH=CHF, —CH=CHCl and —CH=CHBr, are non-limiting examples of substituted alkenyl groups.

The term "alkynyl" when used without the "substituted" modifier refers to a monovalent unsaturated aliphatic group with a carbon atom as the point of attachment, a linear or branched, acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH₃, and —CH₂C≡CCH₃, are non-limiting examples of alkynyl groups. An "alkyne" refers to the compound H—R, wherein R is alkynyl. When any of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C₆H₄CH₂CH₃ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

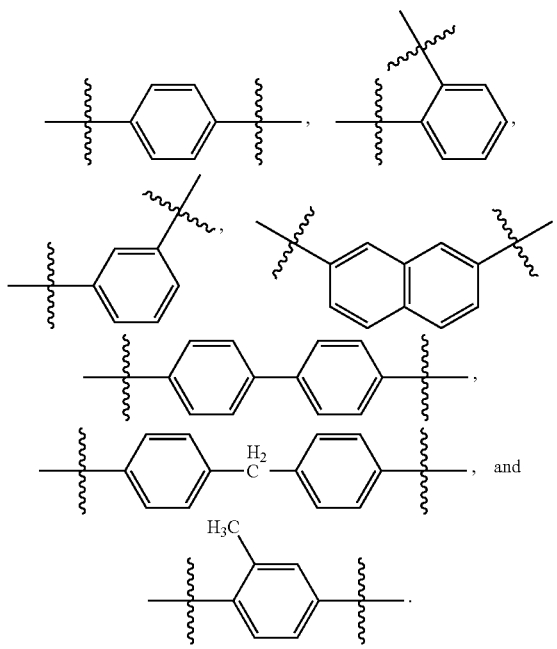

An "arene" refers to the compound HR, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$—CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "aralkyl" when used without the "substituted" modifier refers to the monovalent group-alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. Non-limiting examples of substituted aralkyls are: (3 -chlorophenyl)-m ethyl, and 2-chloro-2-phenyl-eth-1-yl .

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

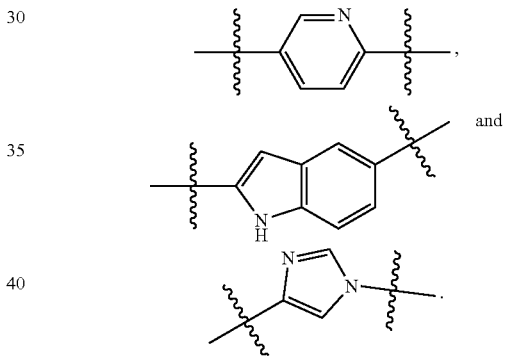

A "heteroarene" refers to the compound H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "acyl" when used without the "substituted" modifier refers to the group —C(O)R, in which R is a hydrogen, alkyl, cycloalkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and CON(CH$_3$)$_2$, are non-limiting examples of substituted acyl groups.

The term "alkoxy" when used without the "substituted" modifier refers to the group OR, in which R is an alkyl, as that term is defined above. Non-limiting examples of alkoxy groups include: —OCH$_3$ (methoxy), —OCH$_2$CH$_3$ (ethoxy), —OCH$_2$CH$_2$CH$_3$, —OCH(CH$_3$)$_2$ (isopropoxy), and —OC(CH$_3$)3 (tert-butoxy). The terms "cycloalkoxy", "alkenyloxy", "cycloalkenyloxy", " al kynyl oxy", " aryl oxy", "aralkoxy", " hetero aryl oxy", "heterocycloalkoxy", and "acyloxy", when used without the "substituted" modifier, refers to groups, defined as —OR, in which R is cycloalkyl, alkenyl, cycloalkenyl, alkynyl, aryl, aralkyl, heteroaryl, heterocycloalkyl, and acyl, respectively. The term "alkoxydiyl" refers to the divalent group —O-alkanediyl-, —O-alkanediyl-O—, or -alkanediyl-O-alkanediyl-. The terms "alkylthio", "cycloalkylthio", and "acylthio" when used without the "substituted" modifier refers to the group —SR, in which R is an alkyl, cycloalkyl, and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy or cycloalkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can each independently be the same or different alkyl groups, or R and R' can be taken together to represent an alkanediyl. The term "dicycloalkylamino" or "diarylamino" when used without the "substituted" modifier refers to the group —NRR', in which R and R' can each independently be the same or different cycloalkyl or aryl groups, respectively. Non-limiting examples of dialkylamino groups include: —N(CH$_3$)$_2$, —N(CH$_3$)(CH$_2$CH$_3$), and N-pyrrolidinyl. The terms "alkoxyamino", "cycloalkylamino", "alkenylamino", "cycloalkenylamino", "alkynylamino", "arylamino", "aralkylamino", "heteroarylamino", "heterocycloalkylamino" and "alkylsulfonylamino" when used without the "substituted" modifier, refers to groups, defined as —NHR, in which R is alkoxy, cycloalkyl, alkenyl, cycloalkenyl, alkynyl, aryl, aralkyl, heteroaryl, heterocycloalkyl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylamine" when used without the "substituted" modifier, refers to a group defined as defined as NH$_2$R, NH(CH$_3$)R, or N(CH$_3$)$_2$R in which R is alkyl as that term is defined above. Similarly, the terms "alkoxyamine", "cycloalkylamine", "alkenylamine", "cycloalkenylamine", "alkynylamine", "arylamine", "aralkylamine", "heteroarylamine", "heterocycloalkylamine" and "alkylsulfonylamine" when used without the "substituted" modifier, refers to groups, defined as NH$_2$R in which R is alkoxy, cycloalkyl, alkenyl, cycloalkenyl, alkynyl, aryl, aralkyl, heteroaryl, heterocycloalkyl, and alkylsulfonyl, respectively. Additionally, a dialkylamine or dicycloalkylamine is as those terms are defined above and the point of connectivity is a hydrogen atom. The term "alkylimino" when used without the "substituted" modifier refers to the divalent group =NR, in which R is an alkyl, as that term is defined above. The term "alkylaminodiyl" refers to the divalent group —NH-alkanediyl-, —N-Halkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

As used herein, the term "ligand" references to a chemical group which coordinates to a metal center through a bond. The bond between the ligand and the metal center in some cases is either an ionic or a coordination bond. A ligand can be monovalent, divalent, trivalent or have a greater valency. In some cases, a ligand may be negatively charged. Some exemplary examples of ligands include, but are not limited to, halide (F$^-$, Cl$^-$, Br$^-$, or I$^-$), a carbonate (CO$_3^{2-}$), bicarbonate (HCO$_3^-$), hydroxide ($^-$OH), perchlorate (ClO$_4^-$), nitrate (NO$_3^-$), sulfate (SO$_4^{2-}$), acetate (CH$_3$CO$_2^-$), trifluoroacetate (CF$_3$CO$_2^-$), acetylacetonate (CH$_3$COCHCOCH$_3^-$), trifluorosulfonate (CF$_3$SO$_2^-$), or phosphate (PO$_4^{3-}$). A ligand could also be a neutral species that contains a lone pair of electrons. Some examples of neutral ligands include but are not limited to aqua (H$_2$O) or ammonia (NH$_3$). Additionally, a neutral ligand can include groups such as an alkylamine or a dialkylamine.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, —N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethane sulfonate s, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

A "repeat unit" is the simplest structural entity of certain materials, for example, frameworks and/or polymers, whether organic, inorganic or metal-organic. In the case of a polymer chain, repeat units are linked together successively along the chain, like the beads of a necklace. For example, in polyethylene, —[—$CH_2CH_2$—]$_n$, the repeat unit is —$CH_2CH_2$—. The subscript "n" denotes the degree of polymerization, that is, the number of repeat units linked together. When the value for "n" is left undefined or where "n" is absent, it simply designates repetition of the formula within the brackets as well as the polymeric nature of the material. The concept of a repeat unit applies equally to where the connectivity between the repeat units extends three dimensionally, such as in metal organic frameworks, modified polymers, thermosetting polymers, etc.

In the context of this application, "selectively" means that greater than 50% of the activity of the compound is exhibited in the noted location. On the other hand, "preferentially" means that greater than 75% of the activity of the compound is exhibited in the noted location.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that for tetrahedral stereogenic centers the stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

B. COMPOUNDS OF THE PRESENT INVENTION

In some aspects, the present invention relates to compounds of the formula:

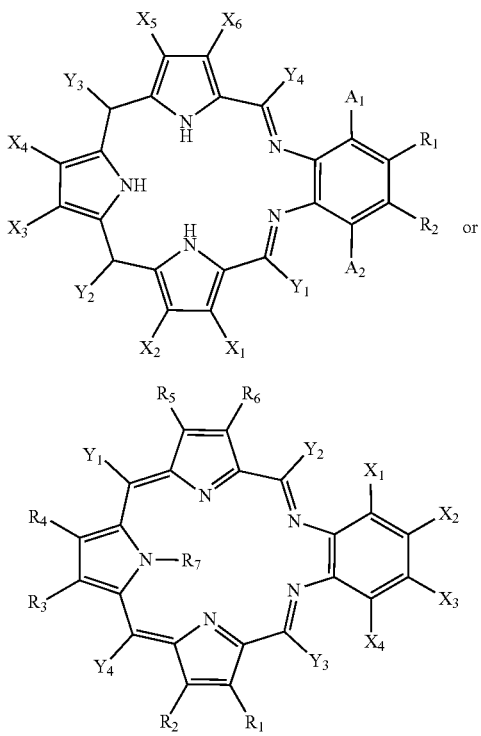

wherein:

$R_1$ and $R_2$ are each independently selected from hydrogen, halo, hydroxy, amino, mercapto, alkoxy$_{(C \leq 12)}$, substituted alkoxy$_{(C \leq 12)}$, or

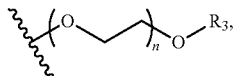

wherein n is 1-20 and $R_3$ is hydrogen, alkyl$_{(C \leq 6)}$, or substituted alkyl$_{(C \leq 6)}$, or a platinum(IV) chelating group;

$A_1$ and $A_2$ are each independently selected from hydrogen, halo, hydroxy, alkyl$_{(C \leq 12)}$, substituted alkyl$_{(C \leq 12)}$, alkoxy$_{(C \leq 12)}$, substituted alkoxy$_{(C \leq 12)}$, or

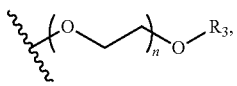

wherein n is 1-20 and $R_3$ is hydrogen, alkyl$_{(C \leq 6)}$, or substituted alkyl$_{(C \leq 6)}$, or a platinum(IV) chelating group;

$Y_1$, $Y_2$, $Y_3$, and $Y_4$ are each independently selected from hydrogen, halo, alkyl$_{(C \leq 12)}$, aryl$_{(C \leq 12)}$, substituted alkyl$_{(C \leq 12)}$, or substituted aryl$_{(C \leq 12)}$;

$X_1$, $X_2$, $X_3$, $X_4$, $X_5$, and $X_6$ are each independently selected from hydrogen, hydroxy, halo, amino, carboxy, nitro, or cyano, alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, acyl$_{(C \leq 12)}$, amido$_{(C \leq 12)}$, or a substituted version of any of these groups, or a platinum(IV) chelating group;

$R_7$ is hydrogen, alkyl$_{(C \leq 8)}$, cycloalkyl$_{(C \leq 8)}$, alkenyl$_{(C \leq 8)}$, cycloalkenyl$_{(C \leq 8)}$, alkynyl$_{(C \leq 8)}$, alkoxy$_{(C \leq 8)}$, or a substituted version of any of these groups, or an amino protecting group;

provided that at least one of $X_1$, $X_2$, $X_3$, $X_4$, $X_5$, and $X_6$ is a platinum(IV) chelating group or an oxidized metal complex, a pharmaceutically acceptable salt, or tautomer thereof. As used herein, a platinum(IV) chelating group that may be used includes a complex of the formula:

$$-A_3-X_7-A_4-R_4,$$

wherein:

$A_3$ and $A_4$ are each independently alkanediyl$_{(C \leq 12)}$, alkenediyl$_{(C \leq 12)}$, arenediyl$_{(C \leq 12)}$, alkoxydiyl$_{(C \leq 12)}$, alkylaminodiyl$_{(C \leq 12)}$, or a substituted version of any of these groups, $X_7$ is —O—, —S—, —NR$_5$—, —C(O)NR$_5$—, or —NR$_5$C(O)—, wherein $R_5$ is hydrogen, alkyl$_{(C \leq 6)}$, or substituted alkyl$_{(C \leq 6)}$, and $R_4$ is amino, hydroxy, mercapto, carboxy, dicarboxy, or

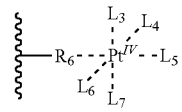

wherein:

$R_6$ is amino, hydroxy, mercapto, carboxy, or dicarboxy;

$L_3$, $L_4$, $L_5$, and $L_6$ are each ligands independently selected from aqua, ammonia, nitrate, sulfate, halide, hydroxide, phosphate, or glucose-6-phosphate, alkylamine$_{(C \leq 12)}$, cycloalkylamine$_{(C \leq 12)}$, dialkylamine$_{(C \leq 18)}$, dicycloalkylamine$_{(C \leq 18)}$, arylamine$_{(C \leq 12)}$, diarylamine$_{(C \leq 18)}$, diaminoalkane$_{(C \leq 12)}$, diaminocycloalkane$_{(C \leq 12)}$, diaminoarene$_{(C \leq 12)}$, heteroarene$_{(C \leq 12)}$, alkylcarboxylate$_{(C \leq 12)}$, alkyldicarboxylate$_{(C \leq 18)}$, arylcarboxylate$_{(C \leq 12)}$, aryldicarboxylate$_{(C \leq 18)}$, or a substituted version of any of these groups.

Furthermore, an oxidized metal complex may have the formula:

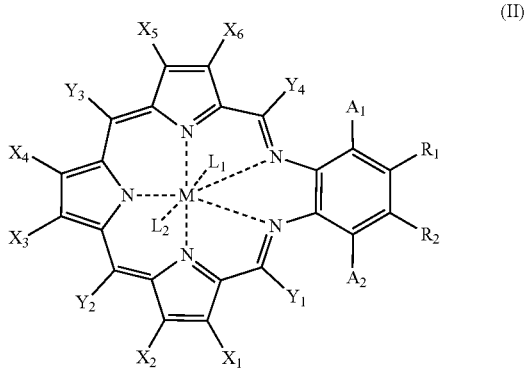

(II)

wherein: $R_1$, $R_2$, $A_1$, $A_2$, $Y_1$, $Y_2$, $Y_3$, $Y_4$, $X_1$, $X_2$, $X_3$, $X_4$, $X_5$, and $X_6$ are as defined above;

M is a monovalent metal ion, a divalent metal ion, or a trivalent metal ion; and $L_1$ and $L_2$ are each absent or anionic ligands independently selected from fluoride, chloride, bromide, carbonate, hydroxide, perchlorate, nitrate, sulfate, trifluoromethylsulfonate, acetylacetonate, acetate, or trifluoroacetate;

provided that when M is a monovalent metal ion then $L_1$ and $L_2$ are absent, and when M is a divalent metal ion, then $L_1$ or $L_2$ is absent;

or a pharmaceutically acceptable salt thereof.

The compounds provided by the present disclosure are shown, for example, above in the summary of the invention section and in the claims below. They may be made using the methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Compounds of the invention may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. In the context of this disclosure, metal complexes may exist in each of their isomeric forms such that the ligands may be rearranged to form the other isomers. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration. Additionally, stereoisomers of the metal center including the Pt(IV) cation arising from the various arrangements of the ligands around the metal ion are also contemplated.

Chemical formulas used to represent compounds of the invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

Compounds of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$. Additionally, the metal ions in the present invention can have different oxidation states unless otherwise noted. As used herein, the charge on the metal atom can be denoted either as a superscript such as $Pt^{IV}$ or using parenthesis such as Pt(IV). These two forms are identical as would be recognized to a person of skill in the art. Even if one form is used in the application to describe the oxidation state in one place in the application, it is contemplated that the other form could be used in elsewhere in the application.

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

Those skilled in the art of organic chemistry will appreciate that many organic compounds can form complexes with solvents in which they are reacted or from which they are precipitated or crystallized. These complexes are known as "solvates." For example, a complex with water is known as a "hydrate." Solvates of the compounds provided herein are within the scope of the invention. It will also be appreciated by those skilled in organic chemistry that many organic compounds can exist in more than one crystalline form. For example, crystalline form may vary from solvate to solvate. Thus, all crystalline forms of the compounds provided herein or the pharmaceutically acceptable solvates thereof are within the scope of the present invention.

C. METAL CHEMOTHERAPEUTIC COMPLEXES

In some aspects, the present disclosure provides methods and compositions which uses a metal chemotherapeutic complex. Some non-limiting examples of metal chemotherapeutic complexes which may be used include platinum(II), platinum(IV), osmium(II), titanium(IV), iridium(III), iron (II), copper(II), rhodium(III), ruthenium(II), cobalt(III), gallium(III), arsenic(III), molybdenium(VI), gold(I), gold(III), lanthanum(III), or tin(IV) (Romero-Canelon and Sadler, 2013). In some embodiments, these metal complexes may be administered in a higher oxidation state as a high oxidation metal containing chemotherapeutic complex to reduce side effects and/or improve other pharmacokinetic properties. In some embodiments, these compounds are oxidatively sensitive and thus when exposed to reducing agents in vivo will reduce to form a complex at a different oxidation state. In some embodiments, these compounds are show more cytotoxicity after exposure to the reducing agent than the compound before reduction. In some aspects, these compounds are pro-drugs because they must be reduced in situ to form the cytotoxic species. In some embodiments, the present invention provides the use of one of these pro-drug metal chemotherapeutic complexes in conjunction with a texaphyrin compound which mediates the reduction to the cytotoxic form. In some embodiments, this process is selective for cancer cells, since the texaphyrin preferentially localizes to cancerous cells (U.S. Pat. Nos. 5,599,923 and 5,599,928). In some embodiments, the metal chemotherapeutic complex is a high oxidation state gold, platinum, osmium, or ruthenium complex. For example, such high oxidation state metal chemotherapeutic complexes are taught by, U.S. Pat. Nos. 4,265,823, 4,845,124, 4,870,208, 4,980,473, 5,072,011, 5,409,915, 5,624,919, 6,340,599, 6,774,254, 7,479,557, 7,655,697, 7,655,810, 8,193,175, 8,357,678, 8,481,496, 8,563,712, 8,653,132, 8,729,286, 8,748,484, 8,877,215, 8,828,984, and U.S. Patent Applications 2012/0164230, 2013/0303606, 2014/0221475, 2014/0274988, PCT International Applications WO9824424, WO2010027428, WO2012177935, WO2014165782, Chinese Application CN102058576, Chen et al., 2013; Hall et al., 2002; Hall et al., 2003; Hall et al., 2012; Nemirovski et al., 2010; Novohradsky et al., 2014; Shi et al., 2012; Wexselblatt et al., 2012; Wexselblatt et al., 2015; Zhang et al., 2012a; Zhang et al., 2012b; Zhang et al., 2013; Zheng et al., 2015, Zhu et al., 2014, which are all incorporated herein by reference. In some embodiments, the metal chemotherapeutic complex is a high oxidation state platinum complex. In one particular embodiments, the high oxidation state platinum complex is a platinum(IV) complex.

D. TEXAPHYRIN COMPOUNDS

In some aspects, the present disclosure provides compositions and methods comprising a texaphyrin compound with or without a platinum chelating group directly bound to the macrocycle, wherein the texaphyrin is a macrocycle of the formula:

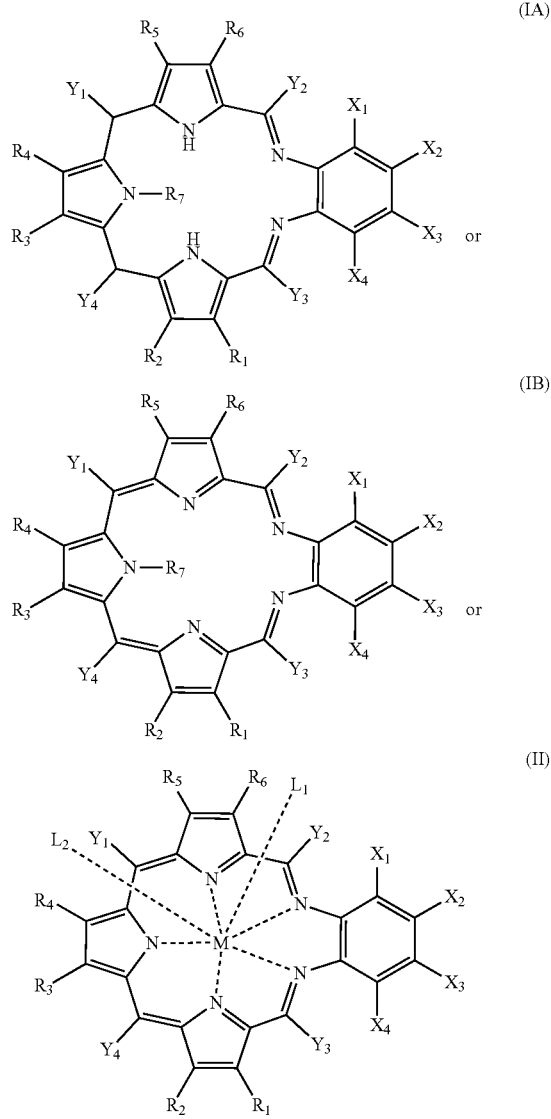

wherein:
$Y_1$-$Y_4$ are each independently selected from: hydrogen, amino, cyano, halo, hydroxy, or hydroxyamino,
alkyl$_{(C\le12)}$, cycloalkyl$_{(C\le12)}$, alkenyl$_{(C\le12)}$, cycloalkenyl$_{(C\le12)}$, alkynyl$_{(C\le12)}$, aryl$_{(C\le12)}$, aralkyl$_{(C\le12)}$, heteroaryl$_{(C\le12)}$, heterocycloalkyl$_{(C\le12)}$, acyl$_{(C\le12)}$, alkoxy$_{(C\le12)}$, acyloxy$_{(C\le12)}$, aryloxy$_{(C\le12)}$, heteroaryloxy$_{(C\le12)}$, heterocycloalkoxy$_{(C\le12)}$, amido$_{(C\le12)}$, alkylamino$_{(C\le12)}$, dialkylamino$_{(C\le12)}$, alkylthio$_{(C\le12)}$, arylthio$_{(C\le12)}$, alkylsulfinyl$_{(C\le12)}$, arylsulfinyl$_{(C\le12)}$, alkylsulfonyl$_{(C\le12)}$, arylsulfonyl$_{(C\le12)}$, or a substituted version of any of these groups; or
$R_1$-$R_6$ are each independently selected from: hydrogen, amino, cyano, halo, hydroxy, hydroxyamino, or nitro, alkyl$_{(C\le12)}$, cycloalkyl$_{(C\le12)}$, alkenyl$_{(C\le12)}$, cycloalkenyl$_{(C\le12)}$, alkynyl$_{(C\le12)}$, aryl$_{(C\le12)}$, aralkyl$_{(C\le12)}$, heteroaryl$_{(C\le12)}$, heterocycloalkyl$_{(C\le12)}$, acyl$_{(C\le12)}$, alkoxy$_{(C\le12)}$, acyloxy$_{(C\le12)}$, aryloxy$_{(C\le12)}$, heteroaryloxy$_{(C\le12)}$, heterocycloalkoxy$_{(C\le12)}$, amido$_{(C\le12)}$, alkylamino$_{(C\le12)}$, dialkylamino$_{(C\le12)}$, or a substituted version of any of these groups; or a PEG moiety wherein the PEG moiety is of the formula:
—(OCH$_2$CH$_2$)$_n$OR$_8$; wherein:
n is 1-20; and
R$_8$ is hydrogen, alkyl$_{(C≤8)}$, or substituted alkyl$_{(C≤8)}$; or
a platinum(IV) chelating group;
R$_7$ is hydrogen,
alkyl$_{(C≤8)}$, cycloalkyl$_{(C≤8)}$, alkenyl$_{(C≤8)}$, cycloalkenyl$_{(C≤8)}$, alkynyl(c<s), alkoxy$_{(C≤8)}$, or a substituted version of any of these groups, or
an amino protecting group;
X$_1$-X$_4$ are each independently selected from: hydrogen, amino, cyano, halo, hydroxy, hydroxyamino, or nitro,
alkyl$_{(C≤12)}$, cycloalkyl$_{(C≤12)}$, alkenyl$_{(C≤12)}$, cycloalkenyl$_{(C≤12)}$, alkynyl$_{(C≤12)}$, aryl$_{(C≤12)}$, aralkyl$_{(C≤12)}$, heteroaryl$_{(C≤12)}$, heterocycloalkyl$_{(C≤12)}$, acyl$_{(C≤12)}$, alkoxy$_{(C≤12)}$, acyloxy$_{(C≤12)}$, aryloxy$_{(C≤12)}$, heteroaryloxy$_{(C≤12)}$, heterocycloalkoxy$_{(C≤12)}$, amido$_{(C≤12)}$, alkylamino$_{(C≤12)}$, dialkylamino$_{(C≤12)}$, or a substituted version of any of these groups; or
a PEG moiety wherein the PEG moiety is of the formula:
—(OCH$_2$CH$_2$)$_n$OR$_8$; wherein:
n is 1-20; and
R$_8$ is hydrogen, alkyl$_{(C≤8)}$, or substituted alkyl$_{(C≤8)}$; or
a platinum(IV) chelating group;
L$_1$ and L$_2$ are each independently absent, a neutral ligand, or an anionic ligand; and
M is a metal ion;
provided that L$_1$ and L$_2$ are present or absent in a manner sufficient to balance the charge on the metal ion;
or a pharmaceutically acceptable salt or tautomer thereof.

Additional non-limiting examples of texaphyrins are taught by U.S. Pat. Nos. 4,935,498, 5,252,270, 5,272,142, 5,292,414, 5,369,101, 5,432,171, 5,439,570, 5,504,205, 5,569,759, 5,583,220, 5,587,463, 5,591,422, 5,633,354, 5,776,925, 5,955,586, 5,994,535, 6,207,660, 7,112,671, and 8,410,263, which are all incorporated herein by reference. When the term, "texaphyrin compound" is used herein it can refer to a texaphyrin in both its oxidized and reduced forms, a metallotexaphyrin, or any of these groups. As would be known by a person of skill in the art, texaphyrins are known to under oxidation when a metal ion is bound. This phenomenon is described in U.S. Pat. No. 5,504,205, Shimanovich, et al., 2001 and Hannah, et al., 2001, all of which are incorporated herein by reference. As this process is linked with the metalation of the texaphyrin compound, these compounds are referenced to herein as an oxidized metallated derivative of the reduced macrocycle formula.

In some aspects, the present disclosure provides compositions and methods of use of the metallated form of the texaphyrin compound. In some embodiments, the metal of the metallated form is a transition metal. In some embodiments, the metal is a metal ion in the 2+ oxidation state or the 3+ oxidation state. In some embodiments, the metal is an actinide or lanthanide. In some embodiments, the metal is lutetium or gadolinium. In some embodiments, the metal atom is gadolinium. In some aspects, the texaphyrin compound is administered simultaneously with a reducing agent. In some embodiments, the reducing agent is a two electron donor. In some embodiments, the reducing agent is sodium ascorbate, thioredoxin reductase, a platinum(II) ion or complex, or a biological thiol, including but not limited to cysteine, homocysteine, or glutathione. A photoreduction may also be used in conjunction with the texaphyrin compound.

E. HYPERPROLIFERATIVE DISEASES

While hyperproliferative diseases can be associated with any medical disorder that causes a cell to begin to reproduce uncontrollably, the prototypical example is cancer. One of the key elements of cancer is that the normal apoptotic cycle of the cell is interrupted and thus agents that lead to apoptosis of the cell are important therapeutic agents for treating these diseases. As such, the texaphyrin and platinum (IV) analogues and compositions described in this disclosure may be effective in treating cancers.

Cancer cells that may be treated with the compounds according to the embodiments include but are not limited to cells from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia.

F. PHARMACEUTICAL FORMULATIONS AND ROUTES OF ADMINISTRATION

For administration to a mammal in need of such treatment, the texaphyrin and platinum(IV) analogues and compositions conjugate of the present invention are ordinarily combined with one or more excipients appropriate to the indicated route of administration. The texaphyrin and platinum(IV) analogues and compositions of the present invention may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and tableted or encapsulated for convenient administration. Alternatively, the conjugates may be dissolved in water, polyethylene glycol, propylene glycol, ethanol, corn oil, cottonseed oil, peanut oil, sesame oil, benzyl alcohol, sodium chloride, and/or various buffers. Other excipients and modes of administration are well and widely known in the pharmaceutical art.

The pharmaceutical compositions useful in the present invention may be subjected to conventional pharmaceutical operations such as sterilization and/or may contain conventional pharmaceutical carriers and excipients such as preservatives, stabilizers, wetting agents, emulsifiers, buffers, etc.

The texaphyrin and platinum(IV) analogues and compositions of the present invention may be administered by a variety of methods, e.g., orally or by injection (e.g. subcutaneous, intravenous, intraperitoneal, etc.). Depending on the route of administration, the novel conjugates may be coated in a material to protect the compound from the action of acids and other natural conditions which may inactivate the compound. They may also be administered by continuous perfusion/infusion of a disease or wound site.

To administer the therapeutic compound by other than parenteral administration, it may be necessary to coat the texaphyrin and platinum(IV) analogues and compositions of the present invention with, or co-administer the texaphyrin and platinum(IV) analogues and compositions of the present invention with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes. Additionally, Trapasol®, Travasol®, cyclodextrin, and other drug carrier molecules may also be used in combination with the texaphyrin and platinum(IV) analogues and compositions of the present disclosure. It is contemplated that the compounds of the present disclosure may be formulated with a cyclodextrin as a drug carrier using an organic solvent such as dimethylaceamide with a polyethylene glycol and a poloxamer composition in an aqueous sugar solution. In some embodiments, the organic solvent is dimethylsulfoxide, dimethylformamide, dimethylacetamide, or other biologically compatible organic solvents. Additionally, the composition may be diluted with a polyethylene glycol polymer such as PEG100, PEG200, PEG250, PEG400, PEG500, PEG600, PEG750, PEG800, PEG900, PEG1000, PEG2000, PEG2500, PEG3000, or PEG4000. Additionally, the composition may further comprise one or more poloxamer composition wherein the poloxamer contains two hydrophilic polyoxyethylene groups and a hydrophobic polyoxypropylene or a substituted version of these groups. This mixture may be further diluted using an aqueous sugar solution such as 5% aqueous dextrose solution.

The texaphyrin and platinum(IV) analogues and compositions of the present invention may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion are also envisioned. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the texaphyrin and platinum(IV) analogues and compositions of the present invention in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The texaphyrin and platinum(IV) analogues and compositions of the present invention can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the conjugates may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the texaphyrin and platinum(IV) analogues and compositions of the present invention in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of the texaphyrin and platinum(IV) analogues and compositions of the present invention calculated to produce the desired therapeutic effect in association with the required pharmaceutical carrier. The specification for the dosage unit forms of the invention are dictated by and directly dependent on (a) the unique characteristics of the texaphyrin and platinum(IV) analogues and compositions of the present invention and the particular therapeutic effect to be achieved, and (b) the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

The texaphyrin and platinum(IV) analogues and compositions of the present invention describe in this disclosure are administered at a therapeutically effective dosage sufficient to treat a condition associated with a condition in a patient. For example, the efficacy of the texaphyrin and platinum(IV) analogues and compositions of the present invention can be evaluated in an animal model system that may be predictive of efficacy in treating the disease in humans, such as the model systems shown in the examples and drawings.

The actual dosage amount of the texaphyrin and platinum (IV) analogues and compositions of the present disclosure or composition comprising the conjugates of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 1 mg/kg to about 50 mg/kg, in one or more dose administrations daily, for one or several days (depending of course of the mode of administration and the factors discussed above). In some particular embodiments, the amount is less than 5,000 mg per day with a range of 10 mg to 4500 mg per day.

The effective amount may be less than 10 mg/kg/day, less than 50 mg/kg/day, less than 100 mg/kg/day, less than 250 mg/kg/day. It may alternatively be in the range of 1 mg/kg/day to 250 mg/kg/day.

In other non-limiting examples, a dose may also comprise from about 0.1 mg/kg/body weight, about 1 mg/kg/body weight, about 10 g/kg/body weight, about 50 g/kg/body weight, or more per administration, and any range derivable therein. In non-limiting examples of a derivable range from the numbers listed herein, a range of about 1 mg/kg/body weight to about 50 mg/kg/body weight, about 5 g/kg/body weight to about 10 g/kg/body weight, etc., can be administered, based on the numbers described above.

In certain embodiments, a pharmaceutical composition of the present disclosure may comprise, for example, at least about 0.1% of a conjugate described in the present disclosure. In other embodiments, the compound of the present disclosure may comprise between about 0.25% to about 75% of the weight of the unit, or between about 25% to about 60%, or between about 1% to about 10%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agents are administered once a day.

The compounds may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may taken orally and that the timing of which is or is not dependent upon food intake. Thus, for example, the agents can be taken every morning and/or every evening, regardless of when the subject has eaten or will eat.

G. COMBINATION THERAPY

In some aspects, the present disclosure provides compositions of a texaphyrin compound and an high oxidation state metal chemotherapeutic agent such as a platinum(IV) complex. It is contemplated that these agents may be administered simultaneously. These compositions may be formulated as unit dose with both agents such that both agents are administered together. In other aspects, the texaphyrin compound may be administered before the high oxidation state metal chemotherapeutic agent by a time period from a few minutes to about one week. In some embodiments, the time period is from about 1 hour to about 24 hours. Thus, the time period may be from about 1, 2, 3, 4, 5, 6, 7, 8, 9, 10, 11, 12, 13, 14, 15, 16, 17, 18, 19, 20, 21, 22, 23, 24, 27, 30, 33, 36, 42, or 48 hours, or any range derivable therein. In other embodiments, the high oxidation metal chemotherapeutic agent may be administered before the texaphyrin compound by a similar time period.

In addition to being used as a monotherapy, the texaphyrin and platinum(IV) analogues and compositions of the present invention may also find use in combination therapies. Effective combination therapy may be achieved with a single composition or pharmacological formulation that includes both agents, or with two distinct compositions or formulations, administered at the same time, wherein one composition includes an texaphyrin and platinum(IV) analogues and compositions, and the other includes the second agent(s). The other therapeutic modality may be administered before, concurrently with, or following administration of the texaphyrin and platinum(IV) analogues and compositions of the present invention. The therapy using the texaphyrin and platinum(IV) analogues and compositions of the present invention may precede or follow administration of the other agent(s) by intervals ranging from minutes to weeks. In embodiments where the other agent and the compounds or compositions of the present disclosure are administered separately, one would generally ensure that a significant period of time did not expire between the time of each delivery, such that each agent would still be able to exert an advantageously combined effect. In such instances, it is contemplated that one would typically administer the texaphyrin and platinum(IV) analogues and compositions of the present invention and the other therapeutic agent within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of a texaphyrin-platinum(IV) conjugate or a composition of the texaphyrin compound and a high oxidation metal chemotherapeutic agent of the present disclosure, or the other agent will be desired. In this regard, various combinations may be employed. By way of illustration, where the compounds of the present disclosure are "A" and the other agent is "B", the following permutations based on 3 and 4 total administrations are exemplary:

| A/B/A B/A/B B/B/A A/A/B B/A/A A/B/B B/B/B/A B/B/A/B |
| A/A/B/B A/B/A/B A/B/B/A B/B/A/A B/A/B/A B/A/A/B B/B/B/A |
| A/A/A/B B/A/A/A A/B/A/A A/A/B/A A/B/B/B B/A/B/B B/B/A/B |

Other combinations are likewise contemplated. Non-limiting examples of pharmacological agents that may be used in the present invention include any pharmacological agent known to be of benefit in the treatment of a cancer or hyperproliferative disorder or disease. In some embodiments, combinations of the texaphyrin-platinum(IV) conjugate or the composition of a texaphyrin compound and a high oxidation state metal chemotherapeutic agent of the present invention with a cancer targeting immunotherapy, radiotherapy, chemotherapy, or surgery are contemplated. Also contemplated is a combination of the texaphyrin-platinum(IV) conjugate the composition of a texaphyrin compound and a high oxidation state metal chemotherapeutic agent of the present disclosure with more than one of the above mentioned methods including more than one type of a specific therapy. In some embodiments, it is contemplated that the immunotherapy is a monoclonal antibody which targets $HER_2$/neu such trastuzumab (Herceptin®), alemtuzumab (Campath®), bevacizumab (Avastin®), cetuximab (Eribitux®), and panitumumab (Vectibix®) or conjugated antibodies such as ibritumomab tiuxetan (Zevalin®), tositumomab (Bexxar®), brentuximab vedotin (Adcetris®), ado-trastuzumab emtansine (Kadcyla™), or denileukin diftitox (Ontak®) as well as immune cell targeting antibodies such as ipilimumab (Yervoy®), tremelimumab, anti-PD-1, anti-4-1-BB, anti-GITR, anti-TIM3, anti-LAG-3, anti-TIGIT, anti-CTLA-4, or anti-LIGHT. Furthermore, in some embodiments, the texaphyrin-platinum(IV) conjugate the composition of a texaphyrin compound and a high oxidation state metal chemotherapeutic agent of the present disclosure are envisioned to be used in combination therapies with dendritic cell-based immunotherapies such as Sipuleucel-T (Provenge®) or adoptive T-cell immunotherapies.

Furthermore, it is contemplated that the methods described herein may be used in combination with a chemotherapeutic agent such as PR-171 (Kyprolis®), bortezomib (Velcade®), anthracyclines, taxanes, methotrexate, mitoxantrone, estramustine, doxorubicin, etoposide, vinblastine, vinorelbine, 5-fluorouracil, cisplatin, carboplatin, oxaliplatin, Pt(IV) complexes, topotecan, ifosfamide, cyclophosphamide, epirubicin, gemcitabine, vinorelbine, irinotecan, etoposide, vinblastine, pemetrexed, melphalan, capecitabine, oxaliplatin, BRAF inhibitors, and TGF-beta inhibitors. In some embodiments, the combination therapy is designed to target a cancer such as those listed above.

In some aspects, it is contemplated that the texaphyrin-platinum(IV) conjugate or the composition of a texaphyrin compound and a high oxidation state metal chemotherapeutic agent may be used in conjunction with radiation therapy. Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly.

Radiation therapy used according to the present invention may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors induce a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

Additionally, it is contemplated texaphyrin-platinum(IV) conjugate the composition of a texaphyrin compound and a high oxidation state metal chemotherapeutic agent of the present invention are used in combination with sonodynamic therapy. The use of texaphyrins in sonodynamic therapy is described in U.S. Pat. No. 6,207,660 incorporated herein by reference. A texaphyrin-platinum(IV) conjugate or the composition is administered before administration of the sonodynamic agent. The conjugate or composition may be administered as a single dose, or it may be administered as two or more doses separated by an interval of time. Parenteral administration is typical, including by intravenous and interarterial injection. Other common routes of administration can also be employed.

Ultrasound is generated by a focused array transducer driven by a power amplifier. The transducer can vary in diameter and spherical curvature to allow for variation of the focus of the ultrasonic output. Commercially available therapeutic ultrasound devices may be employed in the practice of the invention. The duration and wave frequency, including the type of wave employed may vary, and the preferred duration of treatment will vary from case to case within the judgment of the treating physician. Both progressive wave mode patterns and standing wave patterns have been successful in producing cavitation of diseased tissue. When using progressive waves, the second harmonic can advantageously be superimposed onto the fundamental wave.

Preferred sonodynamic agents employed in the present invention is ultrasound, particularly is low intensity, nonthermal ultrasound, i.e., ultrasound generated within the wavelengths of about 0.1 MHz and 5.0 MHz and at intensities between about 3.0 and 5.0 W/cm$^2$.

Furthermore, it is contemplated that the conjugates of the present invention can be used in combination with photodynamic therapy: By way of example, lutetium texaphyrin is administered in solution containing 2 mg/ml optionally in 5% mannitol, USP. Dosages of about 1.0 or 2.0 mg/kg to about 4.0 or 5.0 mg/kg, preferably 3.0 mg/kg may be employed, up to a maximum tolerated dose that was determined in one study to be 5.2 mg/kg. The texaphyrin is administered by intravenous injection, followed by a waiting period of from as short a time as several minutes or about 3 hours to as long as about 72 or 96 hours (depending on the treatment being effected) to facilitate intracellular uptake and clearance from the plasma and extracellular matrix prior to the administration of photoirradiation.

The co-administration of a sedative (e.g., benzodiazapenes) and narcotic analgesic are sometimes recommended prior to light treatment along with topical administration of Emla cream (lidocaine, 2.5% and prilocaine, 2.5%) under an occlusive dressing. Other intradermal, subcutaneous and topical anesthetics may also be employed as necessary to reduce discomfort. Subsequent treatments can be provided after approximately 21 days. The treating physician may choose to be particularly cautious in certain circumstances and advise that certain patients avoid bright light for about one week following treatment.

When employing photodynamic therapy, a target area is treated with light at about 732±16.5 nm (full width half max) delivered by LED device or an equivalent light source (e.g., a Quantum Device Qbeam™ Q BMEDXM-728 Solid State Lighting System, which operates at 728 nm) at an intensity of 75 mW/cm$^2$ for a total light dose of 150 J/cm$^2$. The light treatment takes approximately 33 minutes.

The optimum length of time following texaphyrin administration until light treatment can vary depending on the mode of administration, the form of administration, and the type of target tissue. Typically, the texaphyrin persists for a period of minutes to hours, depending on the texaphyrin, the formulation, the dose, the infusion rate, as well as the type of tissue and tissue size.

After the photosensitizing texaphyrin has been administered, the tissue being treated is photoirradiated at a wavelength similar to the absorbance of the texaphyrin, usually either about 400-500 nm or about 700-800 nm, more preferably about 450-500 nm or about 710-760 nm, or most preferably about 450-500 nm or about 725-740 nm. The light source may be a laser, a light-emitting diode, or filtered light from, for example, a xenon lamp; and the light may be administered topically, endoscopically, or interstitially (via, e.g., a fiber optic probe). Preferably, the light is administered using a slit-lamp delivery system. The fluence and irradiance during the photoirradiating treatment can vary depending on type of tissue, depth of target tissue, and the amount of overlying fluid or blood. For example, a total light energy of about 100 J/cm$^2$ can be delivered at a power of 200 mW to 250 mW depending upon the target tissue.

One aspect of the present invention is that the compounds of the present invention can additionally be used to image the localization of the therapeutic agent. The texaphyrin core allows for the use of MRI to determine the location of the compound with the patient and determine the specific location and margin of the tumor to which it has localized. In some aspects, the ability to determine the location of the texaphyrin core may be advantageous for more or additional therapeutic methods such as surgery or radiation therapy.

H. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

A=Example 1

General Methods and Materials

1. Materials

Starting materials were purchased from Fisher Scientific or Sigma Aldrich and used without further purification unless otherwise specified. Solvents were purified using a solvent purifier system (Vacuum Atmospheres). Dichloromethane was freshly distilled after being dried over CaH$_2$ under argon. Reaction progress was monitored with Thin Layer Chromatography (TLC) (TLC silica gel 60 F254, Silicycle® UltraPure Silica gels). Texaphyrins and platinum (IV)-texaphyrin conjugates were purified on RP-tC18 SPE (Waters Sep-Pak, waters®) columns containing 10 g of C-18 using increasing gradient of acetonitrile in either 0.1 M ammonium acetate/1% acetic acid aqueous solution or 0.1 M potassium nitrate aqueous solution, depending on which anion (AcO$^{31}$ or NO$_3^-$) was desired as ligands on the gadolinium(III) center. HPLC analyses were performed on a Shimadzu Analytical/Preparative HPLC system equipped with PDA detector and a C18 Acclaim™ 3μm, 120 Å, 2.1×150 mm column (Thermo Scientific). An aqueous (0.1% acetic acid)/acetonitrile (0.1% acetic acid) gradient (30-99% acetonitrile over 20 minutes, 0.3 mL/min) was used for the analysis of all texaphyrin-containing compounds (detection at 470 and 740 nm). For analysis of 5'-GMP and Pt(II)(5'-GMP)$_2$(NH$_3$)$_2$, (0.1% acetic acid)/methanol (0.1% acetic acid) gradient (5-55% methanol over 20 minutes, 0.2 mL/min) was used and the detection was done at 254 nm. Mass spectrometric analyses were carried out in the University of Texas at Austin Mass Spectrometry Facility.

Low-resolution and high-resolution electrospray mass spectrometric (ESI-MS) analyses were carried out using a Thermo Finnigan LTQ instrument and a Qq-FTICR (7 Telsa) instrument, respectively. Elemental analyses were performed by Atlantic Microlabs Inc. $^1$H NMR spectra were recorded using a Varian 400 MHz instrument.

2. General Procedure for EDC.HCl Coupling

Figure 4:
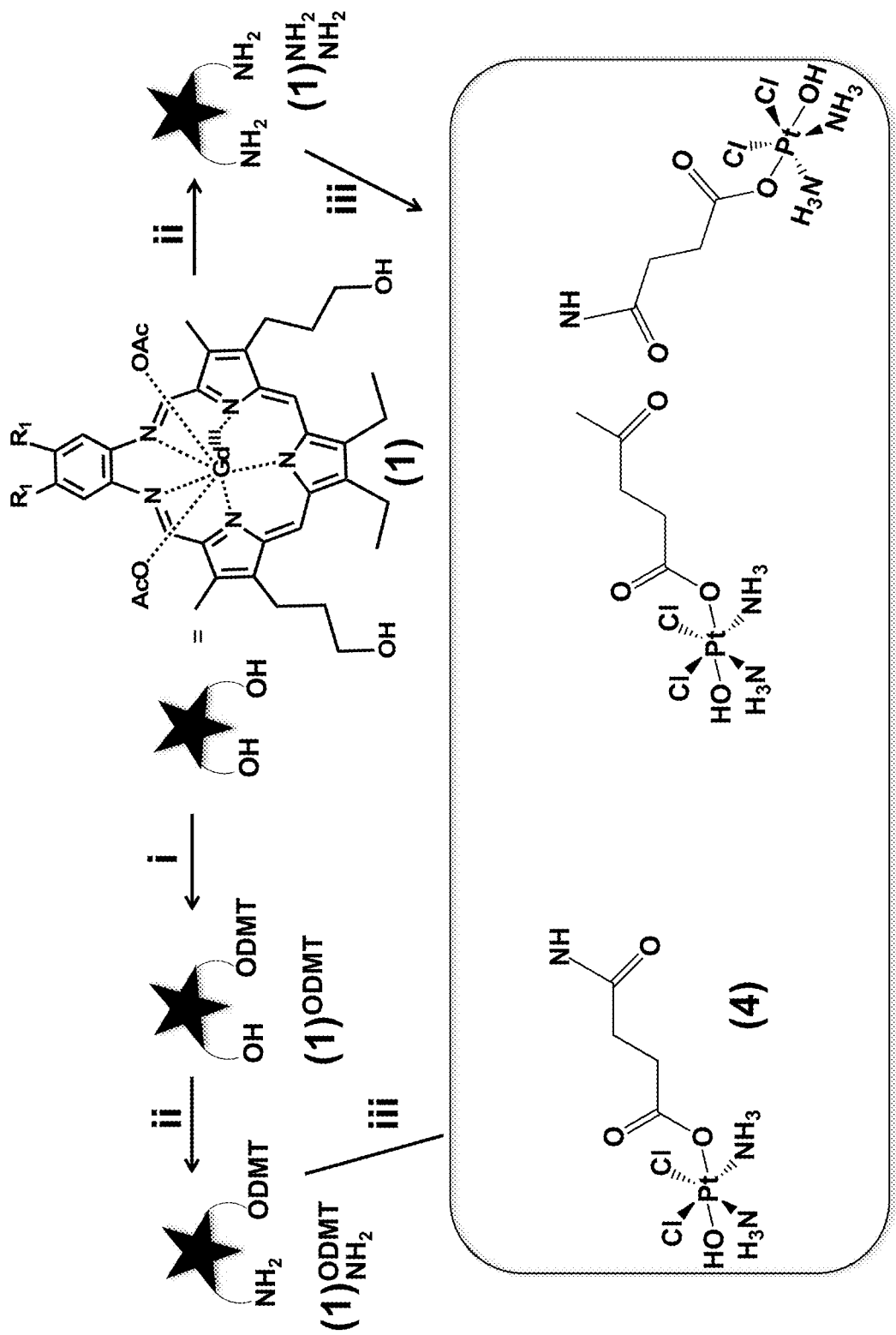
FIG. 4 shows the synthesis of the platinum(IV)-texaphyrin conjugates 4 and 5. R1=(OCH$_2$CH$_2$)$_3$OCH$_3$. Conditions: i=4,4'-dimethoxytriphenylmethylchloride (DMT-Cl), diisopropylethylamine (DIPEA) in dichloromethane, 30%; ii=triphenylphosphine, phthalimide, diisopropylazocaboxylate in dichloromethane, methylamine in methanol/acetonitrile, 25%; iii=N-ethyl-N'-(3-dimethylaminopropyl)carbodiimide hydrochloride (EDC.HCl), —N-hydroxysuccinimide (NHS) and 3 in water. Yields were 40% (4) and 20% (5).

EDC.HCl (40 mg, 0.21 mmol) and N-hydroxysuccinimide NHS (24 mg, 0.21 mmol) were dissolved in HPLC submicron filtered grade water (4 mL). Platinum complex 3 (22 mg, 50 µmol) as a suspension in water (2 mL) was added to the mixture (termed "EDC.HCl+NHS") and left stirring for 30 minutes. Precursor $1^{ODMT}{}_{NH2}$ (60 mg, 42 µmol, RP-HLPC RT=11.4 min) in CH$_3$CN (5 mL) was added dropwise to the previous solution and the reaction mixture was kept in the dark for 20 h at 40° C. The progress of the reaction was monitored by HPLC (a new peak is formed that is characterized by a RT=9 min). KNO3 (50 mL of a 0.1 M aqueous solution) was added and the resulting solution was loaded on a C18 column and subject to elution with increasing gradient of acetonitrile in 0.1 M aqueous KNO$_3$. The isolated fraction was loaded on a new C18 column, desalted with water and eluted with pure methanol. The solvent was removed under vacuum to give the product 4 as a dark green powder. (26.4 mg, 40%). For compound 5, the same procedure was followed. Structures for these compounds can be found in FIG. 4.

3. Light Exposure

For the light-induced release studies, aqueous solutions (of 3 or 4) contained in glass vials were exposed to sunlight in the laboratory behind a window (Viracon®, GL-22), with the following transmittances properties: visible light=38%, UV light (from 300 to 380 nm)=12%. A low vapor pressure mercury lamp was also used. In this latter instance, compound 3 is reduced after 15 minutes exposure whereas conjugate 4 required a 15 hour exposure time to be similarly reduced.

4. Platinum-DNA Binding

Salmon sperm DNA (1.125 mL of 500 µg DNA/mL in Tris-EDTA buffer) was incubated at 37° C. in the dark or exposed to light with platinum complexes (in solution in water; approximately 1 platinum/75 nucleotides as the final ratio). 200 µL aliquots were removed and added immediately to 40 µl of a 10 M aqueous ammonium acetate solution. DNA in samples was precipitated by adding 0.8 mL of absolute ethanol prechilled at −20° C. The samples were left in ice for 1 h and centrifuged at 14000 rpm for 4 minutes. The supernatant was removed carefully and small pellets were dissolved in 50 µL of Tris-EDTA buffer overnight at room temperature. Platinum content was determined by FAAS (model AA300/GTA-96; Varian Instruments, Victoria, Australia) using conditions described by Siddik, et al., 1987 and Siddik and Newman, 1988, which are incorporated herein by reference. Samples were diluted with HCl when the initial Pt concentration was too high. DNA concentrations were determined using a Nanodrop ND-1000 spectrophotometer.

5. Cell Culture

The A2780 line was established from a patient's biopsy prior to initiation of any chemotherapeutic regimen (Godwin, et al., 1992). The resistant cell line, 2780CP, used in this study, was established from A2780 cells, as described by Siddik, et al., 1998. The two cell lines have wild-type p53 genotype and/or function. Cells were grown in RPMI containing 10% fetal calf serum and antibiotics (100 µg/mL streptomycin and 100 U/mL penicillin).

6. Viability Tests

The proliferation of exponential phase cultures of A2780 and 2780CP cells was assessed by tetrazolium dye reduction (Mosmann, 1983, which is incorporated herein by reference). In brief, tumor cells were seeded in 96-well microliter plates at 700 (A2780) and 1000 (2780CP) cells/well, respectively, and allowed to adhere overnight in RPMI 1640 medium supplemented with 2 mM L-glutamine, 10% heat inactivated fetal bovine serum, antibiotics (200 U/cm3 penicillin and 200 µg/cm$^3$ streptomycin). After 24h, drug was added. After a total incubation time of 6 days at 37° C., 50 µL of a stock solution at 3 mg/ml of the tetrazolium dye, 3-(4,5-dimethylthiazol-2-yl)-2,5-diphenyltetrazolium bromide (MTT, Sigma Chemical) were added to each well, the plates incubated at 37° C. for 4 hours, whereupon the medium was removed, the formazan product dissolved in DMSO (50-100 µL) and absorbance values at 570 nm was measured using a microplate reader (Molecular Devices, Sunnyvale, Calif.). Absorbance values were corrected for background and then normalized to wells containing untreated cells to allow plate-to-plate comparisons. The growth inhibition data were fitted to a sigmoidal dose-response curve to generate IC$_{50}$, which is the drug concentration inhibiting cell growth by 50%. The IC$_{50}$ is presented as mean±standard deviation.

Example 2

Chemistry of Texaphyrin Platinum Conjugates

The asymmetric platinum(IV) complex 3, a derivative of cisplatin originally reported by Lippard, (Feazell, et al. 2007; Xiao, et al. 2011; Xiao, et al. 2012; Dhar et al. 2009), was chosen as the platinum precursor for conjugates 4 and 5. This precursor has the advantage that it contains a difunctional succinic acid moiety that can both serve as the axial ligand for the Pt(IV) center and allow facile conjugation to an amino-functionalized texaphyrin core. Moreover, the presence of an electron-donating hydroxy ligand in the other axial position of complex 3 was expected to make conjugates derived from it more stable than analogues containing carboxylato or halo ligands about the Pt(IV) center, which are known to undergo rapid hydrolysis under biologically relevant conditions (Wexselblatt, et al. 2013).

The synthesis of conjugates 4 and 5 is shown in Scheme 2. Briefly, the mono- and bis-amine derivatives of MGd 1 (Wei, et al. 2005) were subjected to carbodiimide coupling conditions in the presence of the Pt(IV)-containing precursor 3; after purification, this gave conjugates 4 and 5 in yields of 40% and 20%, respectively.

Figure 6:
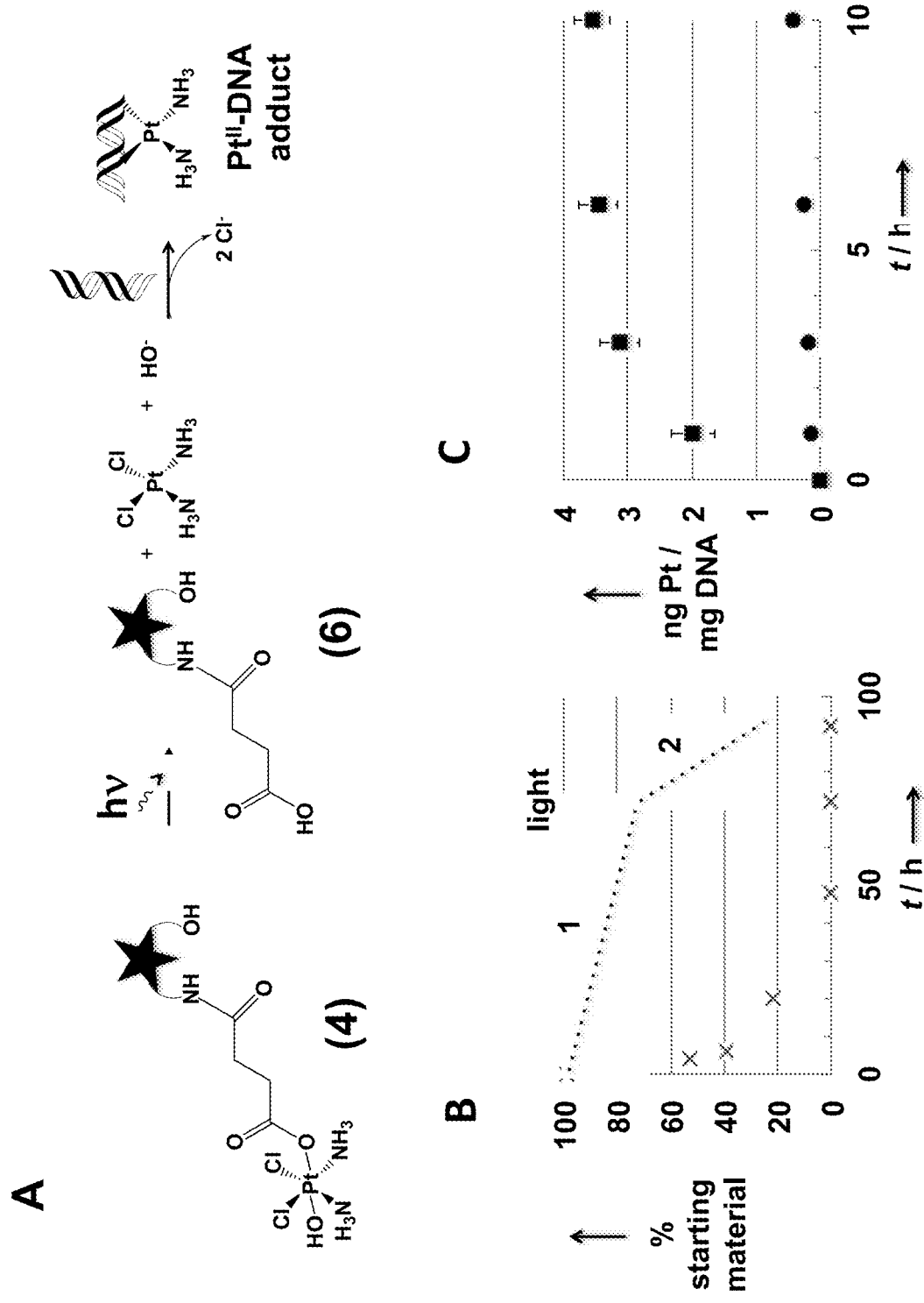
FIGS. 6A-C show the (FIG. 6A) Schematic representation of the photo-activation of 4 followed by formation of a DNA-Pt adduct. Note: The star represents the texaphyrin moiety.
Figure 7:
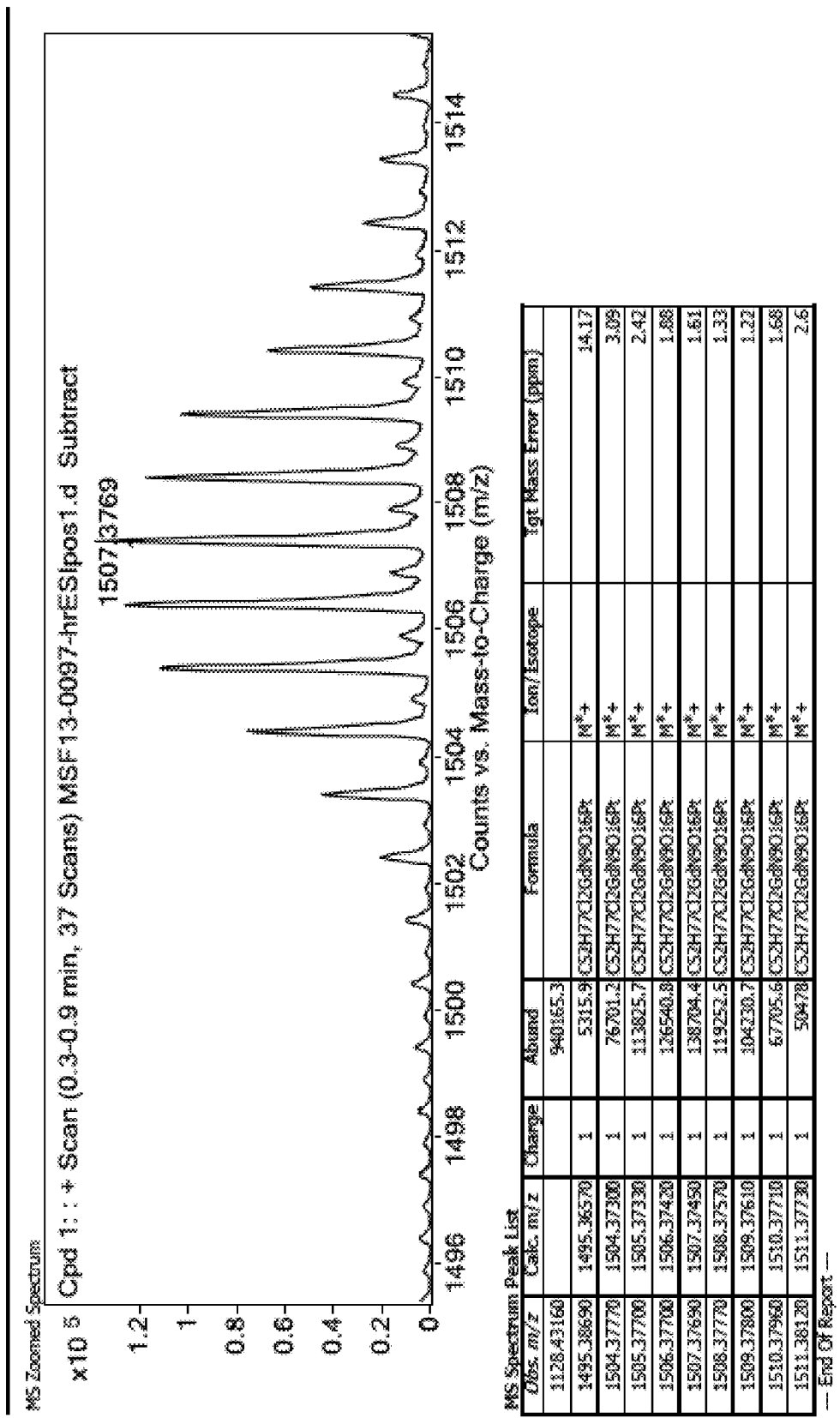
FIG. 7 shows the high-resolution ESI-MS spectrum of 4 recorded from an aqueous sample.
Figure 10:
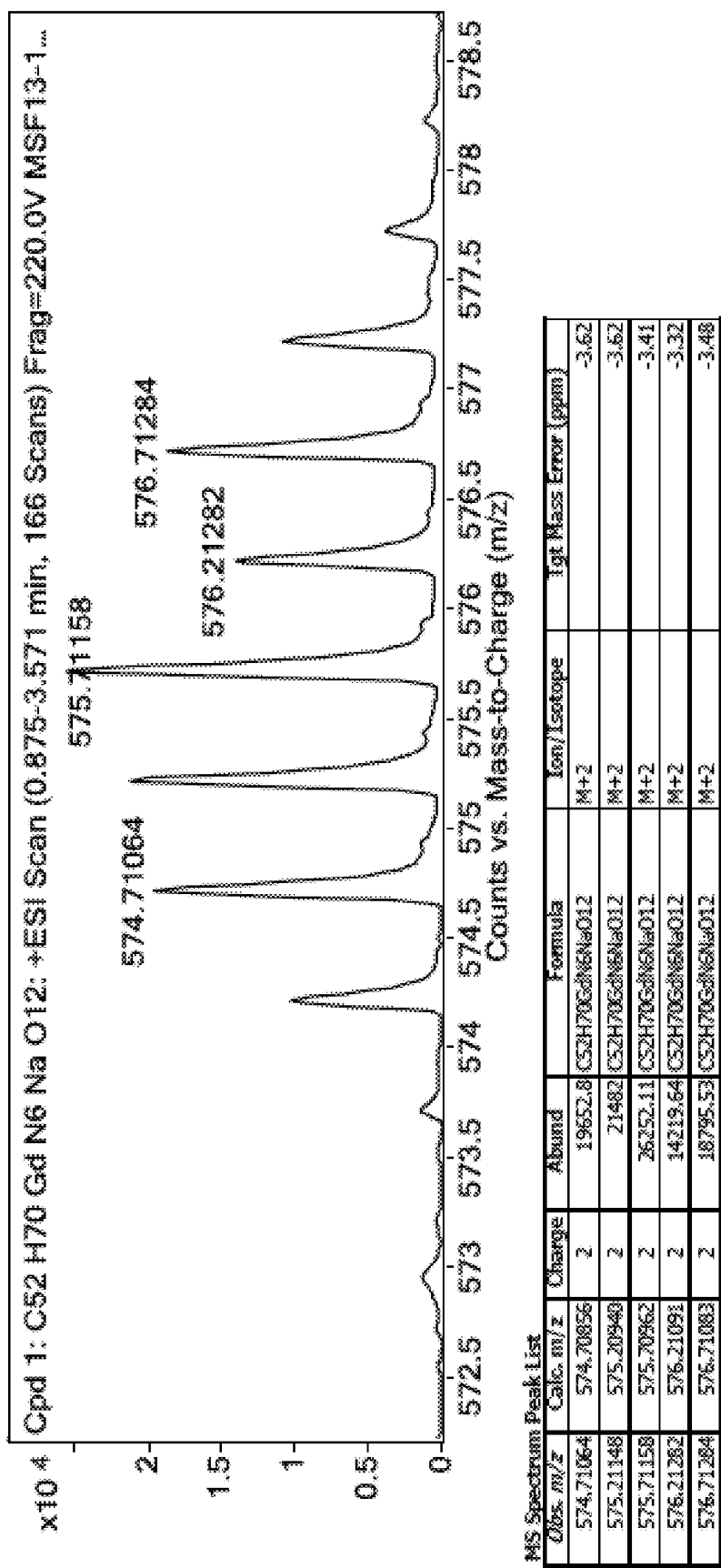
FIG. 10 shows the high-resolution spectrum of 6 (zoomed on the major peak).
Figure 11:
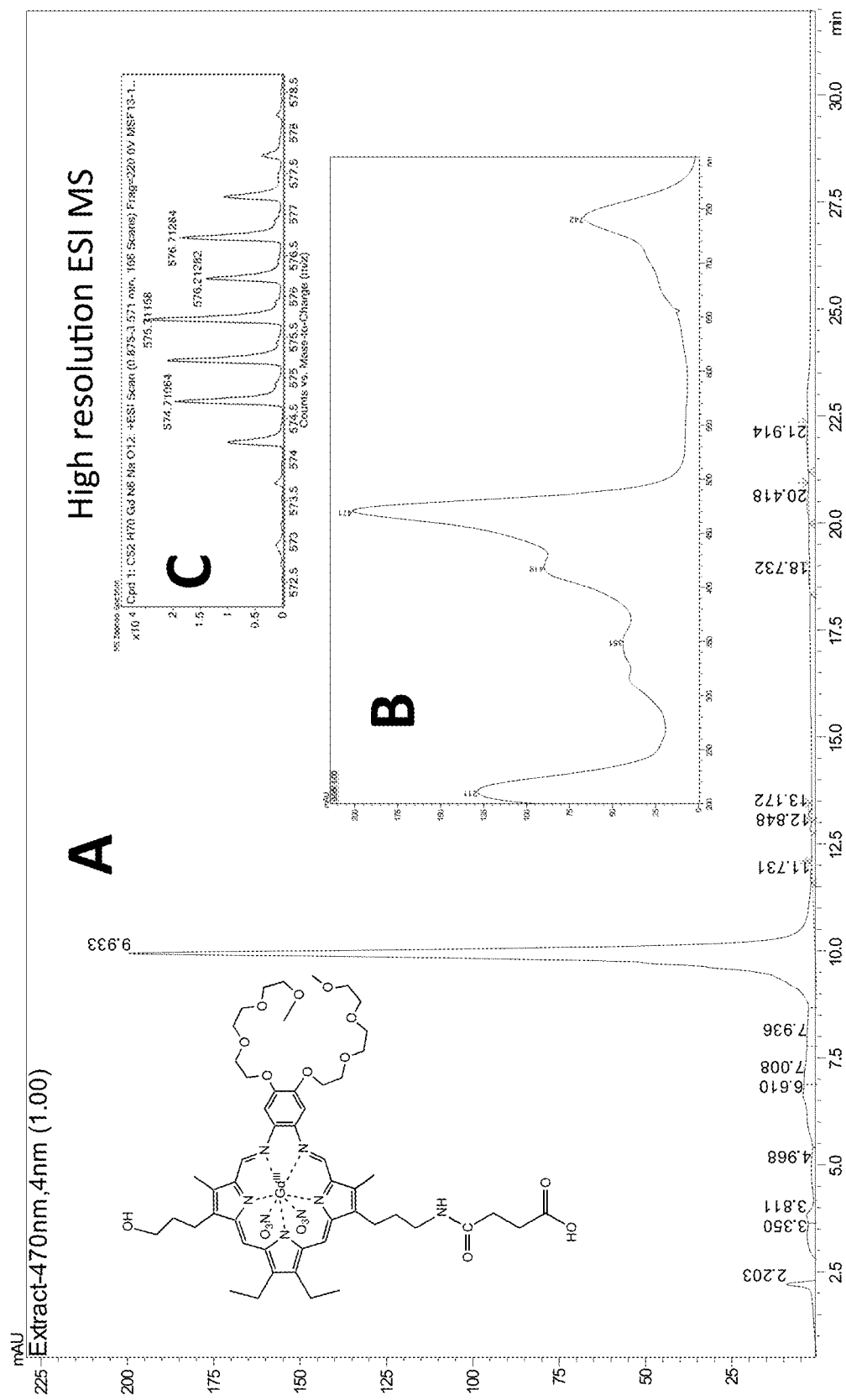
FIGS. 11A-C show RP-HPLC chromatogram monitored at 470 nm (FIG. 11A) and UV-vis spectrum (FIG. 11B) of 6 recorded in water.
Figure 12:
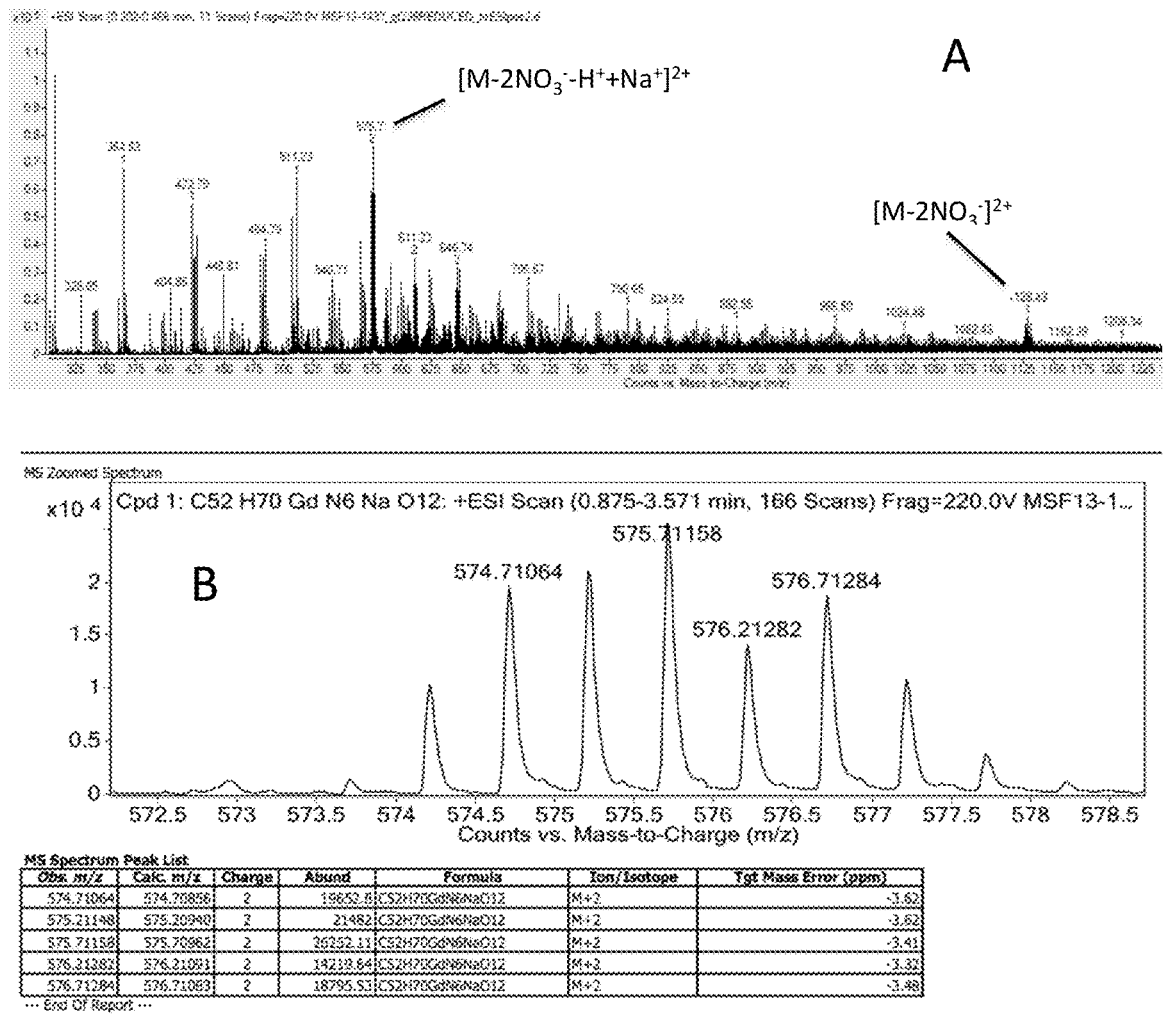
FIGS. 12A & B show the high resolution ESI-MS spectrum of 6 obtained after exposing 4 to laboratory light (2 days) (FIG. 12A); magnified view of the most intense peak (FIG. 12B). Note: the same results were observed after reaction of 4 with sodium ascorbate or glutathione.

Conjugate 4 is highly soluble in water. Its stability towards hydrolysis could thus be evaluated using RP-HPLC. This was done by monitoring the decrease in the absorption intensity at 470 nm (Abs$_{470}$), a peak corresponding to the starting material 4 (FIG. 6). On the basis of these studies, which were carried out in aqueous media at 310 K while minimizing exposure to light, it was concluded that conjugate 4 possesses greater hydrolytic stability ($t_{1/2}$>3 days) than the first generation platinum(II) conjugate, cisTEX (2) ($t_{1/2}$=12 h) when tested under the same conditions. Without being bound by theory, this greater kinetic stability can be attributed to the relative inertness of the platinum(IV) complex present in conjugate 4.

Studies were undertaken to investigate the photosensitivity of the Pt(IV) moiety within conjugate 4. Without being bound by theory, Pt(IV) complexes are hypothesized to lose both axial ligands upon reduction (Wexselblatt and Gibson, 2012; Wexselblatt, et al., 2012; Sinisi, et al. 2010; Nemirovski, et al., 2010). In the case of 4, loss of both axial ligands (i.e., the hydroxyl ligand and the texaphyrin-bearing succinate) would give rise to texaphyrin 6 and cisplatin. After exposure to glass-filtered daylight (see Example 4.1), the starting material is transformed ($t_{1/2}$=5 h, ca. 100% after 48 h) to a new compound that on the basis of mass spectrometric and RP-HPLC analyses corresponds to what would be expected for the succinic acid-functionalized texaphyrin 6 (FIG. 6). This daughter compound (6) was independently synthesized, allowing for direct co-injection studies.

Figure 17:
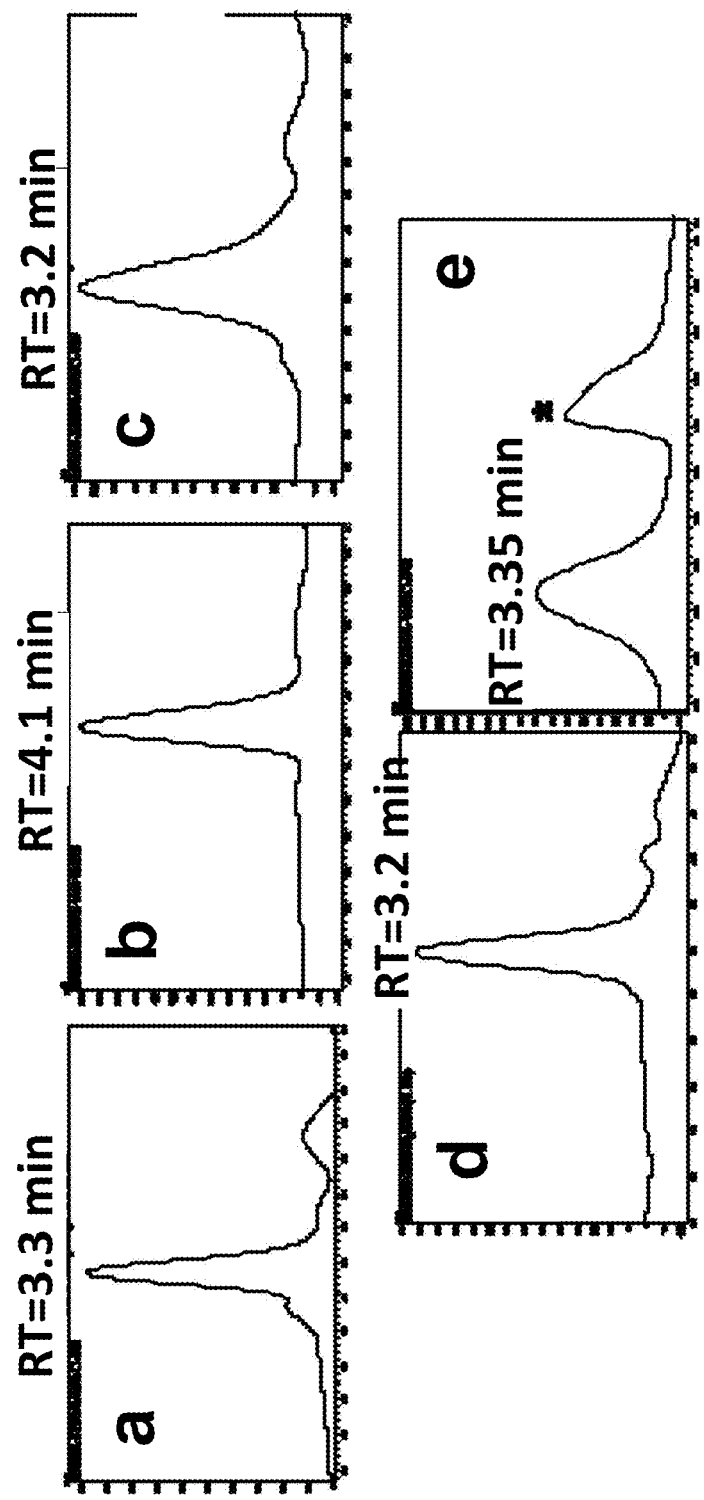
FIGS. 17A-E show the RP-HPLC traces of cisplatin (FIG. 17A), 3 in the dark (FIG. 17B), 3 after being exposed 48 hours to ambient light (FIG. 17C), 4 after 48 hours light exposure (FIG. 17D), 4 after 1 hour reaction with sodium ascorbate (5 equiv.) FIG. 17E * Peak corresponding to sodium ascorbate.
Figure 18:
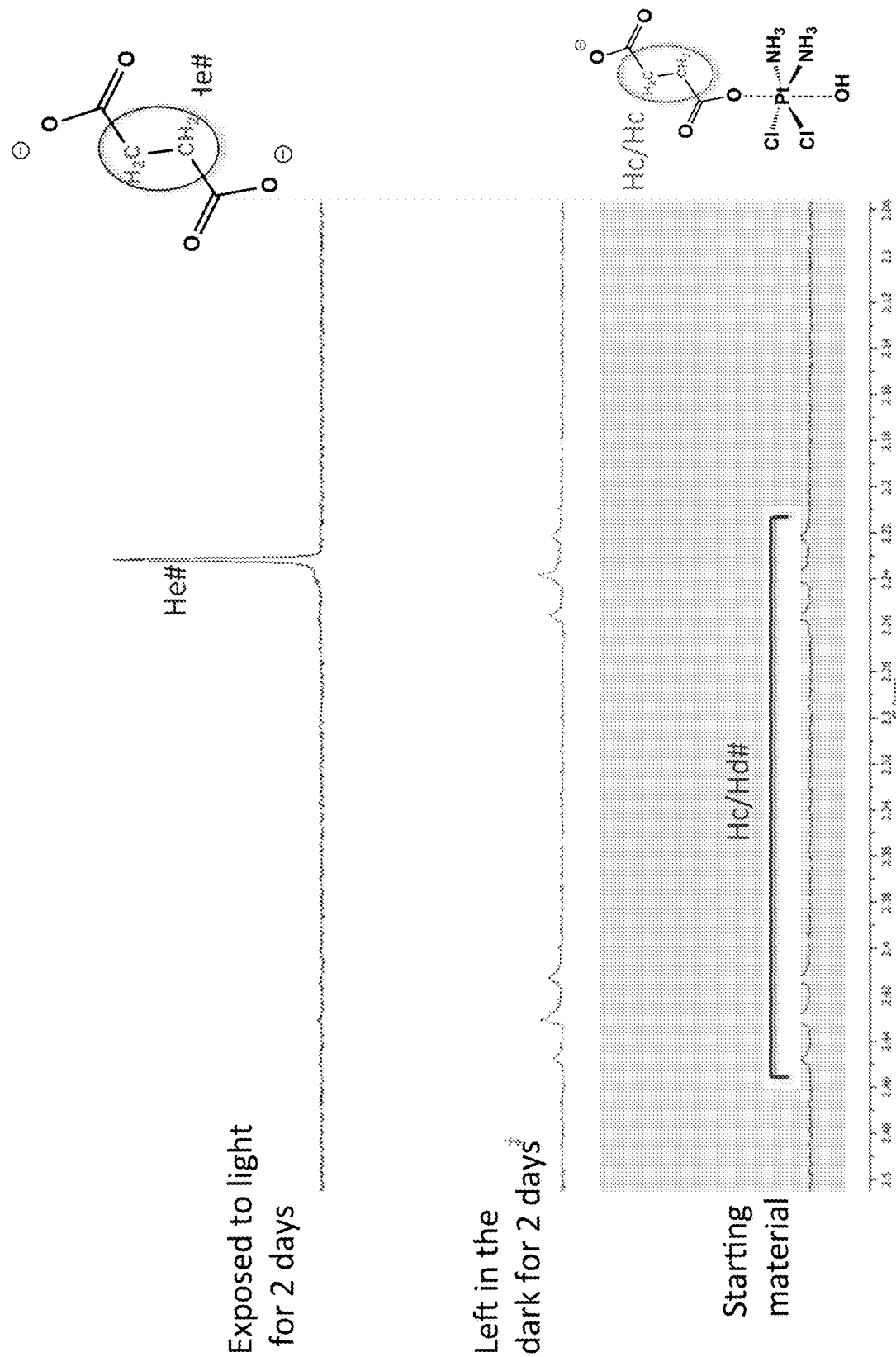
FIG. 18 shows the $^1$H-NMR (D$_2$O PBS solution pH=7.5, 300 K, 400 MHz) spectra of 3 recorded before and after exposure to laboratory light, showing the release of succinate anion (He#).

Texaphyrin 6 was also obtained when the Pt(IV) conjugate 4 was subject to reduction using the known biological reductants, sodium ascorbate (NaAsc) and glutathione (GSH). The other reduction product, namely cisplatin, was identified using RP-HPLC after being separated from 6 on a C18 RP HPLC column (FIG. 17).

Figure 20:
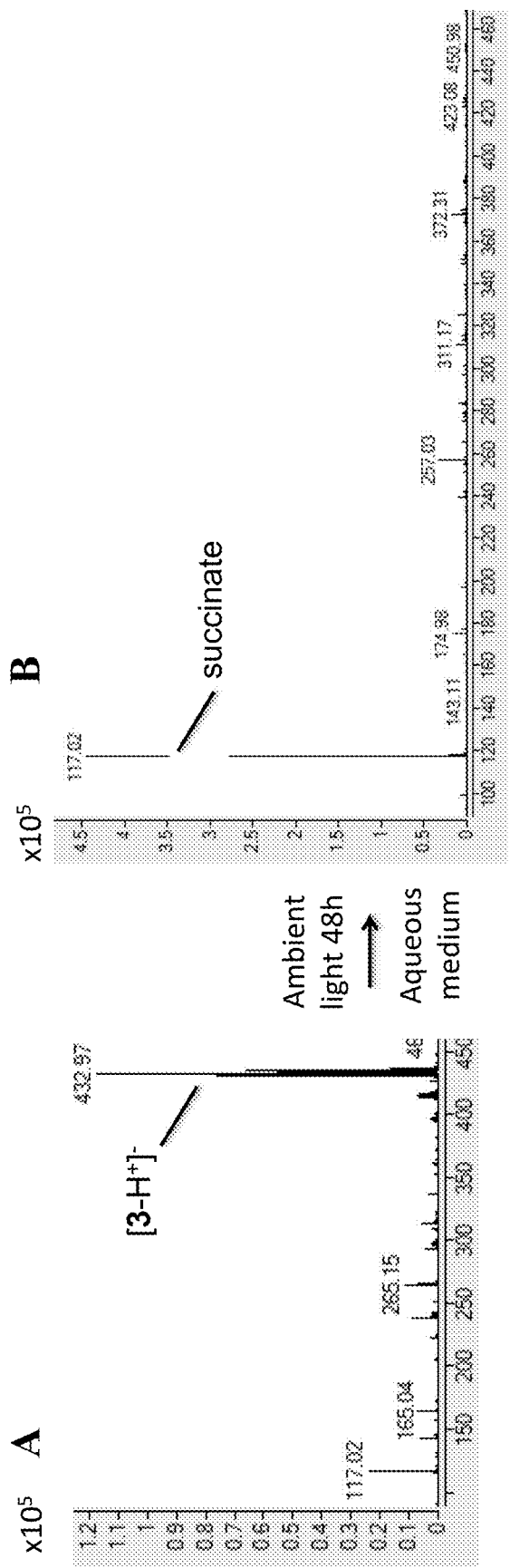
FIGS. 20A & B show the ESI-MS (negative mode, PBS solution) spectra of 3 before (FIG. 20A) and after 48h light exposure (FIG. 20B) showing the release of succinate anions after light exposure.

In an effort to understand further the chemistry of Pt(IV) as it bears on conjugates 4 and 5, $^1$H-NMR spectroscopy was used to probe the effect of light on the texaphyrin-free Pt(IV) complex 3. The choice of 3, rather than 4 or 5, was dictated by the paramagnetic nature of these latter species. The spectrum of 3 was recorded in $D_2O$ and is characterized by two triplets at 2.58 and 2.38 ppm corresponding to the four asymmetric methylene protons present in the axially coordinated succinate. In the dark, no change in the spectrum was observed, even after one week. This finding is in line with the comparatively high hydrolytic stability of 4 noted above. In contrast, when precursor 3 was exposed to glass-filtered daylight for 2 days, the two triplets originally present in the spectrum were seen to coalesce into a singlet at 2.39 ppm. This final spectrum corresponds to that of the free succinate anion in water. It was also possible to detect the released succinate anion by ESI-MS analysis (FIG. 20). Taken in concert, these findings suggest that compound 3 is similar to 4 in that exposure to ambient light induces release of the axial succinate ligand. Without being bound by theory, the observation supports the conclusion that the presence of the texaphyrin localizing group is not necessary to trigger axial ligand release.

Figure 21:
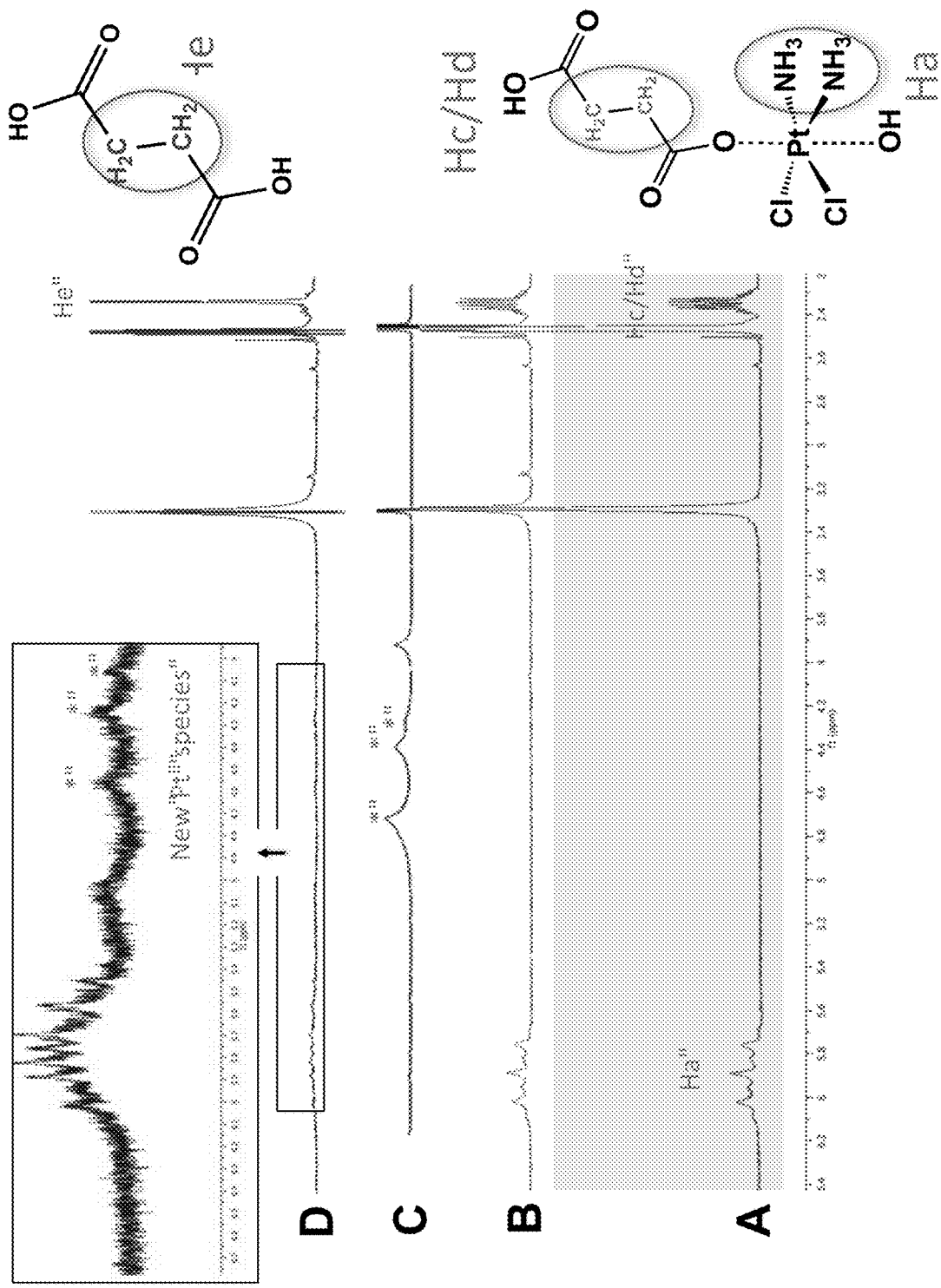
FIG. 21 shows the $^1$H-NMR (DMSO, 300 K, 400 MHz) spectra of 3 before letting sit (A) in the dark for 22 h (B) and (D) after being exposed for 48h to ambient light, showing the release of succinic acid (He) and formation of new species (red stars). The spectrum C corresponds to cisplatin in DMSO. Note: It is known that DMSO interacts with Pt(II) (Fischer, et al., 2008), a finding that explains the NMR spectral profiles observed in (C) and (D). Support for this expected interaction was provided by subjecting this solution to ESI-MS analysis as described in FIG. 22
Figure 22:
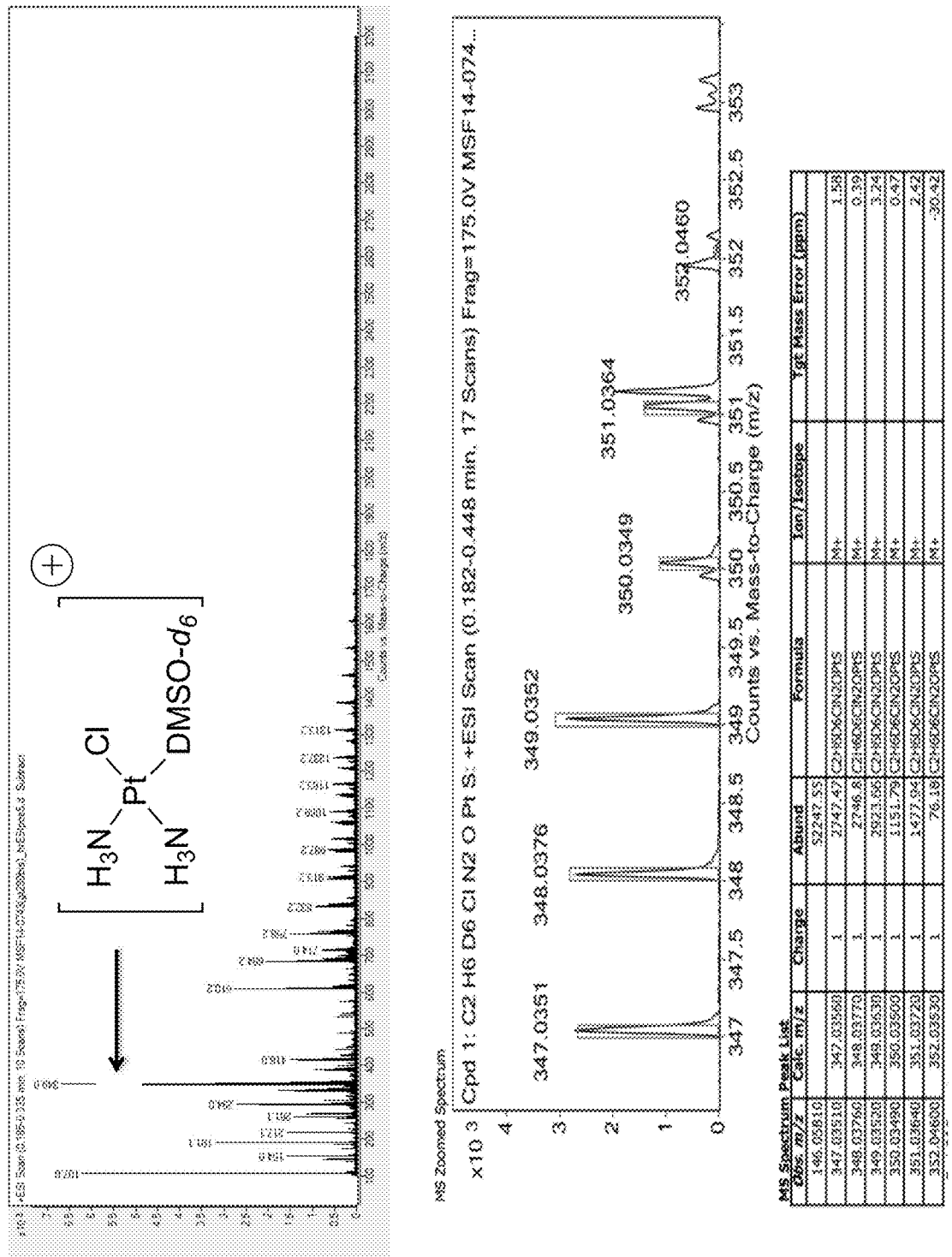
FIG. 22 shows the high resolution ESI-MS spectrum of 3 in DMSO-d$_6$ (solution used for NMR studies) after being exposed for 2 days to ambient light.

An analogous $^1$H NMR spectral experiment using 3 in DMSO allowed the peaks corresponding to the coordinated $NH_3$ protons to be monitored. After exposure of 3 to ambient light for 2 days, the initial signals at 5.8 ppm decrease in intensity, while new peaks between 4 and 5.3 ppm appear that are characteristic of a Pt(II) species. These new peaks are similar to those observed when cisplatin is solubilized in DMSO (FIG. 21). Analysis of this solution by ESI-MS reveals signals corresponding to $[Pt(II)(NH_3)_2(Cl)(DMSO)]^+$ (FIG. 22).

Figure 5:
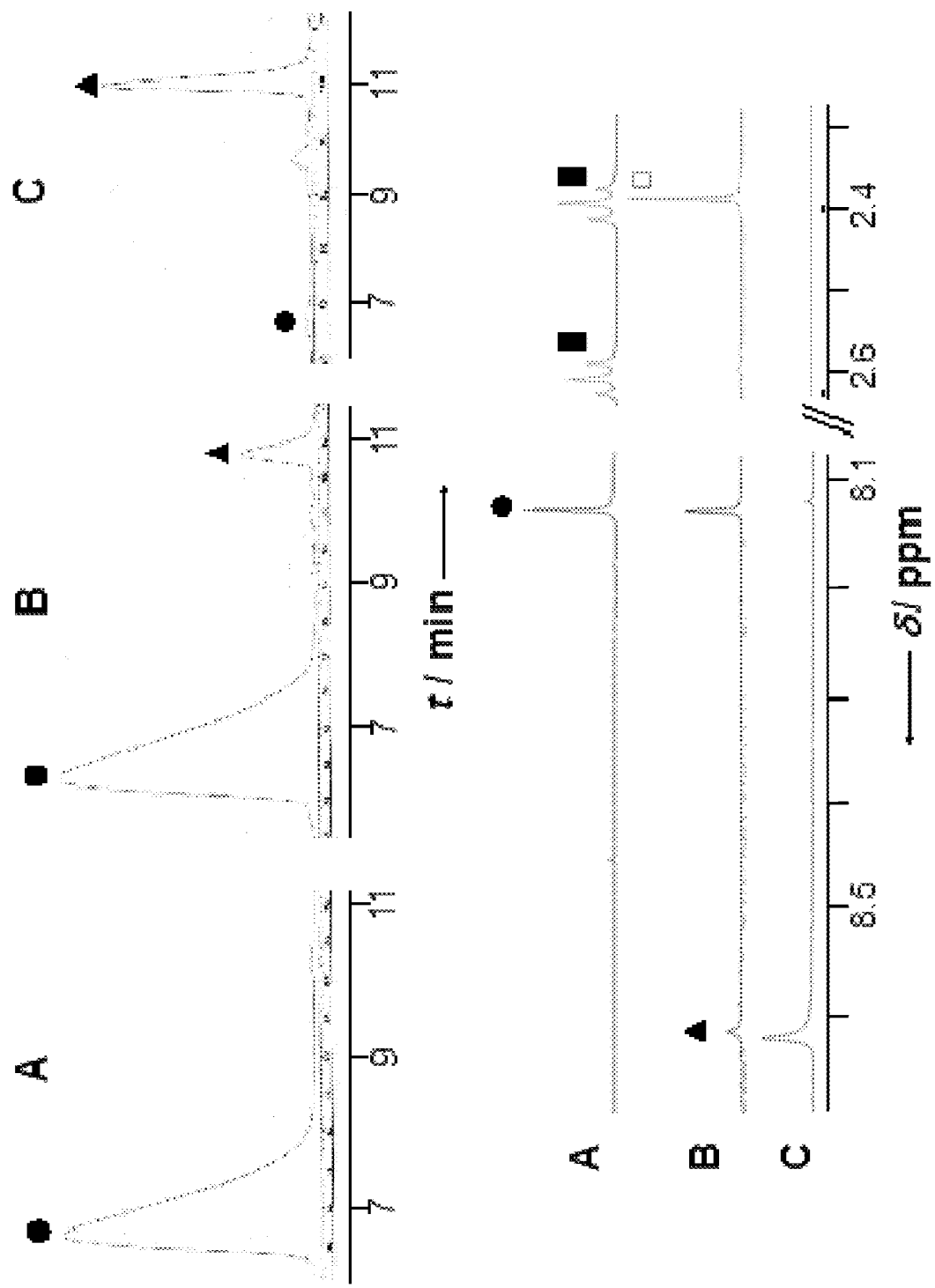
FIG. 5 shows a partial RP-HPLC chromatograms (top) and $^1$H-NMR spectra (bottom, D$_2$O, pH=7, 300 K, 400 MHz) of complex 3 recorded in the presence of 5'-GMP (2 equiv.) before (A) and after being exposed to laboratory light for 2 days (B); (C) cisplatin incubated in presence of 5'-GMP (2 equiv.) for 10 h at 37.C; circle =free 5'-GMP; triangle=Pt(II)-coordinated 5'-GMP; black square =Pt(IV)-coordinated succinate anion; square=free succinate dianion.

Guanosine 5'-monophosphate (5'-GMP) was used as a trapping agent for Pt(II). In the dark, no change was observed in the $^1$H-NMR spectrum (and RP-HPLC chromatogram) of 3 even after incubating for one-week in the presence of 5'-GMP. Nor were changes in the spectrum of 5'-GMP observed. The lack of change can be taken as evidence that this Pt(IV) complex does not bind to 5'-GMP. In contrast, after exposure to light for 2 days, a new peak is observed at 8.6 ppm (FIG. 5, triangle). This peak appears at high frequency, as is typical for the $H^8$ resonance of 5'-GMP in complexes where a diamagnetic cation is coordinated to $N^7$ of 5'-GMP (Berners-Price, et al. 1994; Berners-Price, et al. 1993). This new signal was comparable to the signal obtained when sodium ascorbate was added to a mixture of 3 +5'-GMP or when cisplatin was added to 5'-GMP (FIG. 5C).

The solutions used for the NMR spectral studies were also analyzed by RP-HPLC. As can by seen by inspection of the upper part of FIG. 5, a new peak appeared after exposing a mixture 3+5'-GMP to ambient light for 2 days. This peak has the same retention time (10.9 min) as does the complex formed between cisplatin and 5'-GMP. This leads us to suggest that the same 5'-GMP - Pt(II), complex, namely the known adduct $(5^1$-GMP$)_2$-Pt(II)-$(NH_3)_2$, (Choi, et al., 1998; Van der Veer, et al. 1986; Roat, et al. 1993; Choi, et al. 1999; Zöllner, et al. 2001) is formed upon light-induced reduction of 3.

The influence of light on the interaction between 4 and DNA was also investigated (Shi, et al. 2012). It was observed that when 4 is exposed to ambient light, 8.5 ±1.1 times more DNA-Pt adducts are formed (average of 2 independent studies) than when 4 is kept in the dark (see FIG. 6C).

The anti-proliferative effects of conjugates 4 and 5 were assessed with platinum sensitive human ovarian A2780 cells and the isogenic cisplatin resistant 2780CP cell line. These experiments were carried out in the dark at 37° C. for conjugate 4. Colorimetric cell proliferation assay results (Table 1) lead us to conclude that these new platinum(IV) conjugates are more efficient in inhibiting cancer cell growth in both cell lines than the first generation conjugate cisTEX (2). This enhancement in efficacy is fully consistent with the suggestion that the greater hydrolytic stability of 4 and 5 compared to 2 serves to increase the effective concentration of Pt(II) at locales where it is most effective. The potency of conjugate 5 is roughly equal to that of conjugate 4 on a per platinum basis.

TABLE 1

Half maximal inhibitory concentrations ($IC_{50}$) (micromolar) determined for the Pt(IV)-TEX conjugates 4 and 5, and the texaphyrin-free platinum (IV) precursor complex 3. Also given are data for the platinum(II) complexes cisplatin and cisTEX (2).

| Compounds | $IC_{50}$ 2780CP | $IC_{50}$ A2780 | Resistance factor[b] |
|---|---|---|---|
| Cisplatin[a] | 7.3 (0.2) | 0.33 (0.02) | 18.25 |
| 2[a] | 17.0 (1.5) | 1.63 (0.20) | 10.42 |
| 3 | 26.88 (2.04) | 6.31 (0.38) | 4.26 |
| 4 | 10.66 (0.63) | 1.28 (0.12) | 8.32 |
| 5 | 4.55 (0.29) | 0.67 (0.06) | 6.79 |

[a]See Arambula, et al., 2012.
[b]Resistance factor = $IC_{50}$(2780CP)/$IC_{50}$(A2780)

Example 3

Synthesis of Texaphyrin Platinum Complexes

1. Platinum Complexes

Cis-cis-trans-Pt(IV)$(Cl)_2(NH_3)_2$ $(OH)_2$ (oxoplatin): Cisplatin (100 mg, 0.33 mmol) was dissolved in 1.5 mL of deionized water. $H_2O_2$ (4 mL; 30% in water) was added drop-wise and the mixture was heated at 60° C. overnight in the dark. The solution was then cooled to room temperature and placed in a refrigerator for 1 h. A light yellow powder (or crystals under conditions of very slow cooling overnight) is obtained. The solid was collected by filtration using 0.8 μM isopore™ membrane filters (Millipore), rinsed with cold water and dried under vacuum. The product (60 mg, 54%) was characterized by ESI-MS and IR spectroscopy and the data correspond to those reported in Kuroda, et al., 1983, which is incorporated herein by reference. ESI-MS: positive mode: 300 [M−Cl⁻]⁺ and 356.9 [M+Na⁺]; FTIR: 3460 and 540 cm$^{-1}$ (O—H and Pt—OH bond stretching).

Cis-cis-trans-Pt(IV)(Cl)$_2$(NH$_3$)$_2$(OH)(OOC—CH$_2$—COOH) (3): Oxoplatin (60 mg, 0.18 mmol) was dissolved in dry DMSO (5 mL) and succinic anhydride (18 mg, 0.18 mmol) was added. The reaction mixture was stirred under N$_2$ in the dark overnight. The solution containing some insoluble material was filtered a first time using a PTFE membrane filter, which was then washed with cold acetone. To the filtrate was added a further aliquot of cold acetone (V$_{total}$=500 mL). The filtrate was then left in an ice cold bath in the dark for 2 h. A very thin suspension formed. This was collected by filtration using another PTFE membrane filter, washed with cold acetone and dried under vacuum. The product (54 mg, 69%) was characterized by ESI-MS (high resolution), $^1$H NMR spectroscopy, IR spectroscopy, and elemental analysis. The characterization data correspond to those reported in Johnstone, et al., 2013, which is incorporated herein by reference: ESI-MS: Positive mode: 416.97 [M–OH⁻]⁺, 434.98 [M+H⁺]⁺, 456.97 [M+Na⁺]⁺; Negative mode: 432.97 [M–H⁺]⁻, 468.94 [M+Cl⁻]⁻; $^1$H-NMR (DMSO-d$_6$, 300 K, 400 MHz): 2.3 ppm (4H, m, —CH$_2$), 5.8 ppm (6H, m, NH$_3$). Note: In D$_2$O, the NH$_3$ signals are not visible. However, the signals from the coordinated succinic acid moiety are better differentiated than in DMSO-d$_6$ (two triplets each integrating for 2H at 2.38 and 2.58 ppm). Elemental analysis: Calcd for C$_4$H$_{12}$Cl$_2$N$_2$O$_5$Pt: C 11.07, H 2.79, Cl 16.33, N 6.45; found: C 11.83, H 2.88, Cl 15.62, N 6.35.; and FT-IR: 3460, 1700, 1640, 540 cm$^{-1}$. Note: IR absorption features corresponding to the presumed O—H bond stretching mode (3460 cm$^{-1}$) are maximal for oxoplatin, intermediate for complex 3, and absent for cisplatin. The same order is observed for the Pt—OH bond stretching features (540 cm$^{-1}$). For complex 3, peaks at 1640 and 1700 cm$^{-1}$, characteristic of coordinated and free carboxylic acid groups, respectively, are observed.

2. Texaphyrins:
    1=MGd*
    $1^{ODMT}$=MGd(OH)(ODMT)*
    $1^{ODBT}{}_{NH2}$=MGd(NH$_2$)(ODMT)*
    $1^{NH2}{}_{NH2}$=MGd(NH$_2$)(NH$_2$)
    4=MGd(3)
    5=MGd(3)$_2$
    6=MGd(succinic acid)
    * known compounds whose synthesis are already published (Wei, et al., 2005)

$1^{NH2}{}_{NH2}$: To a round bottom flask containing triphenylphosphine (685 mg, 2.6 mmol) was added phthalimide (384.5 mg, 2.6 mmol) and 1 (500 mg, 0.287 mmol) in one batch, both of which starting materials were previously dried overnight under vacuum. To this mixture was added 100 mL of freshly distillated CH$_2$Cl$_2$ (dried over CaH$_2$). The resulting green solution was cooled over ice for about 15 minutes under Na. Following this, diisopropylazocarboxylate (514 µL, 2.6 mmol) was added drop-wise. The reaction mixture was kept over ice for 2-3 hours and allowed to warm slowly to ambient temperature. The solvent was removed under reduced pressure. To the resulting residue, was added 30 mL of methanol, 10 mL of acetonitrile (to increase the solubility) and 27 mL of methylamine (40% in water). After 7 hours of stirring at ambient temperature, N$_2$ was bubbled through the reaction mixture to remove excess methylamine. The volatiles were then removed under reduced pressure and the resulting solids were resuspended in 20 mL of acetonitrile and 80-100 mL of an aqueous 0.1 M ammonium acetate/1% acetic acid solution. The resulting solution was loaded on a C-18 column and purified by chromatography using an increasing gradient of acetonitrile/0.1 M aqueous ammonium acetate +1% acetic acid while monitoring by HPLC (RT=6.9 min). The product was loaded on a new C-18 column, desalted by rinsing with HPLC grade submicron filtered water, eluting with methanol, and drying under reduced pressure. This gave a dark green powder (140 mg, 24%). Notes: The published protocol for $1^{NH2}{}_{NH2}$ (Wei, et al., 2005, which is incorporated herein by reference) recommends extracting the products with chloroform after deprotection by methylamine. However, in the case of $1^{NH2}{}_{NH2}$ this protocol is not effective because the product remains in the aqueous layer. Therefore, the crude material was loaded immediately onto the C18 column. Before being coupled with 3, $1^{NH2}{}_{NH2}$ was solubilized in a mixture of acetonitrile and 0.1 M aqueous KNO$_3$ in order to exchange the acetate ligands for nitrate. The resulting solution was loaded on a new C18 column and as described above, desalted with water, eluted off the column using methanol, and then dried under reduced pressure.

3. Conjugates TEX-Pt(IV):

$4_{NO3}$=MGd(OH)(3): EDC.HCl (40 mg, 0.21 mmol) and N-hydroxysuccinimide NHS (24 mg, 0.21 mmol) were dissolved in HPLC submicron filtered grade water (4 mL). Complex 3 (22 mg, 50 µmmol) as a suspension in water (2 mL) was added to the mixture (termed "EDC.HCl+NHS") and left stirring for 30 minutes. Precursor $1^{ODMT}{}_{NH2}$ (60 mg, 42 µmmol, HLPC RT=11.4 min) in CH$_3$CN (5 mL) was added drop-wise to the previous solution and the reaction mixture was kept in the dark for 20 h at 40° C. The progress of the reaction was monitored by HPLC (a new peak is formed that is characterized by a RT=9 min). Following this period, KNO$_3$ (50 mL of a 0.1 M aqueous solution) was added and the resulting solution was loaded onto a C18 column and subject to elution with increasing gradient of acetonitrile in 0.1 M aqueous KNO$_3$. The isolated fraction was loaded onto a new C18 column, desalted with water and eluted with pure methanol. The solvent was removed under vacuum to give the product as a dark green powder (26.4 mg, 40%). The non-platinated compound, MGd(OH)(NH$_2$) (the DMT group was deprotected by HCl), is isolated during the purification. This latter species was used in another coupling reaction. Note: During this coupling, a trace of 6 (ca. 5%; RT=9.99 min) is formed, as inferred from the HPLC analysis. Sometimes it proved difficult to drive the reaction to completion. However, this is not problematic since the non-platinated species $1^{OH}{}_{NH2}$ (the DMT group was removed by HCl) is relatively easy to separate using a C18 column. Once isolated, the product was analyzed by high resolution ESI-MS; as shown in FIGS. 5, 6A & B, and 7A & B. Elemental analysis: Calcd for C$_{52}$H$_{77}$Cl$_2$GdN$_{10}$O$_{19}$Pt: C 39.79, H 4.95, Cl 4.52, N 8.92; found: C 39.07, H 4.97, Cl 4.17, N 8.90.

(6) MGd(OH)(succinic acid): This compound can be obtained by either reducing the platinum(IV) center within the conjugate 4 (light, sodium ascorbate or glutathione) or from the reaction between $1^{ODMT}{}_{NH2}$ and succinic acid. In this latter instance, $1^{ODMT}{}_{NH2}$ (20 mg, 13.7 µmol) in acetonitrile (50 mL) was added slowly and drop-wise into a solution containing succinic acid (1.6 g, 13.7 mmol), EDC.HCl (2.6 g, 13.7 mmol) and NHS (1.53 g, 13.7 mmol) in HPLC submicron filtered grade water (150 mL). The reaction was stirred overnight under N$_2$. The reaction progress was checked by TLC (silica gel plates; 80/20 CH$_2$Cl2/MeOH, eluent) with Rf $1^{ODMT}{}_{NH2}$=0 and Rf $6^{ODMT}$=0.57. The solution was loaded on a C18 column and the product was purified using an increasing gradient of acetonitrile in an aqueous solution of 0.1 M ammonium acetate +1% acetic acid. The protected intermediate ($6^{ODMT}$) was desalted using submicron filtered HPLC grade water, eluted with methanol and dried under reduced pressure. To deprotect the DMT group, $6^{ODMT}$ was dissolved in 2 mL of dichloromethane and 1.5 mL of acetic acid were added. The solution was stirred for 3 h and checked by TLC (silica gel plates; 80/20 $CH_2Cl_2$/MeOH, eluent). The rf of 6=0.34. The product was purified on a C18 column as above (yield: 6.6 mg, 40%). Characterization is shown in FIGS. 10, 11A-C, and 12A & B.

Figure 13:
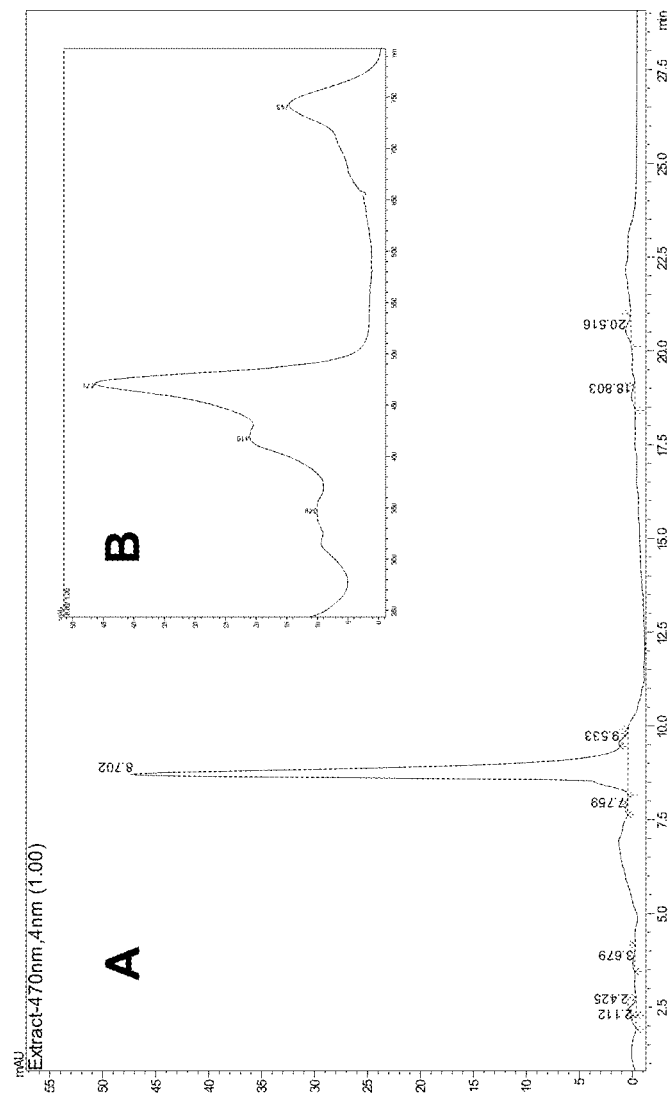
FIGS. 13A & B show the RP-HPLC chromatogram monitored at 470 nm (FIG. 13A) and UV-vis spectrum (FIG. 13B) of conjugate 5 in water.
Figure 14:
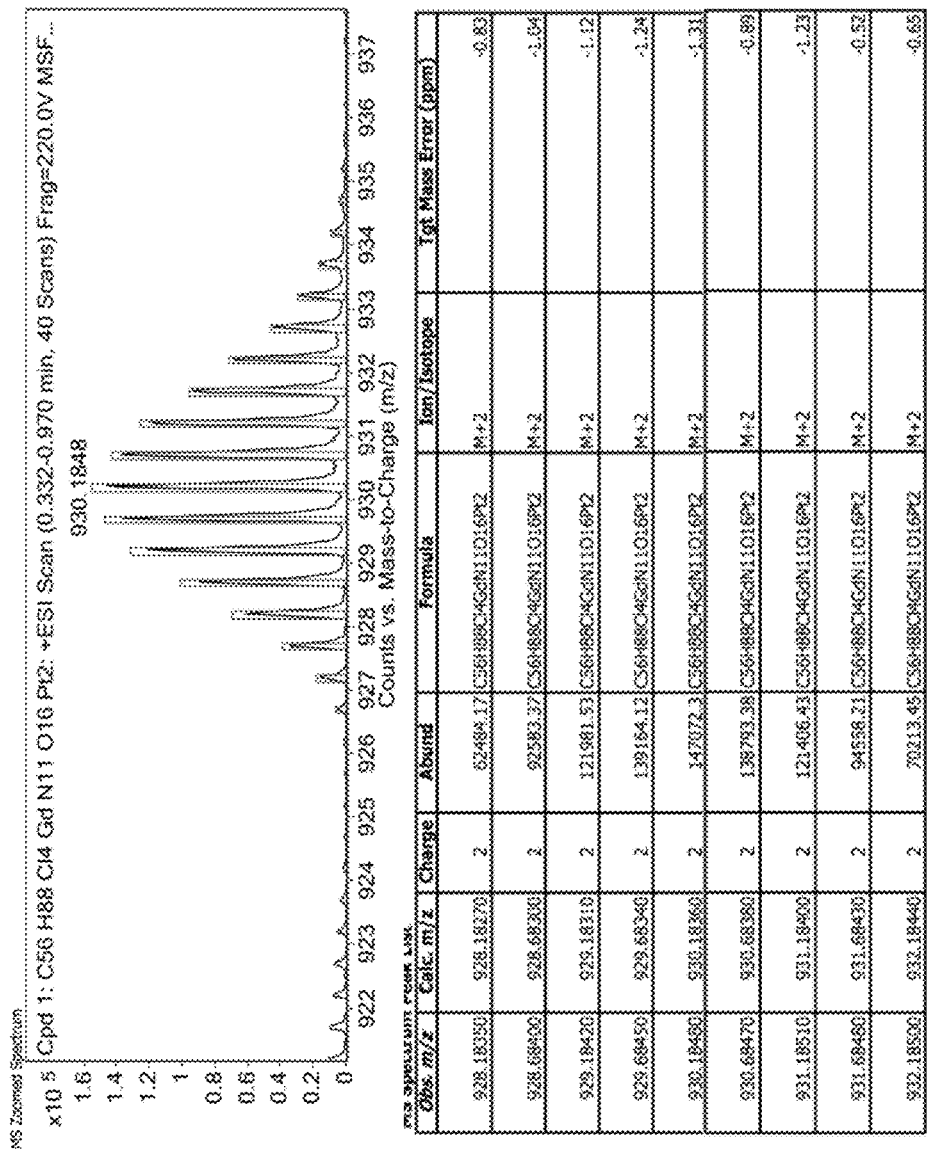
FIG. 14 shows the high resolution ESI-MS showing an enhancement of the most intense peaks corresponding to 5. Red boxes represent theoretical isotopic relative abundances.
Figure 15:
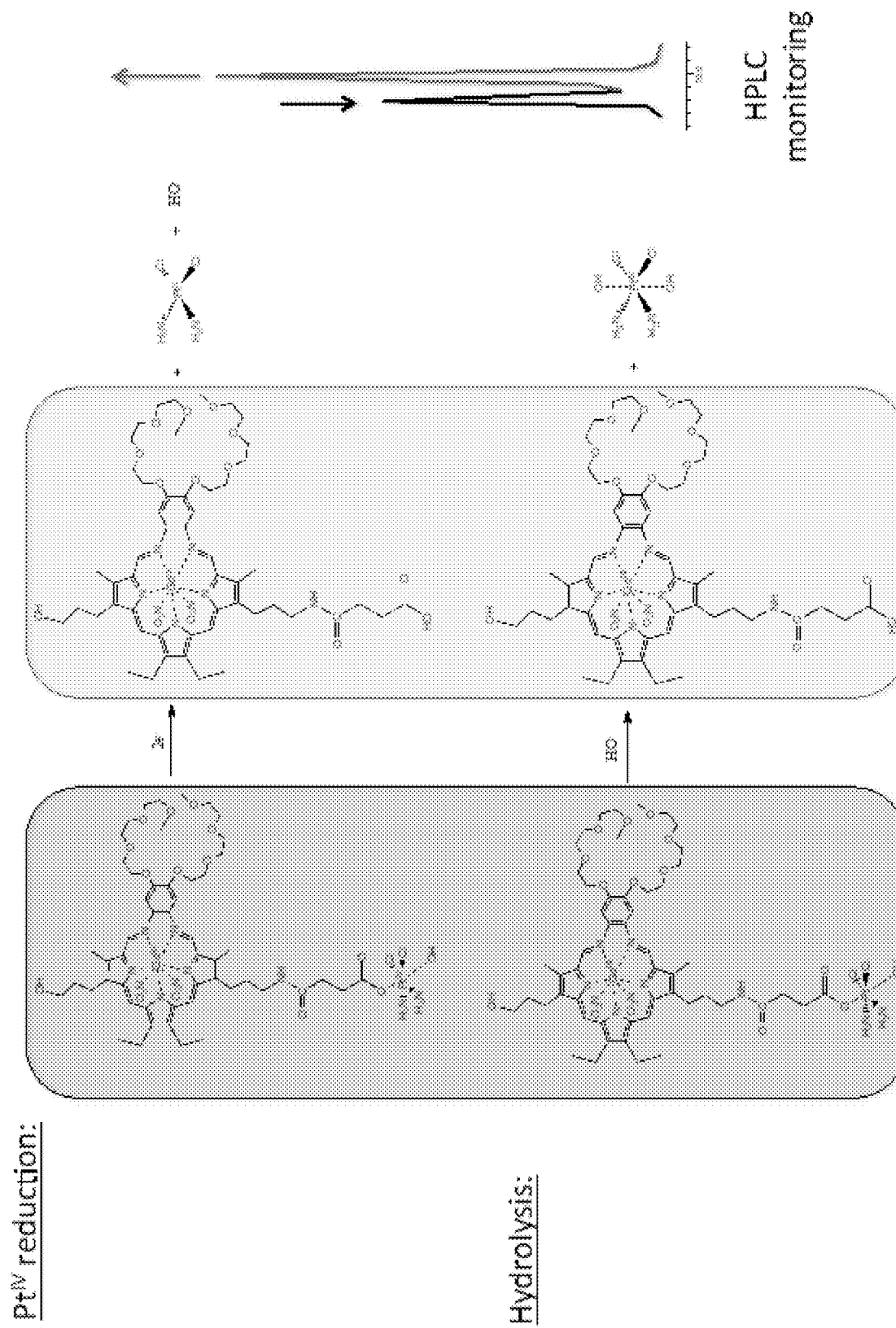
FIG. 15 shows the formation of 6 (red frame) upon reduction (peak size increasing) or hydrolysis (peak size decreasing) of 4 (black frame) monitored by RP-HPLC.
Figure 16:
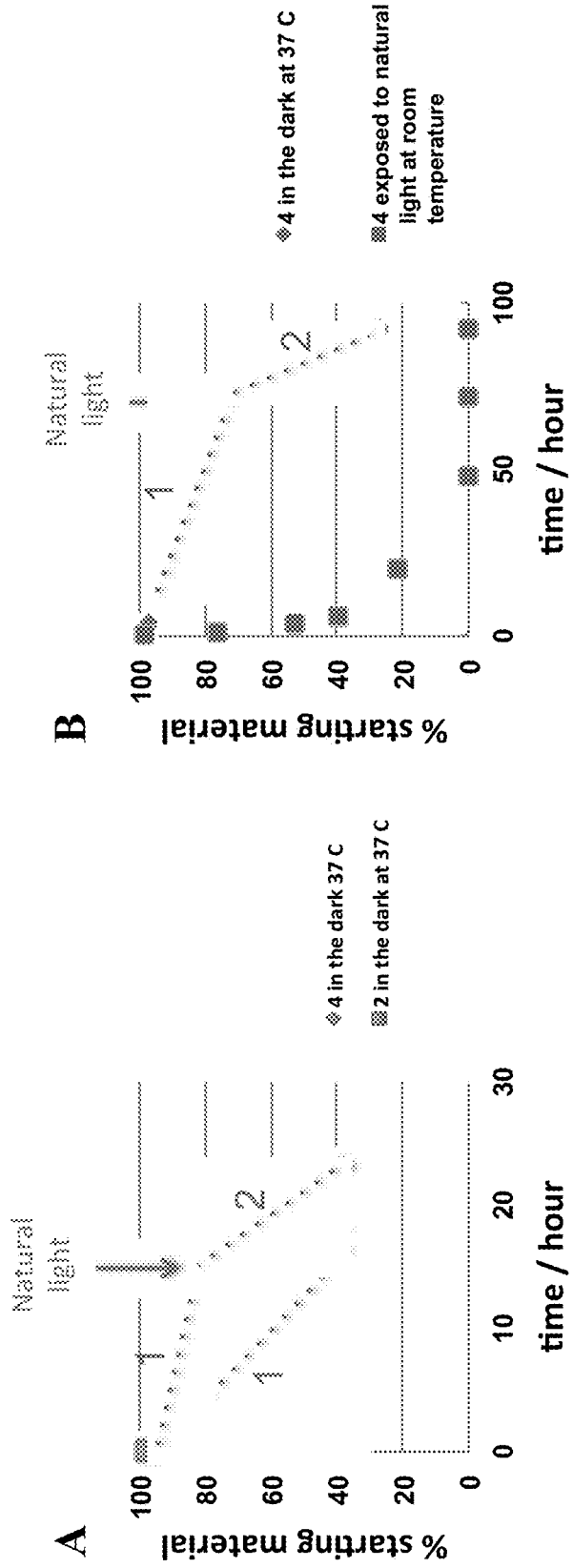
FIGS. 16A & B. (A) Comparison of the rate of hydrolysis for the known platinum(II)-texaphyrin conjugate 2 (cisTEX, red squares) compared to that of 4 at 37 C (blue rhombi) in phosphate buffer saline solution (pH=7.5, 6 mM phosphate, 100 mM NaCl); (B) Reduction rate of 4 in the dark at 37 C (blue rhombi) compared to (4) exposed to laboratory light at room temperature (red squares) in phosphate buffer saline (pH=7.5, 6 mM phosphate, 100 mM NaCl). The designation 1 indicates the hydrolysis phase (absence of light) while the designator 2 indicates the phase corresponding to subsequent light exposure.

$5_{NO3}$=MGd$(3)_2$: EDC.HCl (14.5 mg, 76 ,umol) and N-hydroxysuccinimide NHS (8.74 mg, 0.21 mmol) were dissolved in submicron filtered HPLC grade water (8 mL). Complex 3 (33 mg, 76 µmol) as a suspension in water (2 mL) was added to the "EDC.HCl+NHS" solution and left stirring for 30 minutes. Precursor $1^{NH2}{}_{NH2}$ (34.5 mg, 30 µmol, RT=6.9 min) in $CH_3CN$ (5 mL) was added drop-wise to the previous solution and the reaction mixture was kept in the dark for 20 hours. The progress of the reaction was checked by HPLC. Two new peaks appear at RT=7.7 and 8.7 min as the reaction is allowed to run. The first peak (7.7 min) is the mono-platinated compound MGd(3)($NH_2$) and the second one (8.7 min) is the desired bis-platinated product (5). After 20 h, EDC.HCl and NHS (76 µmol of each) were added in water. After 3 days, there is still a trace of starting material (2%). The mono- and bisplatinated compounds are likewise present in similar quantities (as inferred from HPLC analysis). The solution was diluted with 0.1 M aqueous $KNO_3$ and loaded onto a C18 column. The two conjugates were purified and isolated using an increasing gradient of acetonitrile in 0.1 M aqueous $KNO_3$. Fractions were monitored by HPLC, desalted using a new C18 column and submicron filtered HPLC grade water, eluted with methanol and dried under reduced pressure. This gave 5 as dark green powder. The yield was 12 mg (20%). Characterization is shown in FIGS. 13A & B and 14.

Example 4

Stability and Biological Studies of Texaphyrin Platininn Complexes

1. Hydrolysis and Light-Induced Reduction of 4

For the hydrolysis studies, reactions were carried in the dark by following the changes in the spectral features as a function of time in aqueous media. For the light-induced release studies, solutions of 3 or 4 contained in glass vials were exposed to sunlight in the laboratory behind a double-paned window (Viracon®, VE1-85), filtering off about 75% of the UV light. The same experiments were also carried out using a fluorescent tube Hg 25W (light source in chemical fume hood).

In order to identify the reduced platinum complex, the solution was loaded onto a C18 column to separate the platinum complex from the texaphyrin moiety. The green fraction was found to contain the succinic-functionalized texaphyrin 6, as identified by RP-HPLC and HR ESI-MS analysis (FIGS. 9A & B and 10). The first fraction collected, containing the platinum complex, revealed a peak eluting at 3 min analogous to those observed for cisplatin and for 3 after being reduced (see FIG. 17A-E).

2. Photo-Reactivity of 3:

The photo-reactivity of compound 3 is shown in FIGS. 18-22.

Figure 23:
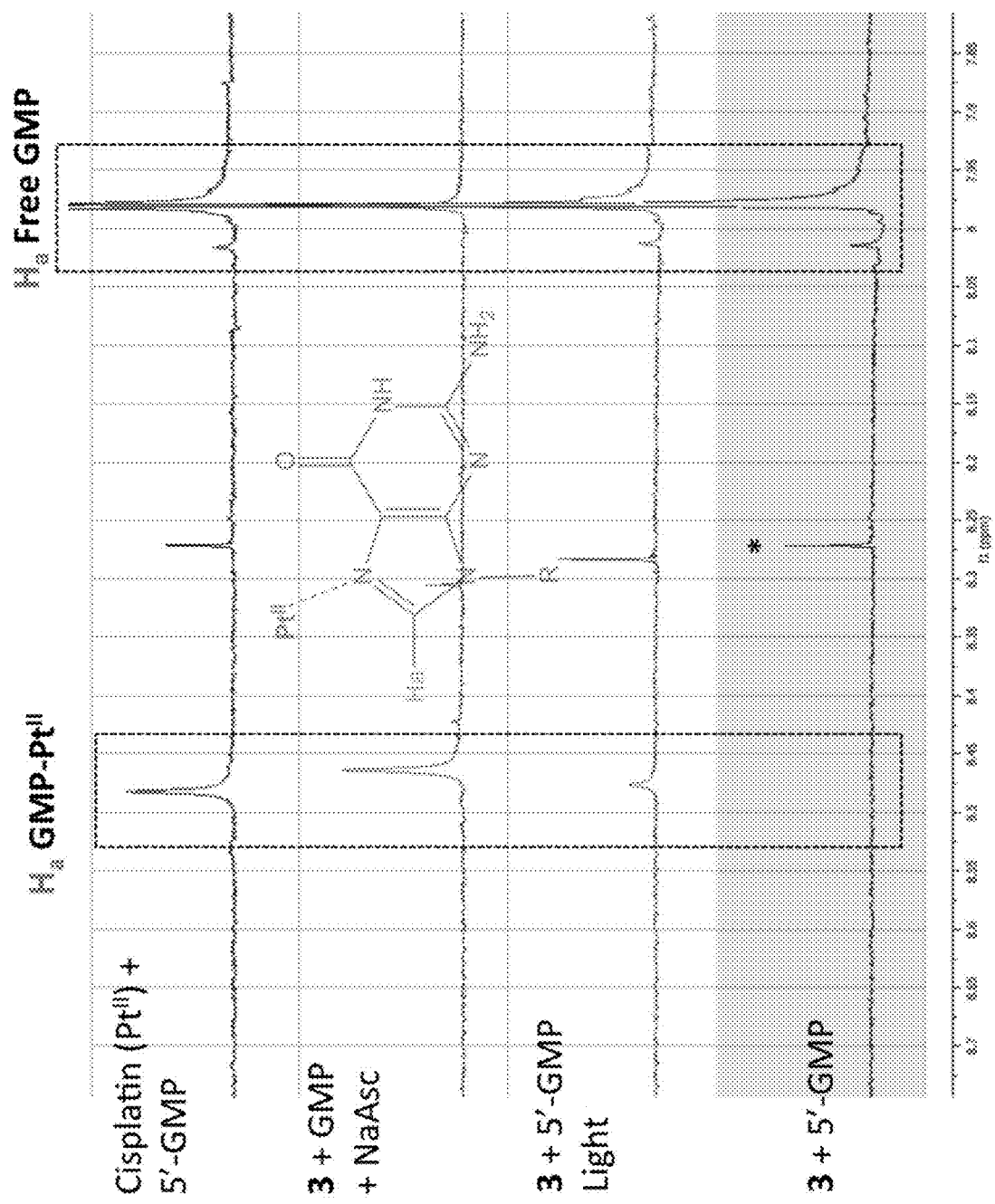
FIG. 23 shows the $^1$H-NMR spectra recorded in D$_2$O (pH=7), 300 K, 400 MHz as obtained after exposure of the product obtained by reduction of 3 (either using laboratory light (filtered sunlight) for two days or sodium ascorbate (5 equiv.)) to 5' GMP for 2 additional days. As a reference, cisplatin was exposed to 2 equivalents of 5' GMP for 2 days; this forms the adduct (5' GMP)2Pt(II)(NH$_3$)$_2$. * 32 impurity.

3. Interaction between 5'-GMP and the photo-induced reduction product of 3:

The NMR spectra shown in FIG. 23 shows the sequestration of 3 and 5'-GMP.

Figure 24:
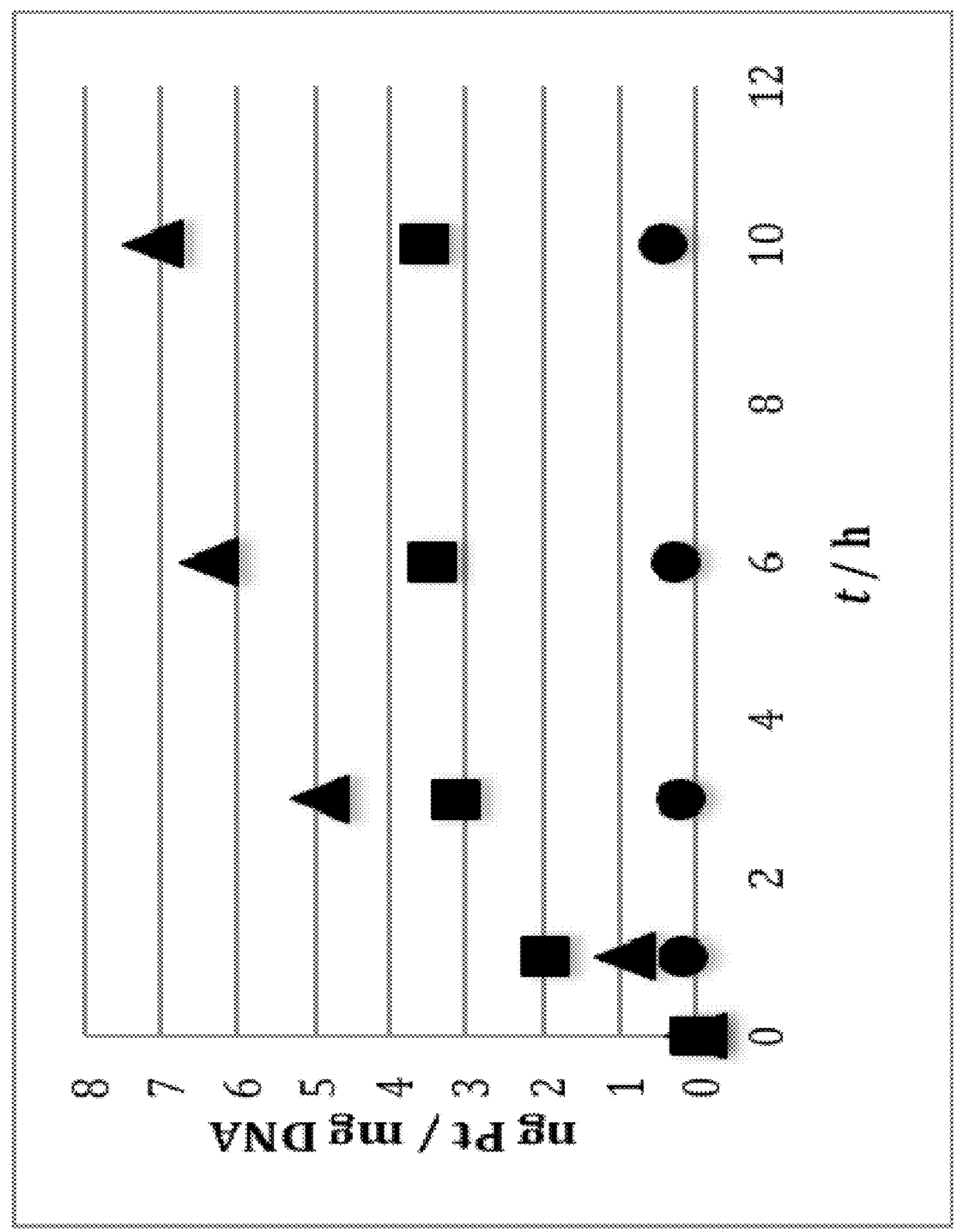
FIG. 24 shows the quantification by FAAS (Pt) and by nanodrop (DNA) of the number of Pt-DNA adducts formed after reaction of 4 with DNA in the dark (black circles) or exposed to laboratory light (black squares). Cisplatin (triangle) was used as a reference.
Figure 25:
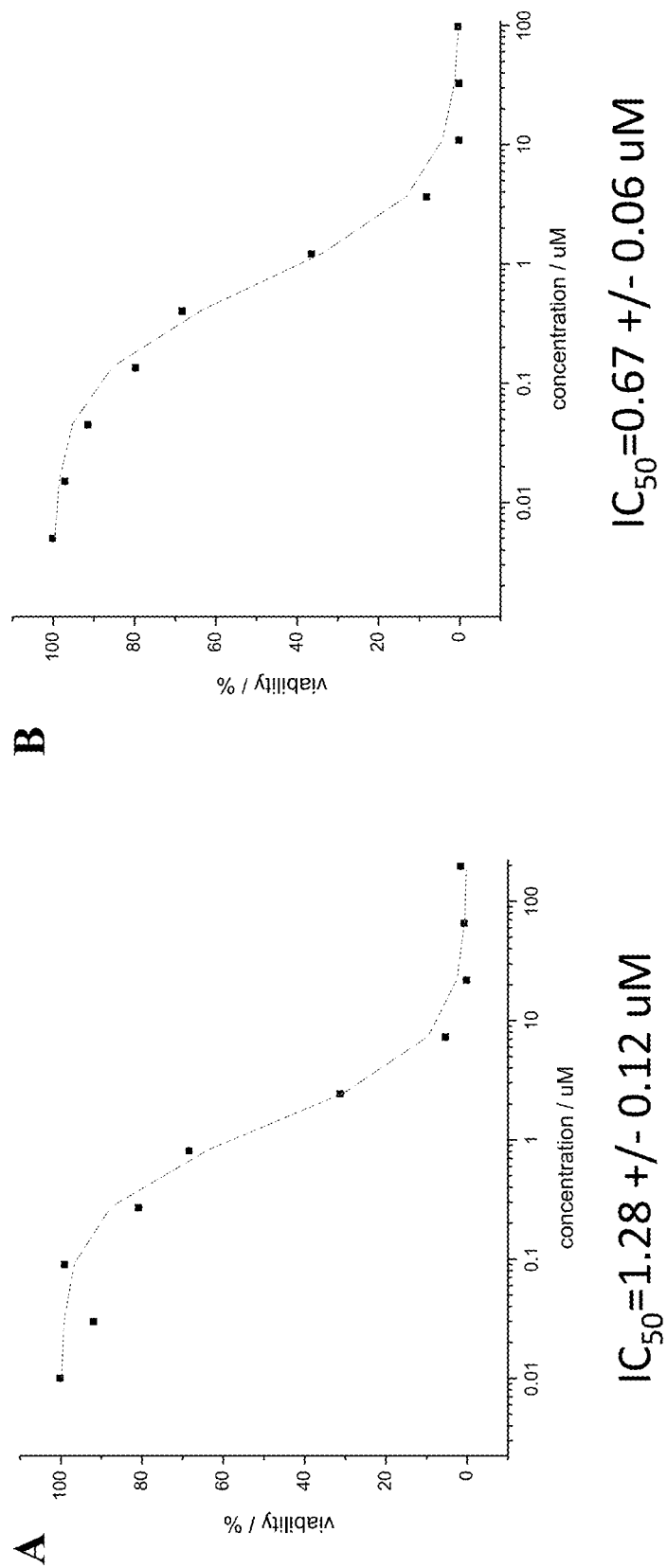
FIGS. 25A & B show the determination of the half maximal inhibitory concentrations (IC$_{50}$ in μM, logarithmic scale) for the conjugates 4 (FIG. 25A) and 5 (FIG. 25B) against cancer cells from the wild type cell line, A2780.
Figure 26:
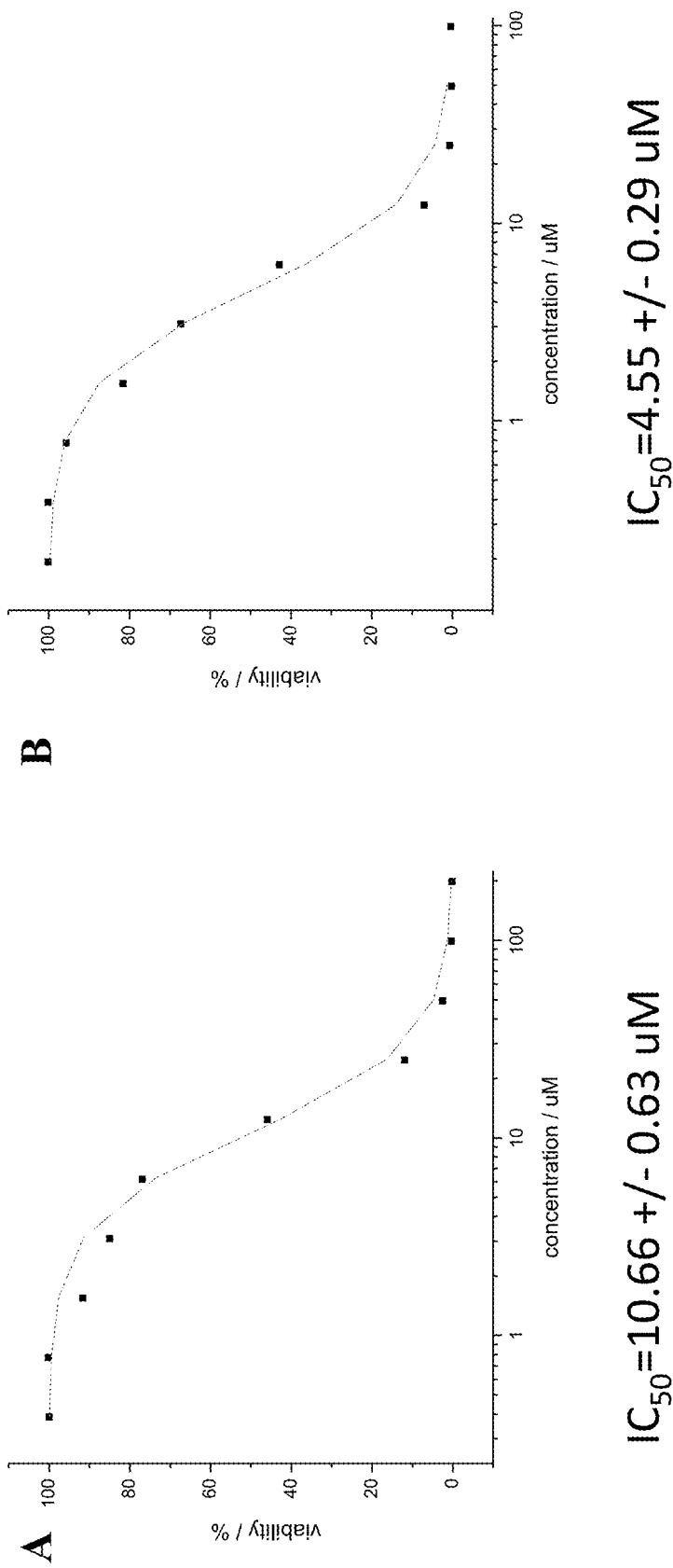
FIGS. 26A & B show the determination of the half maximal inhibitory concentration (IC$_{50}$ in μM, logarithmic scale) for the conjugates 4 (FIG. 26A) and 5 (FIG. 26B) against cancer cells from the cisplatin-resistant cell line, 2780CP.

4. Platinum-DNA interactions:

Salmon sperm DNA (1.125 mL of 500 µg DNA/mL in Tris-EDTA buffer) was incubated at 37° C. in the dark or exposed to light with platinum complexes (in solution in water; approximately 1 platinum/75 nucleotides as the final ratio) in the absence or presence of glutathione (GSH; solution in 20 mM EDTA). 200 µL aliquots were removed and added immediately to 40 µl of a 10 M aqueous ammonium acetate solution. DNA in samples was precipitated by adding 0.8 mL of absolute ethanol prechilled at −20° C. The samples were left in an ice bath for 1 h and centrifuged at 14000 rpm for 4 minutes. The supernatant was removed carefully and small pellets obtained in this way were dissolved in 50 µL of TRIS-EDTA buffer overnight at room temperature. Platinum content was determined by FAAS (model AA300/GTA-96; Varian Instruments, Victoria, Australia) using conditions described previously (Siddik, et al., 1987; Siddik and Newman, 1988) Samples were diluted with HCl when the initial Pt concentration was too high. DNA concentrations were determined using a Nanodrop ND-1000 spectrophotometer. Results can be seen in FIG. 24.

Figure 19:
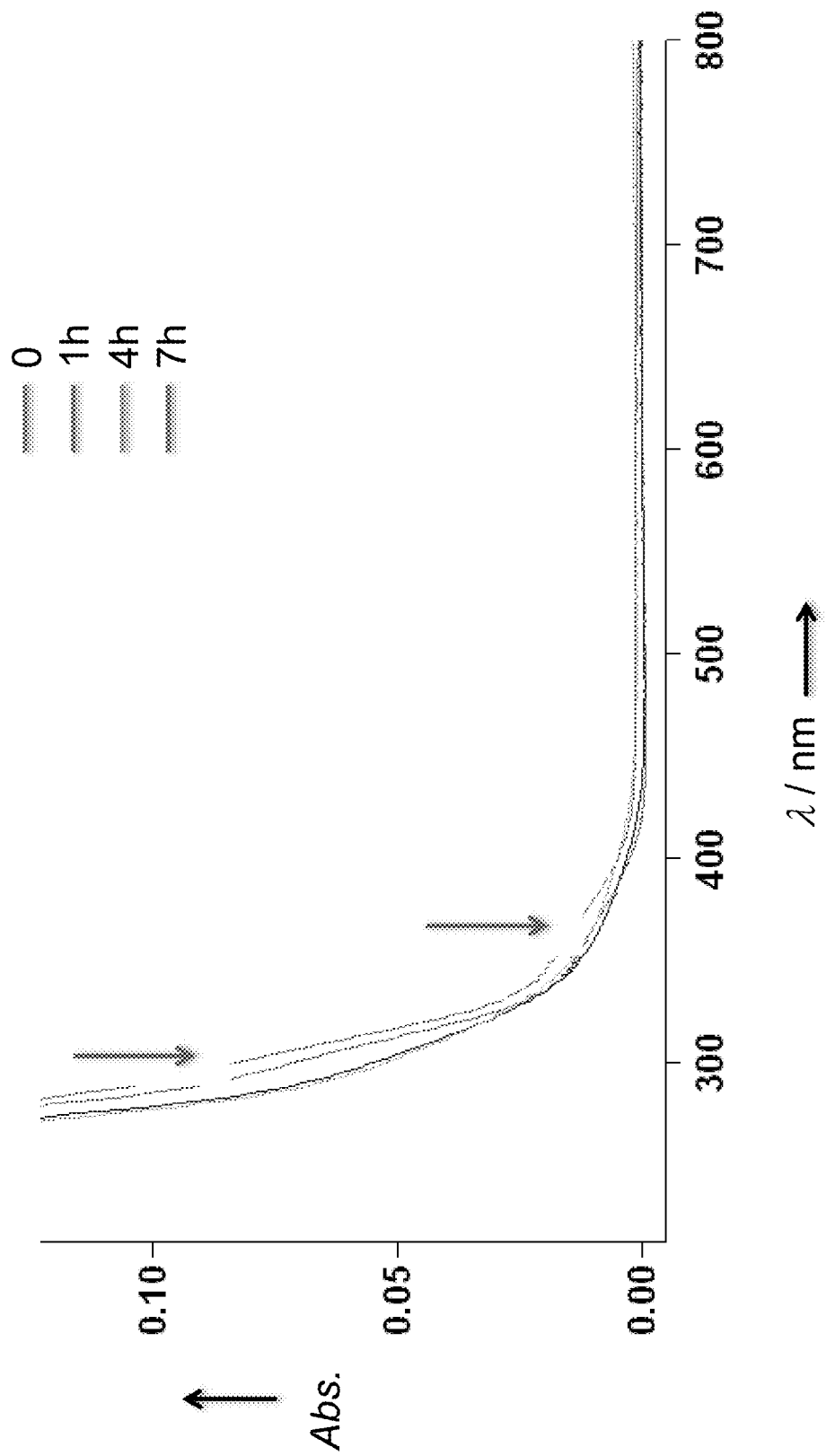
FIG. 19 shows the UV-visible spectra of 3 (in PBS solution, pH=7.5, concentration =1.6×10$^{-4}$ M) before (red line) and after laboratory light exposure. The evolution observed (decrease in absorbance between 290 and 390 nm when Pt(IV) is reduced) is consistent with Ramos, et al., 2011.

5. In Vitro Tests:

The proliferation of exponential phase cultures of A2780 and 2780CP cells was assessed by tetrazolium dye reduction (Mosmann, 1983, which is incorporated herein by reference). In brief, tumor cells were seeded in 96-well microliter plates at 500 (A2780) and 1000 (2780CP) cells/well, respectively, and allowed to adhere overnight in RPMI 1640 medium supplemented with 2 mM L-glutamine, 10% heat inactivated fetal bovine serum, and antibiotics (200 U/cm$^3$ penicillin and 200 µg/cm$^3$ streptomycin). After 4 days, the tetrazolium dye, 3-(4,5-dimethylthiazol-2-yl)-2,5-diphenyltetrazolium bromide (MTT, Sigma Chemical) was added to each well, the plates incubated at 37° C. for 4 hours, whereupon the medium was removed, the formazan product dissolved in DMSO (50-100 µL) and absorbance values at 560-650 nm were measured using a microplate reader (Molecular Devices, Sunnyvale, Calif.). Absorbance values were corrected for background and then normalized to wells containing untreated cells to allow plate-to-plate comparisons. The growth inhibition data were fitted to a sigmoidal dose-response curve to generate $IC_{50}$, which is the drug concentration inhibiting cell growth by 50%. The $IC_{50}$ is presented as mean ±standard deviation. The $IC_{50}$ values are shown in FIGS. 19-20.

Example 5

Formation of OxaliPt(IV)-Tex and Hetero-bis Platinum(IV) Conjugates

1. Synthesis of Platinum (IV) Complex, Derivate from Oxaliplatin

Figure 32:
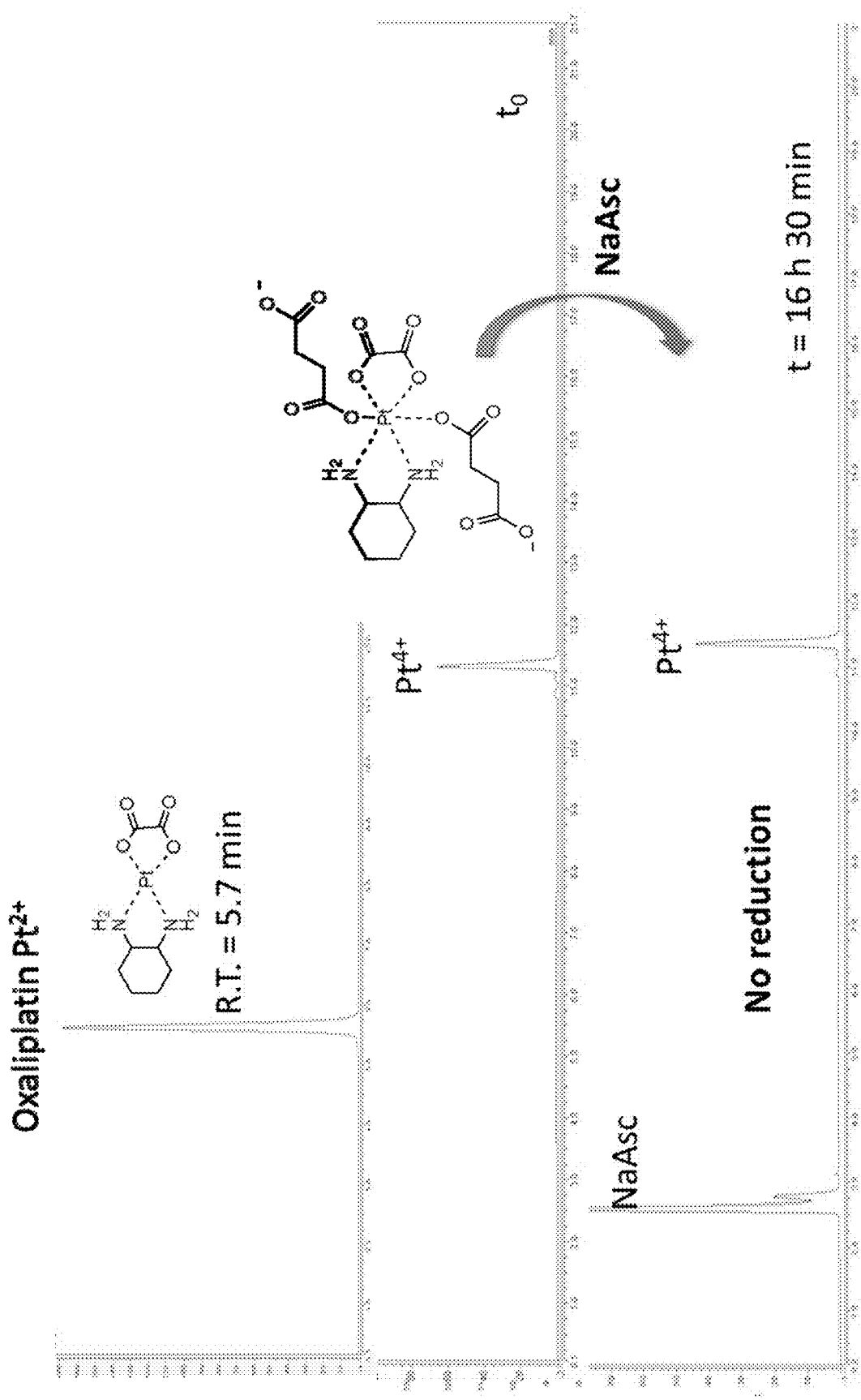
FIG. 32 shows the HPLC trace of oxaliplatin (top), a platinum(IV) analogue of oxaliplatin (middle), and the platinum(IV) analogue of oxaliplatin in the presence of sodium ascorbate (bottom).

The platinum(IV) complex used for the synthesis of oxaliPt(IV)-TEX (FIG. 27) (with $L_{ax}$=acetate, $L_{equa1}$=oxalate and $L_{equa2}$=R, R-diaminocyclohexane) was synthesized following the published protocols (Hambley et al., 2013; Keppler et al., 2014). The only difference is that the final compound was purified by silica gel chromatography using an increasing gradient of methanol in dichloromethane (from 5 to 60%). The purified complex was characterized by TLC (Rf=0.17 in methanol:dichloromethane 3:7), by $^1$H NMR (FIG. 33) and by HR-ESI MS (FIG. 32).

2. Synthesis of OxaliPt(IV)-Tex Conjugate

Figure 27:
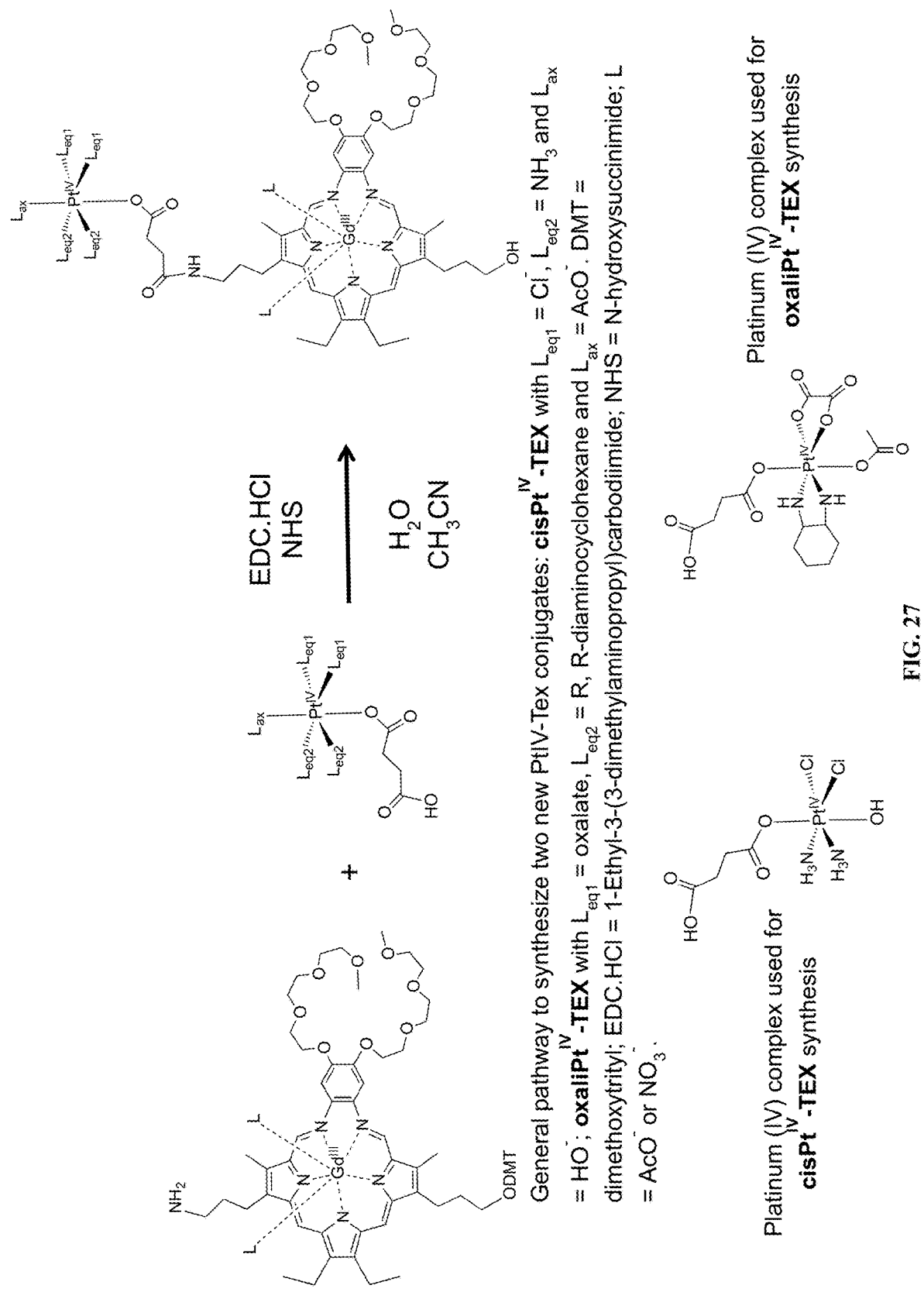
FIG. 27 shows the general synthetic scheme to obtain either OxaliPt(IV)-TEX or cisPt(IV)-TEX.
Figure 28:
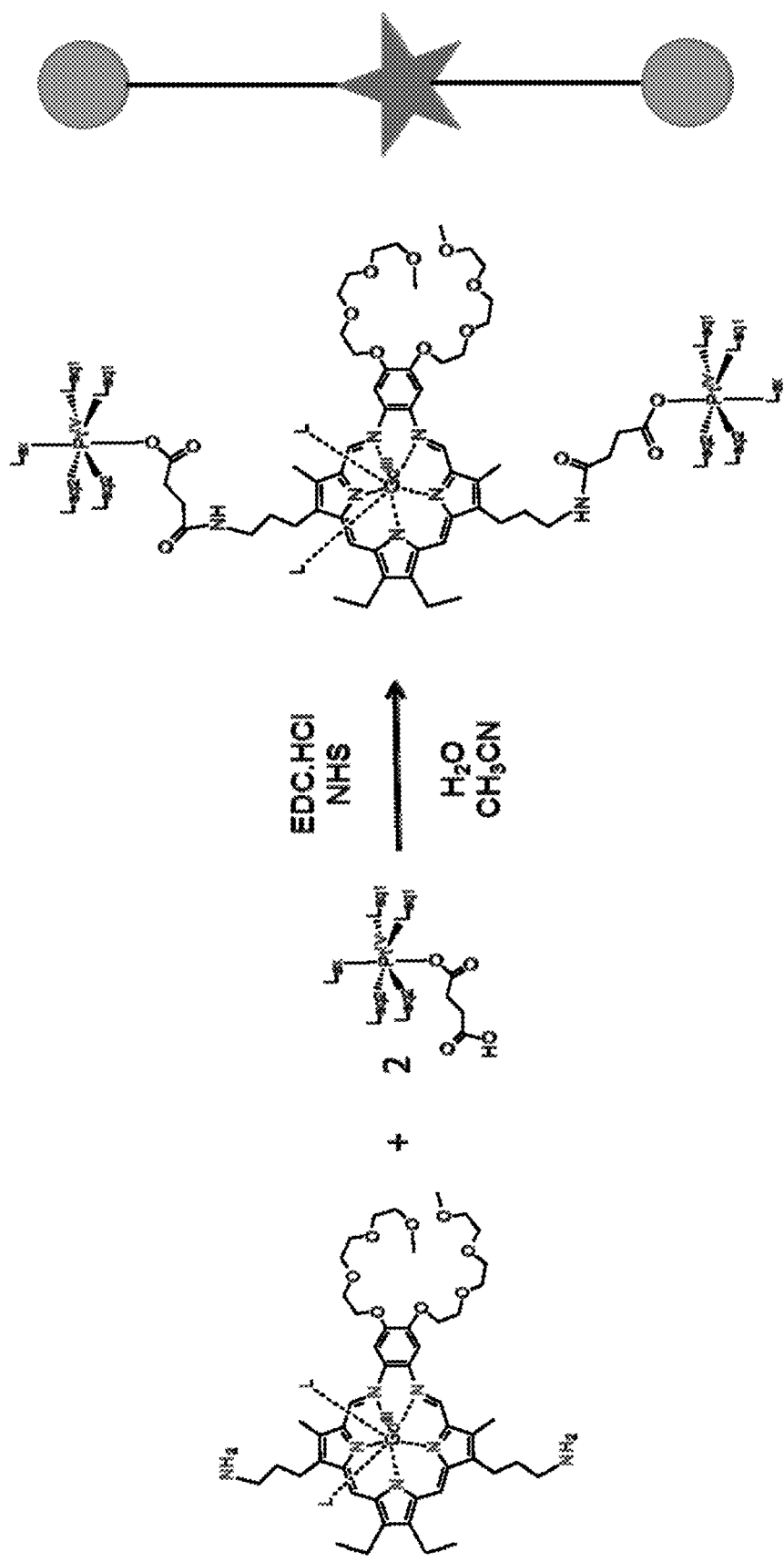
FIG. 28 shows the general synthetic scheme to obtain dimeric structures of either OxaliPt(IV)-TEX or cisPt(IV)-TEX.
Figure 29:
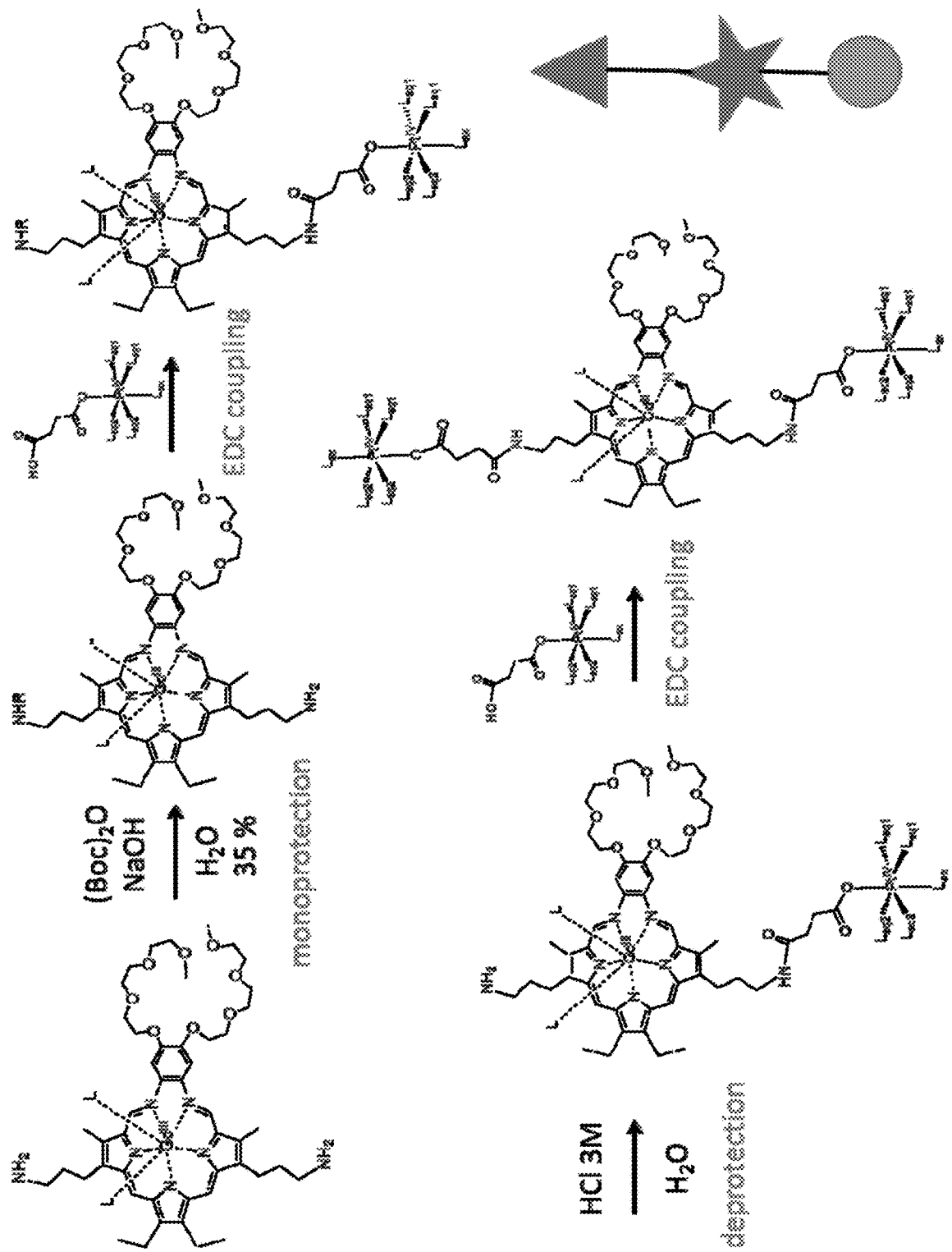
FIG. 29 shows the general synthetic scheme to obtain a heterodimeric structure containing both the platinum conjugating units OxaliPt(IV) and cisPt(IV) linked to the texaphyrin.

Analogues of compounds 4 that contain the oxaliplatin platinum core were prepared using the method described in FIGS. 27-29.

Figure 30:
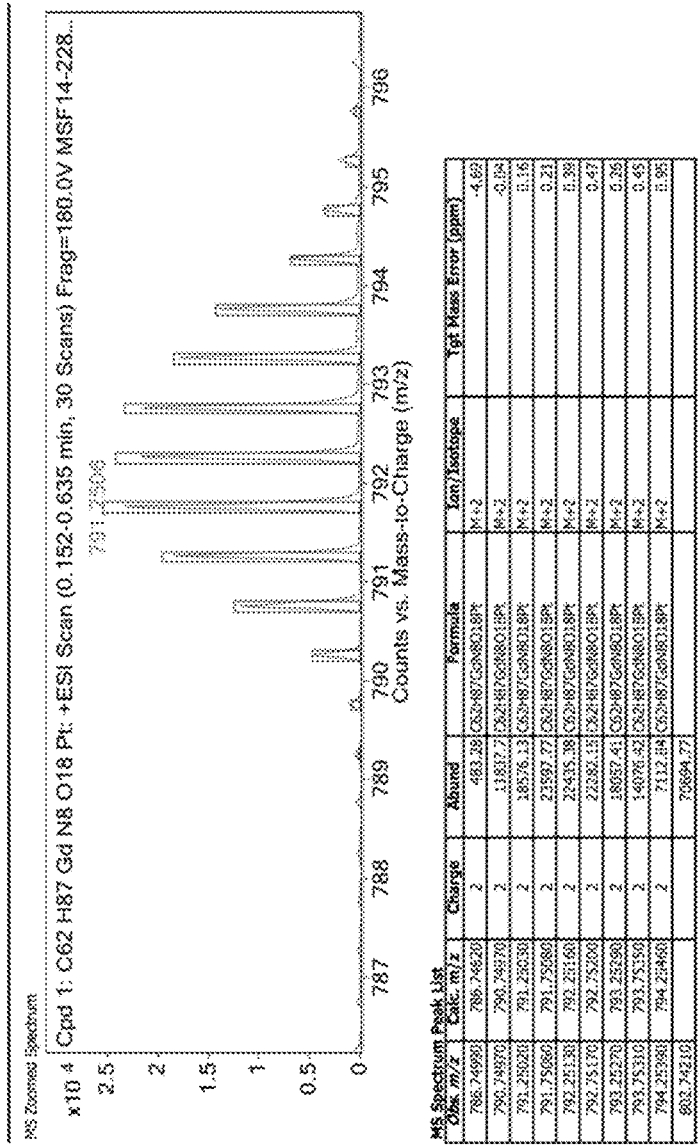
FIG. 30 shows the high-resolution ESI-MS spectrum of OxaliPt(IV)-TEX recorded from an aqueous sample.
Figure 31:
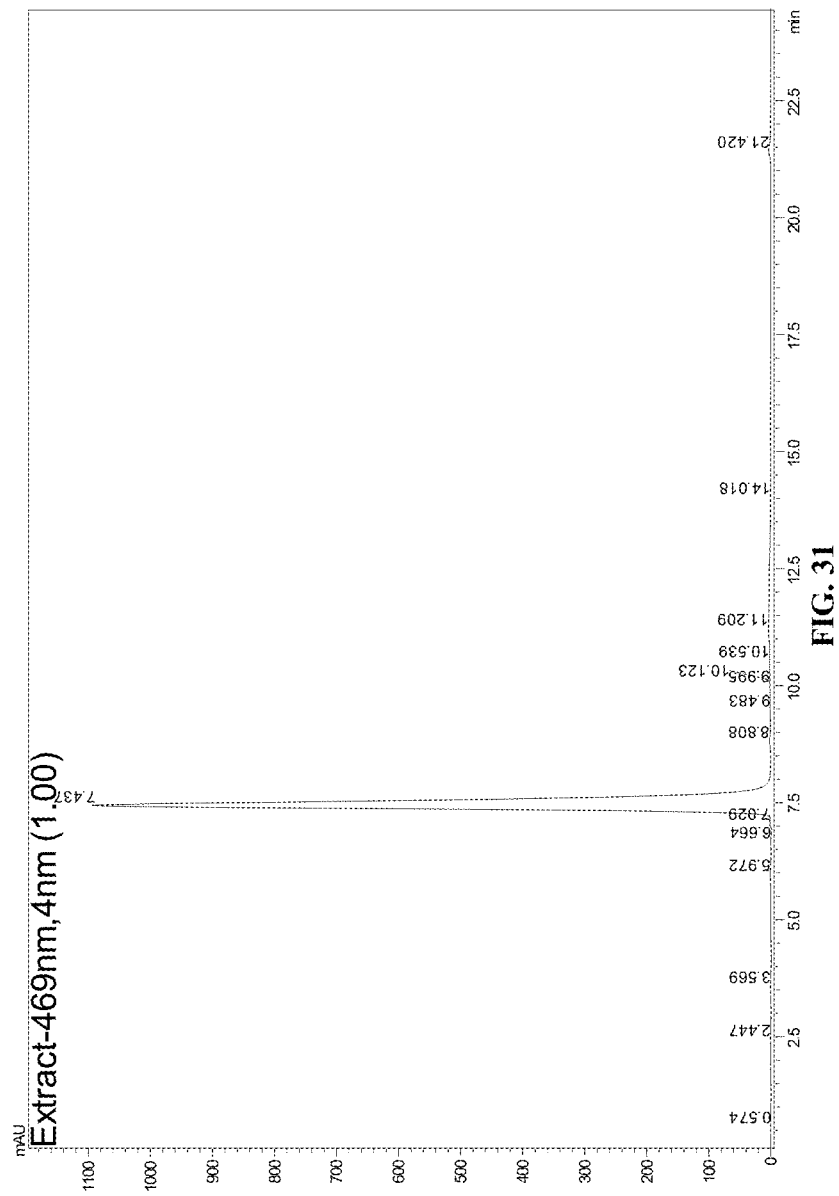
FIG. 31 show the RP-HPLC chromatogram monitoring at 469 nm and UV-vis spectrum of conjugate OxaliPt(IV)-TEX studied in water.

EDC.HCl (17 mg, 89 μmol) and N-hydroxysuccinimide NHS (12 mg, 107 μmol) were dissolved in HPLC submicron filtered grade water (5 mL). A Pt(IV) complex derived from oxaliplatin (FIG. 27) (23 mg, 40 μmol) in water (5 mL) was added to the mixture (termed "EDC.HCl+NHS") and left stirring for 30 minutes. A solution of precursor $1^{ODMT}_{NH2}$ (50 mg, 33 μmol, HLPC RT =11.4 min) in $CH_3CN$ (5 mL) containing diisopropylamine (9 μL, 64.2 μmol) was added drop-wise to the previous solution and the reaction mixture was kept in the dark for 20 h. The progress of the reaction was monitored by HPLC (a new peak is formed that is characterized by a RT=13 min). Following this period, aqueous HCl 0.5 N (2 mL, 1 mmol) was added to remove the DMT protecting group. After one hour (reaction monitored by HPLC), 50 mL of an aqueous solution containing 0.1% of acetic acid was added to the reaction mixture and the solution was loaded on a C18 column. The elution was done using an increasing gradient of acetonitrile in water (containing 0.1% acetic acid). The isolated fraction corresponding to the desired compound (FIG. 31) was loaded onto a new C18 column, desalted with water and eluted with pure methanol. The solvent was removed under vacuum to give the product as a dark green powder (36 mg, 64%). The product with axial acetate ligands was analyzed by high resolution ESI-MS; as shown in FIG. 30. Elemental Analysis: Calculated: C=46.55%, H=5.50%, and N=6.58%; Found: C=45.55%, H=5.79%, and N=6.59%. Similar compounds with axial hydroxide and chloride ligands were prepared similarly.

Example 6

General Methods and Materials for Texaphyrin and High Oxidation State Metal Chemotherapeutic Complexes 1. HPLC Monitoring of Pt(IV) Reduction Catalyzed by Motexafin Gadolinium (MGd)

Pt(IV) complex and sodium ascorbate were dissolved in PBS buffer (pH=7) and incubated at 37° C., in absence or presence of MGd. At a given time, an aliquot (20 μL) was analyzed by RP-HPLC (C18 column, increasing gradient of acetonitrile in water, both solvents contain 0.1% acetic acid).

2. Antiproliferative Activities Determined Using 3-(4,5-diniethylihiazol-2-yl)-2,5-diphenyltetrazolium bromide (MTT) Assays A2780 cancer cells were incubated (37° C., 5% $CO_2$ atmosphere, dark) in 96-wells plates at a concentration of 600 cells/well, in a culture medium containing 10% fetal bovine serum and supplemented with penicillin and streptomycin. After 15 h, drugs (Pt(IV), MGd, MGd+Pt(IV)) were added to cells (gradient of concentration, from 0 to 200 μM, 3-fold dilutions) and plates were incubated for five more days using the above conditions. After five days, MTT dye was added in each well (0.15 mg/well) and plates were left for 4 hours in the incubator. Then, supernatant was carefully removed and 50 μL of DMSO were added to dissolve MTT purple formazan crystals. The absorbance was read at 570 nm using a plate reader.

Example 7

HPLC Monitoring of the Pt(IV)Reduction Catalyzed by Motexafin Gadolinium (MGd)

Figure 33:
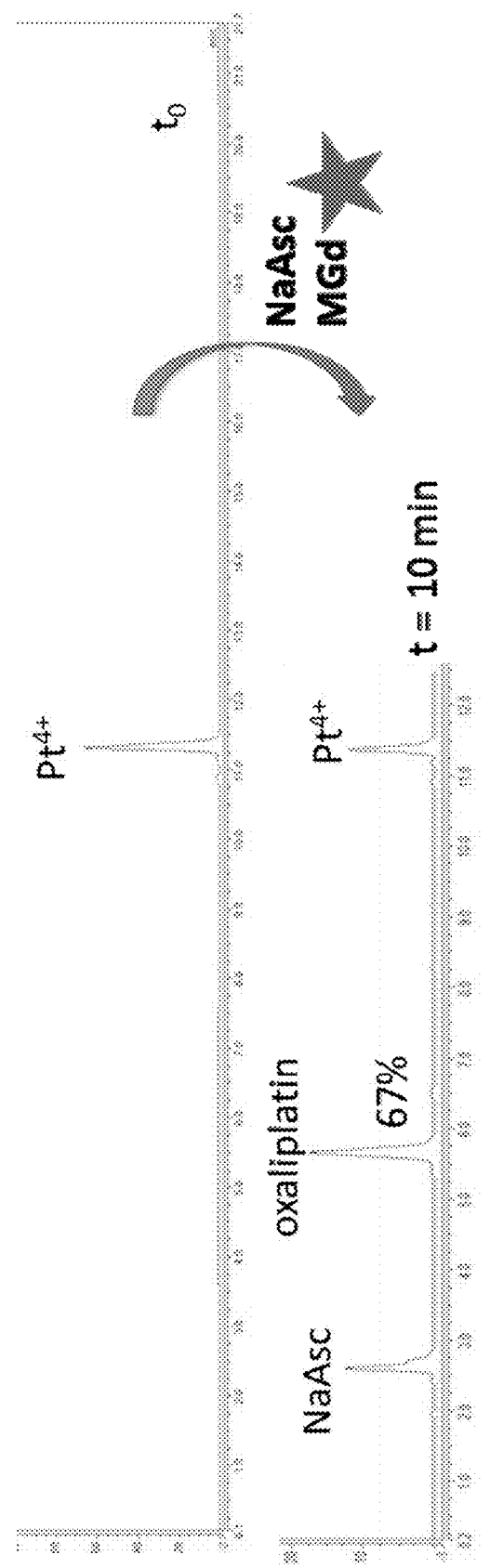
FIG. 33 shows the HPLC trace of a platinum(IV) analogue of oxaliplatin (top), and the platinum(IV) analogue of oxaliplatin in the presence of sodium ascorbate and the texaphyrin compound (bottom).

In absence of motexafin gadolinium (MGd), no change was noticed on the HPLC trace. On this basis, it was concluded that the starting material Pt(IV) does not react with sodium ascorbate (1 molar equiv./2 equiv. electrons), even after several hours (FIG. 32). In presence of MGd (0.5 equiv.), a new peak was observed after only 10 minutes. The peak area represents about 67% and the retention time matches perfectly with the one of oxaliplatin (Pt(II)) (FIG. 33). This provides evidence that MGd is essential for Pt(IV) reduction acting as a redox mediator to allow the electron transfer from sodium ascorbate to Pt(IV). This reduction goes to completion in about 25 min under these conditions. This experiment was repeated with a variety of different Pt(IV) complexes.

Example 8

Figure 34:
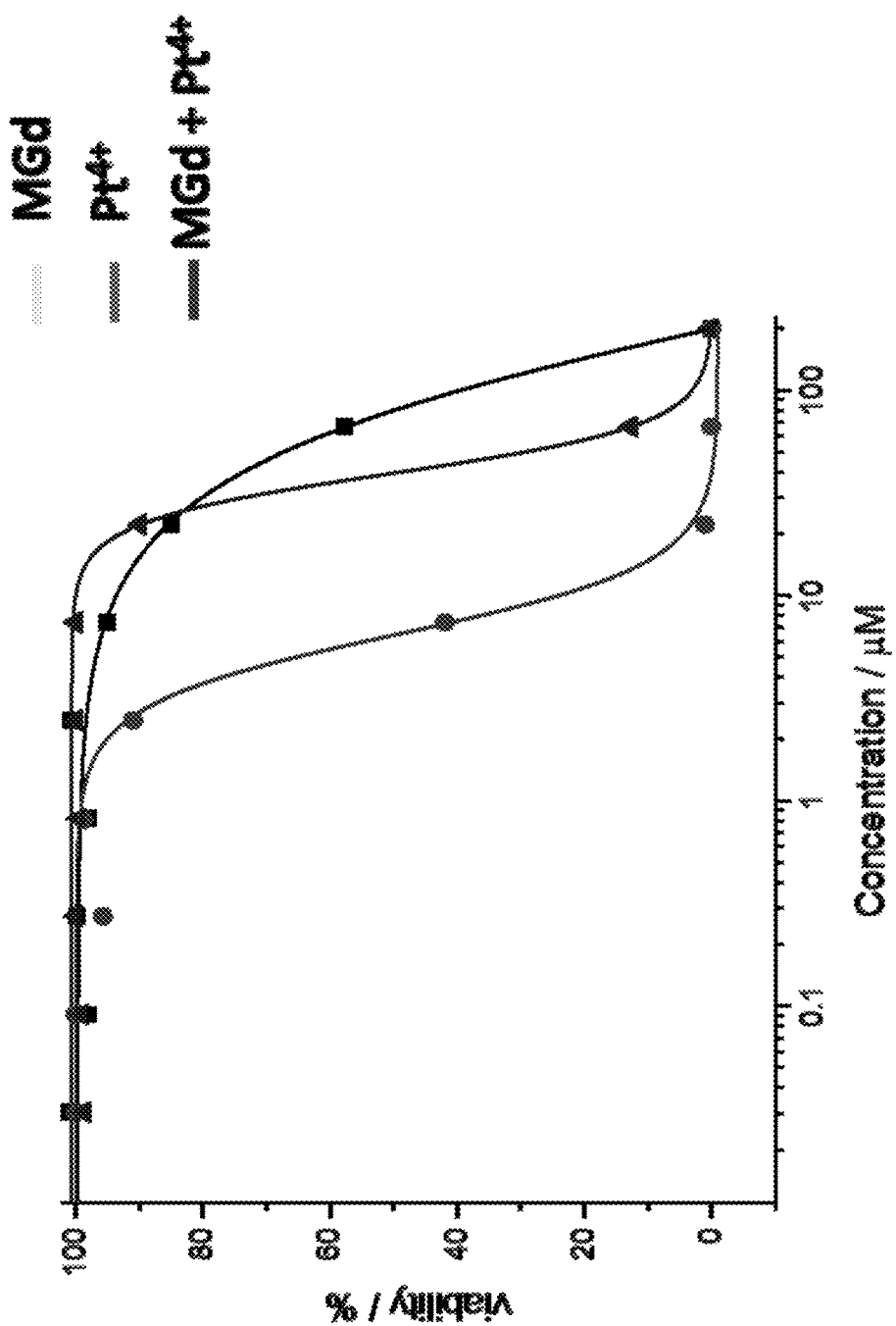
FIG. 34 shows cell viability as a function of concentration with the texaphyrin compound (MGd) (squares), the platinum(IV) analogue of oxaliplatin (triangle), and the platinum(IV) analogue of oxaliplatin with a texaphyrin compound (circles).
Figure 35E:
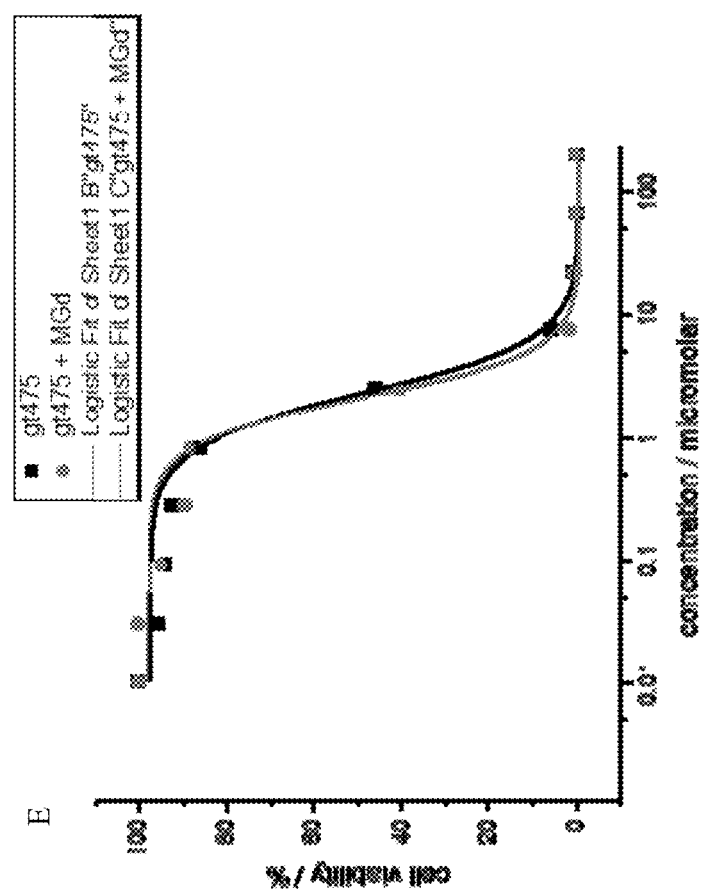

Antiproliferative Activities Determined Using 3-(4,5-diitiethylitiazol-2-yl)-2,5-diphenyitetrazolitim bromide (MTT) Assays The growth inhibitions observed for both MGd ($IC_{50}$=78 μM) and Pt(IV) ($IC_{50}$=40 μM) are much lower than the one observed when MGd is combined with Pt(IV) ($IC_{50}$=6.5 μM) (see FIG. 34). This observation is taken as evidence that a synergistic effect takes place and is in agreement with the results observed in the HPLC experiments (described in Example 7).

Similar growth inhibition studies were carried out using a variety of different Pt(IV) complexes in combination with MGd (See FIG. 35A-E). A summary of the $IC_{50}$ observed is shown in Table 1.

TABLE 1

| $IC_{50}$ of Different Pt(IV) Complexes in the Presence of MGd ||| |
| --- | --- | --- |
| Pt(IV) Complex | $IC_{50}$ without MGd (μM) | $IC_{50}$ with MGd (μM) |
| 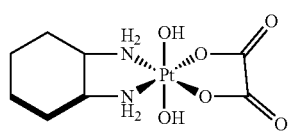 | 22.3 ± 2.8 | 9.26 ± 1.61 |

TABLE 1-continued

IC$_{50}$ of Different Pt(IV) Complexes in the Presence of MGd

| Pt(IV) Complex | IC$_{50}$ without MGd (µM) | IC$_{50}$ with MGd (µM) |
| --- | --- | --- |
| [structure] | 6.15 ± 0.69 | 4.12 ± 0.14 |
| [structure] | 5.81 ± 0.92 | 3.28 ± 0.53 |
| [structure] | 4.10 ± 0.13 | 3.42 ± 0.04 |
| [structure] | 2.30 ± 0.12 | 2.12 ± 0.13 |
| [structure] | 34 ± 5.6 | 7 ± 0.6 |

All of the compositions and methods disclosed and claimed herein can be made and executed without undue experimentation in light of the present disclosure. While the compositions and methods of this invention have been described in terms of certain embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,265,823
U.S. Pat. No. 4,845,124
U.S. Pat. No. 4,870,208
U.S. Pat. No. 4,935,498
U.S. Pat. No. 4,980,473
U.S. Pat. No. 5,072,011
U.S. Pat. No. 5,252,270
U.S. Pat. No. 5,272,142
U.S. Pat. No. 5,292,414
U.S. Pat. No. 5,369,101
U.S. Pat. No. 5,409,915
U.S. Pat. No. 5,432,171
U.S. Pat. No. 5,439,570
U.S. Pat. No. 5,504,205
U.S. Pat. No. 5,533,354
U.S. Pat. No. 5,569,759
U.S. Pat. No. 5,583,220
U.S. Pat. No. 5,587,463
U.S. Pat. No. 5,591,422
U.S. Pat. No. 5,599,923
U.S. Pat. No. 5,599,928
U.S. Pat. No. 5,624,919
U.S. Pat. No. 5,776,925
U.S. Pat. No. 5,955,586
U.S. Pat. No. 5,994,535
U.S. Pat. No. 6,207,660
U.S. Pat. No. 6,340,599
U.S. Pat. No. 6,774,254
U.S. Pat. No. 7,112,671
U.S. Pat. No. 7,479,557
U.S. Pat. No. 7,655,697
U.S. Pat. No. 7,655,810
U.S. Pat. No. 8,193,175
U.S. Pat. No. 8,357,678
U.S. Pat. No. 8,410,263
U.S. Pat. No. 8,481,496
U.S. Pat. No. 8,563,712
U.S. Pat. No. 8,653,132
U.S. Pat. No. 8,729,286
U.S. Pat. No. 8,748,484
U.S. Pat. No. 8,828,984
U.S. Pat. No. 8,877,215
U.S. Patent Application 2012/0164230
U.S. Patent Application 2013/0303606
U.S. Patent Application 2014/0221475
U.S. Patent Application 2014/4165782
PCT International Application WO 2010/027428
PCT International Application WO 2012/177935
PCT International Application WO 2014/65782
PCT International Application WO 98/24424
Chinese Application CN102058576
Advanced Organic Chemistry: Reactions, Mechanisms, and Structure, March 2007.
Arambula et al., "Texaphyrins: Tumor Localizing Redox Active Expanded Porphyrins," *Anti-Cancer Agents in Medicinal Chemistry*, 11, 222-232, 2011.
Arambula et al., *Bioorg. Med. Chem. Lett.*, 21, 1701-1705, 2011.
Arambula et al., *Dalton Trans.*, 48, 1 0834, 2009.
Arambula et al., *Med. Chem. Commun.*, 3, 1275-1281, 2012.
Banfic' et al., *Eur. J. Inorg. Chem.*, 484-492, 2014.
Barnes et al., et al., J . Chem. Biol., 11:557, 2004.
Berners-Price et al., *Inorg. Chem.*, 33, 5842-5846, 1994.
Berners-Price et al., *J. Am. Chem. Soc.*, 115, 8649-8659, 1993.
Chau et al., *Exp. Cell Res.*, 241:269-272, 1998.
Chen et al., *J. Med. Chem.*, 56:8757, 2013.
Choi et al., *Inorg. Chem.*, 37, 2500-2504, 1998.
Choi etal., *Inorg. Chem.*, 38, 1800-1805, 1999.
Davies et al., *Inorg. Chem.*, 47:7673, 2008.
Dhar et al., *J. Am. Chem. Soc.*, 131, 14652-14653, 2009.
Drougge and Elding, *Inorg. Chim. Acta*, 121:175, 1986.
Elding and Gustafson, *Inorg. Chim. Acta*, 19:165, 1976;
Feazell et al., *J. Am. Chem. Soc.*, 129, 8438-8439, 2007.
Fischer et al., *NeuroToxicology*, 29, 444-452, 2008.
Godwin et al., *Proc. Natl. Acad. Sci.* USA, 89, 3070-3074, 1992.
Hall et al., *Coord. Chem. Ref.*, 232:49, 2002.
Hall et al., *J. Inorg. Biochem.*, 8:726, 2003.
Hall et al., *Metallomic*, 4:568, 2012.
Handbook of Pharmaceutical Salts: Properties, and Use (P. H. Stahl & C. G. Wermuth eds., Verlag Helvetica Chimica Acta, 2002).
Hannah, etal., *Org. Lett.*, 3(24):3911-3914, 2001.
He et al., *Proc. Natl. Acad. Sci. USA*, 97:5768-5772, 2000.
Huang et al., *Proc. Natl. Acad. Sci. USA*, 91:10394-10398, 1994.
Ines Batinic-Haberle, guest ed.; Bentham Science Publishers. DOI: 10.2 174/187 1520 11 795255894.
Johnstone etal., *Inorg. Chem.*, *DOI:* 10.1021/ic400538c, 2013.
Kelland, L. *Nat Rev Cancer*, 7:573-584, 2007.
Kuroda et al., *Inorg. Chem.*, 22, 3620-3624, 1983.
Lemma et al., *Inorg. Chem.*, 39:1728, 2000.
Montagner et al., *Angew. Chem. Int. Ed.*, 52,11785-11789, 2013.
Mosmann, T., *J. Immunol. Meth.*, 65, 55-63, 1983.
Nemirovski etal., *Chem. Commun.*, 46, 1842-1844, 2010.
Novohradsky et al., *J. Inorg. Biochem.*, 72, 2014.
Ramos et al., *Quim. Nova*, 34, 1450-1454, 2011.
Roat and Reedijk, *J. Inorg. Bloch.*, 52, 263-274, 1993.
Romero-Canelon and Sadler, *Inorg. Chem.*, 52(21): 12276-12291, 2013.
Rosenberg et al., *Nature*, 205:698, 1965.
Shi et al., *Biochem.*, 107:6, 2012.
Shi et al., *J. Inorg. Biochem.*, 107, 6-14, 2012.
Siddik and Newman, *Anal. Biochem.*, 172, 190-196, 1988.
Shimanovich, et al., *J. Am. Chem. Soc.*, 123:3613-3614, 2001.
Siddik et al., *Anal. Biochem.*, 163, 21-26; 1987.
Siddik et al., *Cancer Res.*, 58, 698-703, 1998.
Sinisi et al., *Inorg. Chem.*, 51, 9694-9704, 2012.
Van der Veer et al., *J. Inorg. Biochem.*, 26, 137-142, 1986.
Wei et al., *Org. Biomol. Chem.*, 3, 3290-3296, 2005.

Wexselblatt and Gibson, *J. Inorg. Biochem.*, 117, 220-229, 2012.
Wexselblatt et al., *Angew. Chem. Int. Ed.*, 52, 6059-6062, 2013.
Wexselblatt et al., *Chem. Eur. J.*, 21:3018, 2015.
Wexselblatt et al., *Inorg. Chim. Acta*, 393, 75-83, 2012.
Xiao et al., *Biomaterials*, 32, 7732-7739, 2011.
Xiao et al., *Chem. Commun.*, 48, 10730-10732, 2012.
Zhang et al., *Chem. Commun.*, 48:847, 2012a.
Zhang et al., *Chem. Commun.*, 48:847-849, 2012b.
Zhang et al., *Chem. Eur.* 1, 19:1672-1676, 2013.
Zheng et al., *Chem. Sci.*, 6:1189, 2015.
Zhu et al., *Chem. Int. Ed.*, 53:13225, 2014.
Zöllner et al., *Mass Spectrom.*, 36, 742-753, 2001.

What is claimed is:

1. A compound of the formula:

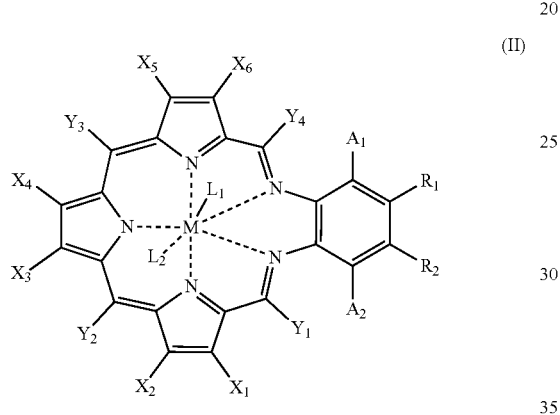

(II)

wherein:

$R_1$ and $R_2$ are each independently selected from hydrogen, halo, hydroxy, amino, mercapto, alkoxy$_{(c \leq 12)}$, substituted alkoxy$_{(c \leq 12)}$, or

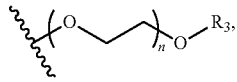

wherein n is 1-20 and $R_3$ is hydrogen, alkyl$_{(c \leq 6)}$, or substituted alkyl$_{(c < 6)}$, or a platinum(IV) chelating group;

$A_1$ and $A_2$ are each independently selected from hydrogen, halo, hydroxy, alkyl$_{(c \leq 12)}$, substituted alkyl$_{(c \leq 12)}$, alkoxy$_{(c \leq 12)}$, substituted alkoxy$_{(c < 12)}$, or

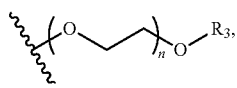

wherein n is 1-20 and $R_3$ is hydrogen, alkyl$_{(c \leq 6)}$, or substituted alkyl$_{(c \leq 6)}$, or a platinum(IV) chelating group;

$Y_1$, $Y_2$, $Y_3$, and $Y_4$ are each independently selected from hydrogen, halo, alkyl$_{(c \leq 12)}$, aryl$_{(c \leq 12)}$, substituted alkyl$_{(c \leq 12)}$, or substituted aryl$_{(c \leq 12)}$;

$X_1$, $X_2$, $X_3$, $X_4$, $X_5$, and $X_6$ are each independently selected from hydrogen, hydroxy, halo, amino, carboxy, nitro, or cyano, alkyl$_{(c \leq 12)}$, alkenyl$_{(c \leq 12)}$, alkynyl$_{(c \leq 12)}$, aryl$_{(c \leq 12)}$, aralkyl$_{(c \leq 12)}$, acyl$_{(c \leq 12)}$, amido$_{(c \leq 12)}$, or a substituted version of any of these groups, or a platinum(IV) chelating group; wherein the platinum (IV) chelating group is —$A_3$—$X_7$—$A_4$—$R_4$, wherein $A_3$ and $A_4$ are each independently alkanediyl$_{(c \leq 12)}$, alkenediyl$_{(c \leq 12)}$, arenediyl$_{(c \leq 12)}$, alkoxydiyl$_{(c \leq 12)}$, alkylaminodiyl$_{(c \leq 12)}$, or a substituted version of any of these groups, $X_7$ is —O—, —S—, —NR$_5$—, —C(O)NR$_5$—, or —NR$_5$C(O)—, wherein $R_5$ is hydrogen, alkyl$_{(c \leq 6)}$, or substituted alkyl$_{(c \leq 6)}$, and $R_4$ is amino, hydroxy, mercapto, carboxy, dicarboxy, or

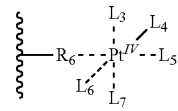

wherein:

$R_6$ is amino or carboxy;

$L_5$ is aqua, ammonia, nitrate, sulfate, halide, hydroxide, phosphate, or glucose-6-phosphate, alkylamine$_{(c \leq 12)}$, cycloalkylamine$_{(c \leq 12)}$, dialkylamine$_{(c \leq 18)}$, dicycloalkylamine$_{(c \leq 18)}$, arylamine$_{(c \leq 12)}$, diarylamine$_{(c \leq 18)}$, diaminoalkane$_{(c \leq 12)}$, diaminocycloalkane$_{(c \leq 12)}$, diaminoarene$_{(c \leq 12)}$, heteroarene$_{(c \leq 12)}$, alkylcarboxylate$_{(c \leq 12)}$, alkyldicarboxylate$_{(c \leq 18)}$, arylcarboxylate$_{(c \leq 12)}$, aryldicarboxylate$_{(c \leq 18)}$, or a substituted version of any of these groups;

$L_3$, $L_4$, and $L_6$ are each independently amino, halide, or $L_3$ and $L_6$ are taken together and are alkyldicarboxylate$_{(c \leq 18)}$ or substituted alkyldicarboxylate$_{(c \leq 18)}$;

$L_7$ is amino, or $L_7$ is taken together with $L_4$ and is diaminocycloalkane$_{(c \leq 12)}$, or substituted diaminocycloalkane$_{(c \leq 12)}$;

provided that $R_6$, $L_3$, $L_4$, $L_5$, $L_6$, and $L_7$ are appropriately charged to obtain a neutral complex provided that at least one of $X_1$, $X_2$, $X_3$, $X_4$, $X_5$, and $X_6$ is a platinum(IV) chelating group;

M is a divalent metal ion or a trivalent metal ion; and $L_1$ and $L_2$ are each absent or anionic ligands independently selected from fluoride, chloride, bromide, carbonate, hydroxide, perchlorate, nitrate, sulfate, trifluoromethylsulfonate, acetylacetonate, acetate, or trifluoroacetate;

provided that when M is a divalent metal ion, then $L_1$ or $L_2$ is absent;

or a pharmaceutically acceptable salt, organometallic isomer, or tautomer thereof.

2. The compound of claim 1, wherein the formula is further defined as:

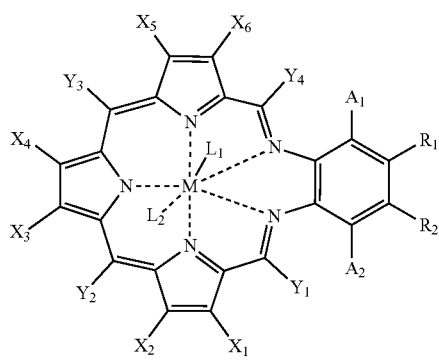
(II)

wherein:
R₁ and R₂ are each independently selected from hydroxy, alkoxy$_{(c≤12)}$, substituted alkoxy$_{(c≤12)}$, or

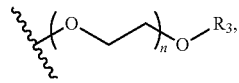

wherein n is 1-20 and R₃ is hydrogen, alkyl$_{(c≤6)}$, or substituted alkyl$_{(c≤6)}$, or a platinum(IV) chelating group;

A₁ and A₂ are each independently selected from hydrogen;

Y₁, Y₂, Y₃, and Y₄ are each independently selected from hydrogen;

X₁, X₂, X₃, X₄, X₅, and X₆ are each independently selected from hydrogen, alkyl$_{(c≤12)}$, alkenyl$_{(c≤12)}$, aryl$_{(c≤12)}$, or a substituted version of any of these groups, or a platinum chelating group of the formula: —A₃—X₇—A₄—R₄, wherein A₃ and A₄ are each independently alkanediyl$_{(c≤12)}$, alkoxydiyl$_{(c≤12)}$, alkylaminodiyl$_{(c≤12)}$, or a substituted version of any of these groups, X₇ is —NR₅—, —C(O)NR₅—, or —NR₅C(O)—, wherein R₅ is hydrogen, alkyl$_{(c≤12)}$, or substituted alkyl$_{(c≤12)}$, and R₄ is hydroxy, carboxy, dicarboxy, or

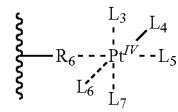

wherein:
R₆ is amino or carboxy,
L₅ is selected from aqua, ammonia, halide, or hydroxide,
diaminoalkane$_{(c≤12)}$, diaminocycloalkane$_{(c≤12)}$, diaminoarene$_{(c≤12)}$, alkyldicarboxylate$_{(c≤18)}$, aryldicarboxylate$_{(c≤18)}$, or a substituted version of any of these groups;
L₃, L₄, and L₆ are each independently amino, halide, or L₃ and L₆ are taken together and are alkyldicarboxylate$_{(c≤18)}$ or substituted alkyldicarboxylate$_{(c≤18)}$; and
L₇ is amino, or L₇ is taken together with L₄ and is diaminocycloalkane$_{(c≤12)}$, or substituted diaminocycloalkane$_{(c≤12)}$;

provided that at least one of X₁, X₂, X₃, X₄, X₅, and X₆ is a platinum(IV) chelating group;

M is a trivalent lanthanide metal ion or a divalent metal ion; and

L₁ and L₂ are each anionic ligands independently selected from fluoride, chloride, bromide, perchlorate, nitrate, sulfate, trifluoromethylsulfonate, acetate, or trifluoroacetate;

or a pharmaceutically acceptable salt, organometallic isomer, or tautomer thereof.

3. The compound of claim 1, wherein the formula is further defined as:

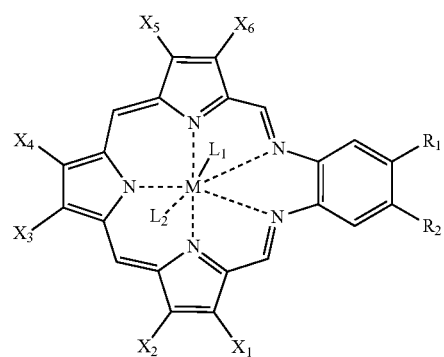
(III)

wherein:
R₁ and R₂ are each independently selected from alkoxy$_{(c≤12)}$, substituted alkoxy$_{(c≤12)}$, or

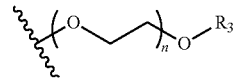

wherein n is 1-20 and R₃ is hydrogen, alkyl$_{(c≤6)}$, or substituted alkyl$_{(c≤6)}$;

or a pharmaceutically acceptable salt, organometallic isomer, or tautomer thereof.

4. The compound of claim 1, wherein the formula is further defined as:

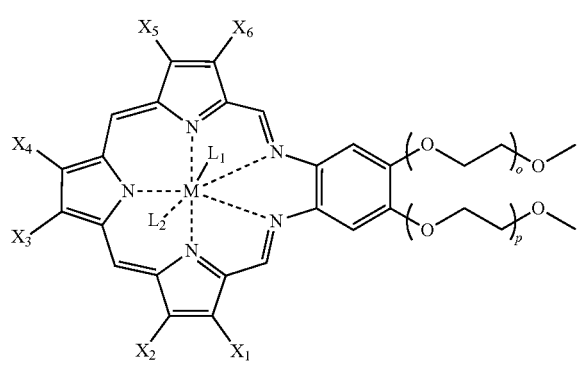
(IV)

wherein:
o and p are each independently 1, 2, 3, 4, 5, or 6 or any range derivable therein;

$X_1$, $X_2$, $X_3$, $X_4$, $X_5$, and $X_6$ are each independently selected from alkyl$_{(c\leq 12)}$ or substituted alkyl$_{(c\leq 12)}$, or a platinum chelating group of the formula: —$A_3$—$X_7$—$A_4$—$R_4$, wherein $A_3$ and $A_4$ are each independently alkanediyl$_{(c\leq 12)}$, alkoxydiyl$_{(c\leq 12)}$, or a substituted version of any of these groups, $X_7$ is —C(O)NR$_5$—, or —NR$_5$C(O)—, wherein $R_5$ is hydrogen, alkyl$_{(c\leq 12)}$, or substituted alkyl$_{(c\leq 12)}$, and $R_4$ is carboxy or

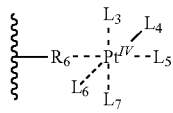

wherein:
   $R_6$ is carboxy;
   $L_5$ is aqua, ammonia, halide, or hydroxide, diaminoalkane$_{(c\leq 12)}$, diaminocycloalkane$_{(c\leq 12)}$, alkyldicarboxylate$_{(c\leq 18)}$, or a substituted version of any of these groups;
   $L_3$, $L_4$, and $L_6$ are each independently amino, halide, or $L_3$ and $L_6$ are taken together and are alkyldicarboxylate$_{(c\leq 18)}$ or substituted alkyldicarboxylate$_{(c\leq 18)}$; and
   $L_7$ is amino, or $L_7$ is taken together with $L_4$ and is diaminocycloalkane$_{(c\leq 12)}$, or substituted diaminocycloalkane$_{(c\leq 12)}$;
provided that at least one of $X_1$, $X_2$, $X_3$, $X_4$, $X_5$, and $X_6$ is a platinum(IV) chelating group;
M is a trivalent lanthanide metal ion; and
$L_1$ and $L_2$ are each anionic ligands independently selected from nitrate, acetate, or trifluoroacetate;
or a pharmaceutically acceptable salt, organometallic isomer, or tautomer thereof.

5. The compound of claim 4, wherein o or p are 2, 3, or 4.

6. The compound of claim 1, wherein $X_1$, $X_3$, $X_4$, $X_5$, or $X_6$ are alkyl$_{(c\leq 12)}$ or substituted alkyl$_{(c\leq 12)}$.

7. The compound of claim 1, wherein $X_2$ is a platinum(IV) chelating group of the formula: —$A_3$—$X_7$—$A_4$—$R_4$, wherein $A_3$ and $A_4$ are each independently alkanediyl$_{(c\leq 12)}$, alkoxydiyl$_{(c\leq 12)}$, or a substituted version of any of these groups, $X_7$ is —C(O)NR$_5$— or —NR$_5$C(O)—, wherein $R_5$ is hydrogen, alkyl$_{(c\leq 12)}$, or substituted alkyl$_{(c\leq 12)}$, and $R_4$ is

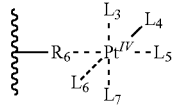

wherein:
   $R_6$ is carboxy;
   $L_5$ is aqua, ammonia, halide, or hydroxide, alkylcarboxylate$_{(c\leq 12)}$ or a substituted version thereof; and
   $L_3$, $L_4$, and $L_6$ are each independently amino, halide, or $L_3$ and $L_6$ are taken together and are alkyldicarboxylate$_{(c\leq 18)}$ or substituted alkyldicarboxylate$_{(c\leq 18)}$;
   $L_7$ is amino, or $L_7$ is taken together with $L_4$ and is diaminocycloalkane$_{(c\leq 12)}$, or substituted diaminocycloalkane$_{(c\leq 12)}$.

8. The compound of claim 7, wherein $A_4$ is alkanediyl$_{(c\leq 12)}$ or substituted alkanediyl$_{(c\leq 12)}$.

9. The compound of claim 7, wherein $R_6$ is carboxy.

10. The compound of claim 7, wherein $L_3$ or $L_6$ are halide.

11. The compound of claim 7, wherein $L_3$ and $L_6$ are taken together and are the same alkyldicarboxylate$_{(c\leq 18)}$.

12. The compound of claim 7, wherein $L_7$ is amino.

13. The compound of claim 7, wherein $L_4$ and $L_7$ are taken together and are diaminocycloalkane$_{(c\leq 12)}$.

14. The compound of claim 1, wherein M is gadolinium.

15. The compound of claim 1, wherein $L_1$ and $L_2$ are acetate or nitrate.

16. A pharmaceutical composition comprising:
   (A) a pharmaceutically acceptable carrier; and
   (B) a compound of claim 1.

17. A method of treating cancer in a patient comprising administering to the patient in need thereof a therapeutically effective amount of a compound of claim 1.

18. The method of claim 17, wherein the cancer is ovarian cancer, testicular cancer, bladder cancer, or colorectal cancer.

* * * * *